US011890330B2

(12) United States Patent
Nelson et al.

(10) Patent No.: US 11,890,330 B2
(45) Date of Patent: Feb. 6, 2024

(54) **ENDOLYSINS ACTIVE AGAINST *BACILLUS* BACTERIA, PHARMACEUTICAL COMPOSITIONS, AND METHODS RELATING THERETO**

(71) Applicants: University of Maryland, College Park, College Park, MD (US); The United States of America, as Represented by the Secretary of the Navy, Arlington, VA (US)

(72) Inventors: Daniel C. Nelson, Rockville, MD (US); Irina V. Etobayeva, Kensington, MD (US)

(73) Assignees: University of Maryland, College Park, College Park, MD (US); The United States of America, as Represented by the Secretary of the Navy, Arlington, VA (US)

( * ) Notice: Subject to any disclaimer, the term of this patent is extended or adjusted under 35 U.S.C. 154(b) by 493 days.

(21) Appl. No.: 17/054,539

(22) PCT Filed: May 16, 2019

(86) PCT No.: PCT/US2019/032669
§ 371 (c)(1),
(2) Date: Nov. 11, 2020

(87) PCT Pub. No.: WO2019/222502
PCT Pub. Date: Nov. 21, 2019

(65) Prior Publication Data
US 2021/0244802 A1 Aug. 12, 2021

Related U.S. Application Data

(60) Provisional application No. 62/673,005, filed on May 17, 2018.

(51) Int. Cl.
*A61K 38/47* (2006.01)
*A61P 31/04* (2006.01)
*A61K 38/16* (2006.01)
*A61K 45/06* (2006.01)
*C12N 9/36* (2006.01)

(52) U.S. Cl.
CPC ............ *A61K 38/47* (2013.01); *A61K 38/162* (2013.01); *A61K 45/06* (2013.01); *A61P 31/04* (2018.01); *C12N 9/2462* (2013.01); *C12Y 302/01017* (2013.01)

(58) Field of Classification Search
CPC ........... C12N 9/2462; C12Y 302/01017; A61P 31/04; A61K 38/47; A61K 38/162; A61K 45/06
See application file for complete search history.

(56) References Cited

U.S. PATENT DOCUMENTS

2010/0092968 A1   4/2010  Beissinger et al.
2010/0120673 A1*  5/2010  Yoong .................... C12N 9/503
                                                     530/350
2016/0010071 A1   1/2016  Lysando et al.

FOREIGN PATENT DOCUMENTS

KR    20180004584    1/2018
WO    WO 2017/061732    4/2017

OTHER PUBLICATIONS

Jose H. Ting, et al., Complete Genome of Bacillus thuringiensis Myophage BigBertha, 1 Genome Announc. 1 (Year: 2013).*
Abedon, S.T. (2011) "*Lysis From Without*," Bacteriophage 1(1):46-49.
Berman, H.M. et al. (2000) "*The Protein Data Bank*," Nucleic Acids Research 28:235-242.
Bitter, G.A. et al. (1987) "*Expression and Secretion Vectors for Yeast*," Meth. Enzymol. 153:516-544.
Büttner, F.M. et al. (2015) "*X-Ray Crystallography And Its Impact On Understanding Bacterial Cell Wall Remodeling Processes*," International Journal of Medical Microbiology 305:209-216.
Celik, E. et al. (2012) "*Production Of Recombinant Proteins By Yeast Cells*," Biotechnol. Adv. 30(5):1108-1118.
Cerda-Costa, N. & Gomis-Ruth, F.X. (2014) "*Architecture and Function Of Metallopeptidase Catalytic Domains*," Protein Sci. 23(2):123-44.
Ceuppens, S. et al. (2013) "*Diversity of Bacillus cereus Group Strains Is Reflected In Their Broad Range Of Pathogenicity And Diverse Ecological Lifestyles*," FEMS Microbiol. Ecol. 84(3):433-450.
Dunne, M et al. (2016) "*Crystal Structure Of The CTP1L Endolysin Reveals How Its Activity Is Regulated By A Secondary Translation Product*," J Biol Chem 291(10):4882-4893.
Firczuk, M. & Bochtler, M. (2007) "*Folds And Activities Of Peptidoglycan Amidases*," Fems Microbiology Letters 31:676-691.
Fischetti, V.A. (2005) "*Bacteriophage Lytic Enzymes: Novel Anti-Infectives*," Trends Microbiol 13(10):491-496.
Fischetti, V. A. (2010) "*Bacteriophage Endolysins: A Novel Anti-Infective To Control Gram-Positive Pathogens*," Int. J. Med. Microbiol. 300(6):357-362.
Fiser, A. et al. (2000) "*Modeling Of Loops In Protein Structures*," Protein Science 9:1753-1773.
Garcia, P. et al. (2010) "*Synergy Between The Phage Endolysin Lysh5 And Nisin To Kill Staphylococcus aureus In Pasteurized Milk*," Int. J. Food Microbiol. 141(3):151-155.
Gherardi, G. (2016) "*Bacillus cereus Disease Other Than Food-Borne Poisoning*," In: The Diverse Faces of *Bacillus* Cereus, Savini, V., Ed., Elsevier, Inc., London, pp. 93-116.
Helgason, E. et al. (2000) "*Bacillus anthracis, Bacillus cereus, And Bacillus thuringiensis—One Species On The Basis Of Genetic Evidence*," Appl. Environ. Microbiol. 66(6):2627-2630.

(Continued)

*Primary Examiner* — Sean M Basquill
(74) *Attorney, Agent, or Firm* — Hylton Rodic Law PLLC

(57) ABSTRACT

The present invention relates to methods of treating or preventing a bacterial disease or infection, antibacterial compositions, and antibacterial surfaces, including an isolated polypeptide comprising an enzymatically active domain (EAD) of a *Bacillus* bacteriophage endolysin.

5 Claims, 15 Drawing Sheets

Specification includes a Sequence Listing.

(56) References Cited

OTHER PUBLICATIONS

Hoffmaster, A.R. et al. (2006) "*Characterization Of Bacillus Cereus Isolates Associated With Fatal Pneumonias: Strains Are Closely Related To Bacillus Anthracis And Harbor B. Anthracis Virulence Genes,*" J. Clin. Microbiol. 44(9):3352-3360.
Holliger, P. (2002) "*Expression Of Antibody Fragments In Pichia Pastoris,*" Methods Mol. Biol. 178:349-357.
Jones, D.T. et al. (1992) "*The Rapid Generation Of Mutation Data Matrices From Protein Sequences,*" Comput. Appl. Biosci. 8(3):275-82.
Jordan, T.C. et al. (2014) "*A Broadly Implementable Research Course In Phage Discovery And Genomics For First-Year Undergraduate Students,*" Mbio 5(1):E01051-13.
Khasnabis, J. et al. (2017) "*Incidence Of Multiple Drug Resistant Bacillus Cereus In Some Popular Snacks And Sweets Sold In Kolkata City, India,*" Indian J. Microbiol. Res. 4(1):14-19.
Kim, C.W. et al. (2015) "*Prevalence, Genetic Diversity, And Antibiotic Resistance Of Bacillus cereus Isolated From Korean Fermented Soybean Products,*" J. Food Sci. 80(1):M123-M128.
Korndörfer, I.P. et al. (2006) "*The Crystal Structure Of The Bacteriophage PSA Endolysin Reveals A Unique Fold Responsible For Specific Recognition Of Listeria Cell Walls,*" J. Molec. Biol. 364:678-689.
Korndörfer, I.P. et al. (2008) "*Structural Analysis Of The L-Alanoyl-D-Glutamate Endopeptidase Domain Of Listeria Bacteriophage Endolysin Ply500 Reveals A New Member Of The Las Peptidase Family,*" Acta Crystallographica Section D: Biological Crystallography 64:644-650.
Kumar, S. et al. (2016) "*Mega7: Molecular Evolutionary Genetics Analysis Version 7.0 For Bigger Datasets,*" Mol. Biol. Evol. 33(7):1870-1874.
Kutsuna, S. et al. (2017) "*Risk Factors Of Catheter-Related Bloodstream Infection Caused By Bacillus cereus: Case-Control Study In 8 Teaching Hospitals In Japan,*" Am. J. Infect. Control 45(11):1281-1283.
Larkin, M.A. et al. (2007) "*Clustal W And Clustal X Version 2.0,*" Bioinformatics 23:2947-2948.
Laskowski, R.A. et al. (1993) "*Procheck: A Program To Check The Stereochemical Quality Of Protein Structures,*" J. Appl. Crystal. 26:283-291.
Leggett, M.J. et al. (2012) "*Bacterial Spore Structures And Their Protective Role In Biocide Resistance,*" J. Appl. Microbiol. 113(3):485-498.
Leggett, M.J. et al. (2015) "*Resistance To And Killing By The Sporicidal Microbicide Peracetic Acid,*" J. Antimicrob. Chemother. 70(3):773-779.
Linden, S.B. et al. (2015) "*Biochemical And Biophysical Characterization Of Plygres, A Bacteriophage Endolysin Active Against Methicillin-Resistant Staphylococcus aureus,*" Appl. Microbiol. Biotechnol. 99(2):741-752.
Loeffler, J.M. et al. (2001) "*Rapid Killing Of Streptococcus Pneumoniae With A Bacteriophage Cell Wall Hydrolase,*" Science 294(5549):2170-2172.
Loessner, M.J. (2005) "*Bacteriophage Endolysins—Current State Of Research And Applications,*" Curr. Opin. Microbiol. 8(4):480-487.
Loessner, M.J. (1997) "*Three Bacillus cereus Bacteriophage Endolysins Are Unrelated But Reveal High Homology To Cell Wall Hydrolases From Different Bacilli,*" J. Bacteriol. 179(9):2845-2851.
Low, L.Y. et al. (2005) "*Structure And Lytic Activity Of A Bacillus anthracis Prophage Endolysin,*" J. Biol. Chem. 280(42):35433-35439.
Low, L.Y. et al. (2011) "*Role Of Net Charge On Catalytic Domain And Influence Of Cell Wall Binding Domain On Bactericidal Activity, Specificity, And Host Range Of Phage Lysins,*" J. Biol. Chem. 286(39):34391-34403.
Mattanovich, D. et al. (2012) "*Recombinant Protein Production in Yeasts,*" Methods Mol. Biol. 824:329-358.
Mayer, M.J. et al. (2011) "*Structure-Based Modification Of A Clostridium Difficile-Targeting Endolysin Affects Activity And Host Range,*" J. Bacteriol. 193(19):5477-5486.

McCafferty, D.G. et al. (1997) "*Mutational Analysis Of Potential Zinc-Binding Residues In The Active Site Of The Enterococcal D-Ala-D-Ala Dipeptidase Vanx,*" Biochemistry 36(34):10498-10505.
Merzougui, S. et al. (2014) "*Prevalence, PFGE Typing, And Antibiotic Resistance Of Bacillus Cereus Group Isolated From Food In Morocco,*" Foodborne Pathog. Dis. 11(2):145-149.
Nelson, D.C. et al. (2012) "*Endolysins As Antimicrobials,*" Adv. Virus Res. 83:299-365.
Okinaka, R.T. & Keim, P. (2016) "*The Phylogeny Of Bacillus cereus sensu lato,*" Microbiol. Spectr. 4(1):Tbs-0012-2012:1-12.
Oliveira, H. et al. (2013) "*Molecular Aspects And Comparative Genomics Of Bacteriophage Endolysins,*" J. Virol. 87(8):4558-4570.
Park, J. et al. (2012) "*Characterization Of An Endolysin, Lysbps 13, From A Bacillus cereus Bacteriophage,*" FEMS Microbiol. Lett. 332(1):76-83.
PCT International Search Report, PCT/US2019/032669 (WO 2019/222502) (4 Pages).
PCT Written Opinion, PCT/US2019/032669 (WO 2019/222502) (10 Pages).
Pires, D.P. et al. (2016) "*Bacteriophage-Encoded Depolymerases: Their Diversity And Biotechnological Applications,*" Appl. Microbiol. Biotechnol. 100(5):2141-2151.
Proenca, D. et al. (2015) "*A Two-Component, Multimeric Endolysin Encoded By A Single Gene,*" Mol. Microbiol. 95(5):739-753.
Royet, J. & Dziarski, R. (2007) "*Peptidoglycan Recognition Proteins: Pleiotropic Sensors And Effectors Of Antimicrobial Defences,*" Nat. Rev. Microbiol. 5(4):264-277.
Saedi, M.S. et al. (1987) "*Cloning And Purification Of A Unique Lysozyme Produced By Bacillus Phage Phi 29,*" Proc. Natl. Acad. Sci. (U.S.A.) 84(4):955-958.
Šali, A. & Blundell, T.L., (1993) "*Comparative Protein Modelling By Satisfaction Of Spatial Restraints,*" J. Molec. Biol. 234:779-815.
Schmelcher, M. & Loessner, M.J. (2014) "*Application Of Bacteriophages For Detection Of Foodborne Pathogens,*" Bacteriophage 4(1):E28137:1-14.
Schmelcher, M. et al. (2011) "*Domain Shuffling And Module Engineering Of Listeria Phage Endolysins For Enhanced Lytic Activity And Binding Affinity,*" Microb. Biotechnol. 4(5):651-662.
Schmelcher, M. et al. (2012) "*Bacteriophage Endolysins As Novel Antimicrobials,*" Future Microbiology 7:1147-1171.
Schuch, R. et al. (2002) "*A Bacteriolytic Agent That Detects And Kills Bacillus Anthracis,*" Nature 418(6900):884-889.
Schuch, R. et al. (2009) "*A Genetic Screen To Identify Bacteriophage Lysins,*" Methods Mol. Biol. 502:307-319.
Schuch, R. et al. (2013) "*Use Of A Bacteriophage Lysin To Identify A Novel Target For Antimicrobial Development,*" Plos One 8(4):E60754:1-9.
Shen Y. et al. (2012) "*Phage-Based Enzybiotics,*" In: Bacteriophages in Health and Disease, Abedon, S. and Hyman, P. (Eds), Cabi Press, pp. 217-239.
Shen, M.Y. & Sali, A. (2006) "*Statistical Potential For Assessment And Prediction Of Protein Structures,*" Protein Science 15:2507-2524.
Shen, Y. et al., (2016) "*A Bacteriophage Endolysin That Eliminates Intracellular Streptococci,*" Elife 5:E13152:1-26.
Söding, J. et al. (2005) "*The HHpred Interactive Server For Protein Homology Detection And Structure Prediction,*" Nucl. Acids Res. 33:W244-W248.
Son, B. et al. (2012) "*Characterization Of Lysb4, An Endolysin From The Bacillus cereus-Infecting Bacteriophage B4,*" BMC Microbiology 12:33:1-9.
Yoong, P. et al., (2006) "*Plyph, A Bacteriolytic Enzyme With A Broad pH Range Of Activity And Lytic Action Against Bacillus anthracis,*" J. Bacteriol. 188(7):2711-2714.
Yuan, Y. et al. (2012) "*Characteristics Of A Broad Lytic Spectrum Endolysin From Phage BtCS33 Of Bacillus thuringiensis,*" BMC Microbiology 12:297:1-9.

\* cited by examiner

A

```
                    10         20         30
                ....|....| ....|....| ....|....|
2vo9_a     1    MALTEAWLIE KANRKLNAGG MYKITSDKTR    30
PlyP56     1    MAMALQTLID KANRKLNISG MRKDVADRTR    30
                **::  **:  ******* .* * *  .:*:**

40         50         60
                ....|....| ....|....| ....|....|
2vo9_a    31    NVIKKMAKEG IYLCVAQGFR STAEQNALYA    60
PlyP56    31    AVITQMHAQG IYICVAQGFR SPAEQDALYA    60
                **.:*  :*  **:****:* * *** :****

70         80    ↓    90 ↓
                ....|....| ....|....| ....|....|
2vo9_a    61    QGRTKPGAIV THARGGQSNH NYGVAVDLCL    90
PlyP56    61    QGRYKPGNIV THARGGQSNH NYGVAVDLCL    90
                *******  ** *** ****** **********

100        110        120
                ....|....| ....|....| ....|....|
2vo9_a    91    YTNDGKDVIW ESTLSRNKV  VAAMKAEGFK   120
PlyP56    91    YTQDGSDVIW TVEGN-FRKV IAAMKGQGFK   119
                **.:**.****  .:**  :****.:***
                        ⇩    ↓        140
                ....|....| ....|....| ....|..
2vo9_a   121    WGGDWKSFKD YPHFELCDAV SGEKIPA    147
PlyP56   120    WGGDWVSFKD YPHFELYDVV GGQKPPA    146
                ***** **** ****** *.* .*:* **
```

B

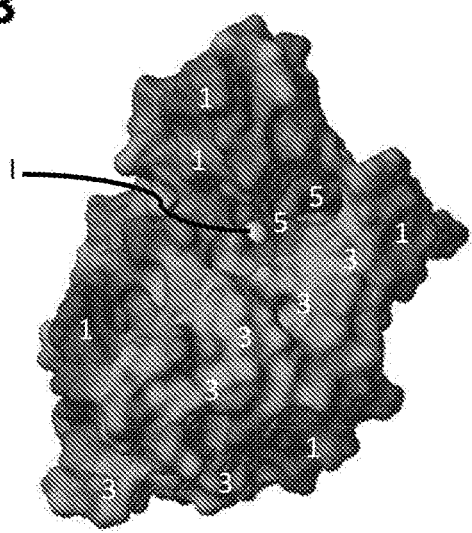

C

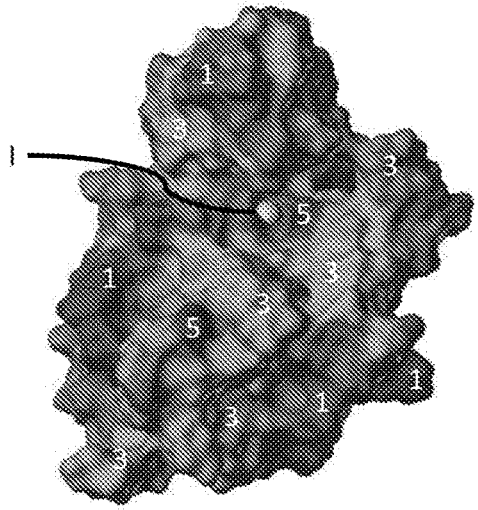

```
                          10         20         30
                   ....|....| ....|....| ....|....|
lyb0_a       1     MEIRKKLVVP SKYGTKCPYT MKPKIITVHN    30
PlyN74       1     MNINTQYLVT DPERLKVINN MNPTEITFHN    30
                   *:*..: :*. .   *      *:*. **.**

40         50         60
                   ....|....| ....|....| ....|....|
lyb0_a       31    TYNDAPAENE VNYMITNNME VSFHVAVDDK    60
PlyN74       31    TYNDASASAE VRNVRNNSTG TSFHTAVDDF    60
                   *****.*. *   *. :.*.  .***.****

70         80         90
                   ....|....| ....|....| ....|....|
lyb0_a       61    QAIQGIPWER NAWACCDN-  PCNRESISV     89
PlyN74       61    EVQQVVPFDR NAWHACDOKY GAGNRNSIGV    90
                   :. * :*:.* ***..***  *..***:**.*

⇩         100        110        120
                   ....|....| ....|....| ....|....|
lyb0_a       90    EICYSKSGED RYYKAENHAV DVVRQLMSMY   119
PlyN74       91    EICYSMSGGE RYRKAELNAI EHISDLMVRF   120
                   ***** ***: ** *** **: : : :**   :

⬇         ⬇        150
                   ....|....| ....|....| ....|....|
lyb0_a       120   NIPIENVRTH QSWSGKYCPH RMLAEQRWGA   149
PlyN74       121   GIPISKVKTH QERNGKYCPH RMLDEQRVGW   150
                   .***.:*:** *. .****** *** *** *

....|..
lyb0_a       150   FIQKVK                               155
PlyN74       151   FKAECE                               156
                   *    : :
```

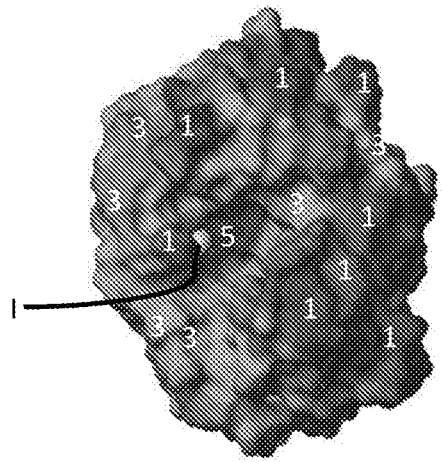

ENDOLYSINS ACTIVE AGAINST BACILLUS BACTERIA, PHARMACEUTICAL COMPOSITIONS, AND METHODS RELATING THERETO

CROSS-REFERENCE TO RELATED APPLICATIONS

This application is a § 371 National Stage Application of PCT/US2019/032669, filed May 16, 2019, which application is based on U.S. Provisional Patent Application Ser. No. 62/673,005, filed May 17, 2018, each of which applications is incorporated herein by reference in its entirety and to which priority is claimed.

STATEMENT REGARDING FEDERALLY SPONSORED RESEARCH OR DEVELOPMENT

This invention was made with government support under Grant No. 1R41AI122666 awarded by the National Institutes of Health (NIH). The government has certain rights in this invention.

REFERENCE TO SEQUENCE LISTING

This application includes one or more Sequence Listings pursuant to 37 C.F.R. 1.821 et seq., which are disclosed in computer-readable media (file name: 2105_0070_SeqList_ST25, created on May 14, 2019 and having a size of 53,857 bytes), which file is herein incorporated by reference in its entirety.

FIELD OF THE INVENTION

The present invention relates to methods of treating or preventing bacterial infection, antibacterial compositions, and devices including antibacterial surfaces, comprising isolated Bacillus bacteriophage endolysins.

BACKGROUND OF THE INVENTION

The Bacillus genus consists of a diverse collection of aerobic organisms that are common residents of the soil and occasionally become opportunistic pathogens of humans. Bacillus species are Gram-positive, rod-shaped bacilli that also form endospores, which allow their survival under adverse environmental conditions. Once these conditions are resolved, endospores germinate into vegetative bacilli to continue their life cycle. From the soil, vegetative bacilli or endospores can be transmitted to humans or animals via contaminated water and produce. Resistant to irradiation, endospores allow the bacteria to remain dormant for long periods of time on surfaces, e.g., such as in medical and food-processing facilities, making it virtually impossible to eliminate pathogenic bacilli from the environment (Leggett, M J et al., *Bacterial spore structures and their protective role in biocide resistance*. J Appl Microbiol 2012, 113(3): 485-498).

Although the majority of bacilli are relatively harmless to humans and animals (Ceuppens, S et al., *Diversity of Bacillus cereus group strains is reflected in their broad range ofpathogenicity and diverse ecological lifestyles*. FEMS Microbiol Ecol 2013, 84(3):433-450), genetically related species of the *B. cereus sensu lato* group are capable of causing clinical disease and toxin-mediated food poisoning. Among these species, the most phenotypically related are *B. cereus, B. anthracis*, and *B. thuringiensis* (Okinaka, RT & Keim, P, The *Phylogeny of Bacillus cereus sensu lato*. Microbiol Spectr 2016, 4(1):TBS-0012-2012). *B. cereus* is capable of producing both emetic and diarrheal toxins. These species are opportunistic pathogens and widespread food contaminants highly resilient to decontamination and/ or pasteurization efforts (Leggett, M J et al., *Resistance to and killing by the sporicidal microbicide peracetic acid*. J Antimicrob Chemother 2015, 70(3):773-779). In addition to causing gastrointestinal conditions, *B. cereus* species are also capable of causing ocular infections (Gherardi, G, *Bacillus cereus disease other than food-borne poisoning*. In The Diverse Faces of *Bacillus cereus*, Savini, V., Ed. Elsevier, Inc.: London, 2016; pp 93-116) and catheter-associated blood stream infections (Kutsuna, S et al., *Risk factors of catheter-related bloodstream infection caused by Bacillus cereus: Case-control study in 8 teaching hospitals in Japan*. Am J Infect Control 2017, 45(11):1281-1283).

*B. anthracis* is an obligate pathogen and the etiologic agent of anthrax. While this organism generally is restricted to grazing animals, systemic anthrax has a high fatality rate in humans due to secretion of a three-protein toxin. While *B. cereus* and *B. anthracis* are known for causing disease and food poisoning in humans and animals, *B. thuringiensis* is an insect pathogen and its parasporal crystal proteins are used as an insecticide (Aronson, A I, Insecticidal toxins. In *Bacillus subtilis* and Other Gram-Positive Bacteria, Sonenshein, A. L., Hoch, J. A., Losick, R., Ed. American Society for Microbiology: Washington, D.C., 1993; pp 953-963). Otherwise, the three members of the *B. cereus sensu lato* group have very little differences in their genomes and often share the same plasmid-associated pathogenicity genes, which make it difficult to differentiate the species from one another (Hoffmaster, A R et al., *Characterization of Bacillus cereus isolates associated with fatal pneumonias: strains are closely related to Bacillus anthracis and harbor B. anthracis virulence genes*. J Clin Microbiol 2006, 44(9):3352-3360).

A growing number of reports about multi-drug resistant *B. cereus* isolates in food have been reported worldwide (Khasnabis, J et al., *Incidence of multiple drug resistant Bacillus cereus in some popular snacks and sweets sold in Kolkata city, India*. Indian J Microbiol Res 2017, 4(1):14-19; Kim, C W et al., *Prevalence, genetic diversity, and antibiotic resistance of Bacillus cereus isolated from Korean fermented soybean products*. J Food Sci 2015, 80(1):M123-128; Merzougui, S et al., *Prevalence, PFGE typing, and antibiotic resistance of Bacillus cereus group isolated from food in Morocco*. Foodborne Pathog Dis 2014, 11(2):145-149), which has prompted a search for an alternative to conventional antibiotics. Bacteriophage-encoded endolysins have been researched as one such alternative (Fischetti, VA, *Bacteriophage lytic enzymes: novel anti-infectives*. Trends Microbiol 2005, 13(10):491-496; Loessner, M. J., *Bacteriophage endolysins—current state of research and applications*. Curr Opin Microbiol 2005, 8(4):480-487).

Endolysins are enzymes encoded by the late genes during a bacteriophage replication cycle. Once synthesized, endolysins target evolutionarily conserved covalent bonds that are present within the peptidoglycan of bacterial cells to disrupt the bacterial cell wall. The bacterial cell wall peptidoglycan is highly conserved among most bacteria, and cleavage of only a few bonds is believed to disrupt the bacterial cell wall. Once produced within the bacterial cytoplasm by replicating bacteriophage, endolysins hydrolyze bonds in the bacterial cell wall (i.e. peptidoglycan) until lysis is complete. Thus, the host bacteria are lysed from the inside to allow bacteriophage progeny release into the extracellular environment (Fischetti, V. A., *Bacteriophage* endolysins: a novel anti-infective to control Gram-positive pathogens. Int J Med Microbiol 2010, 300(6):357-362). Significantly, endolysins applied extrinsically also can compromise the peptidoglycan integrity in the absence of a bacteriophage delivery system (Loeffler, J M et al., *Rapid killing of Streptococcus pneumoniae with a bacteriophage cell wall hydrolase*. Science 2001, 294(5549):2170-2172; Royet, J & Dziarski, R, *Peptidoglycan recognition proteins: pleiotropic sensors and effectors of antimicrobial defences*. Nat Rev Microbiol 2007, 5(4):264-277; Schuch, R et al., *A bacteriolytic agent that detects and kills Bacillus anthracis*. Nature 2002, 418(6900):884-889; Shen, Y et al., *A bacteriophage endolysin that eliminates intracellular streptococci*. Elife 2016, 5).

The idea of utilizing endolysins therapeutically is based on the phenomenon of "lysis from without", a phrase used to describe the destruction of the bacterial envelope without production of phage virions (Abedon S T (2011) *Lysis from without*. Bacteriophage 1(1):46-49). This phenomenon only occurs in Gram-positive organisms because such bacteria lack an outer membrane protecting the cell wall (Schmelcher et al.(2011) *Domain shuffling and module engineering of Listeria phage endolysins for enhanced lytic activity and binding affinity*. Microb Biotechnol 4(5):651-62). Rather, the cell wall of such Gram-positive bacteria includes interconnecting layers consisting primarily of peptidoglycan. Gram-positive bacteria include, inter alia, numerous species within the genera *Actinomyces, Bacillus, Listeria, Lactococcus, Staphylococcus, Streptococcus, Enterococcus, Mycobacterium, Corynebacterium*, and *Clostridium*.

Generally, endolysins derived from bacteriophage that infect Gram-positive hosts consist of two domains: a conserved N-terminal enzymatically active domain (EAD) fused via a short linker sequence to a C-terminal cell wall binding domain (CBD) (Nelson, D C et al., *Endolysins as antimicrobials*. Adv Virus Res 2012, 83, 299-365). The EAD is responsible for cleaving specific covalent bonds in the peptidoglycan structure that are essential for maintaining its intrinsic structural integrity. The CBD confers endolysin specificity by recognizing and noncovalent binding to species- or strain-specific epitopes associated with the cell envelope. It is the high specificity derived by the combined actions of the EAD and CBD that cause endolysins to be highly refractory to the resistance commonly observed upon treatment with classical antibiotics (Fischetti V A (2005) *Bacteriophage lytic enzymes: novel anti-infectives*. Trends Microbiol 13(10):491-6; Schuch R et al.(2002) *A bacteriolytic agent that detects and kills Bacillus anthracis*. Nature 418(6900):884-9). This is due to the evolution of bacteriophage to target specific, conserved bonds in the peptidoglycan of a bacteria cell wall, ensuring that the progeny phage will survive (Low L Y et al.(2011) *Role of net charge on catalytic domain and influence of cell wall binding domain on bactericidal activity, specificity, and host range of phage lysins*. J Biol Chem 286(39):34391-403). However, if resistance were to develop, endolysins may be engineered through domain shuffling or used in combination with other endolysins or antibiotics to prolong the use of these enzymes (Shen Y et al.(2012) *Phage-based Enzybiotics*. In: Abedon S, Hyman P (eds) Bacteriophages in Health and Disease. CABI Press, pp 217-239).

Based on the cleavage sites of one of the major covalent bonds within the bacterial peptidoglycan polymer, EADs are divided into five conserved classes: muramidases, glucosaminidases, endopeptidases, l-alanine amidases, and lytic transglycosylases. In contrast, CBDs are diverse in sequence and confer targeted specificity to a bacterial species or strain by binding a conserved carbohydrate moiety on the bacterial cell surface (Schuch, R et al., *Use of a bacteriophage lysin to identify a novel target for antimicrobial development*. PLoS One 2013, 8(4):e60754).

Thus, identified endolysins have been shown to be effective in killing specific bacterial strains. However, there still exists a need for additional and/or alternative endolysin-based therapeutics, particularly therapeutics exhibiting superior activity and/or which target other bacterial strains as compared to known therapeutics.

SUMMARY OF THE INVENTION

The increasing rate of resistance of pathogenic bacteria to classical antibiotics has driven research towards identification of other means to fight infectious diseases. The present invention relates to methods of treating such infectious diseases by administering to a subject a therapeutically effective amount of particular bacteriophage-encoded peptidoglycan hydrolase, called endolysin(s). During a lytic bacteriophage infection cycle within a host organism, proteins known as holins are produced to rupture the bacterial membrane, allowing the accumulating phage-encoded lysins to gain access to the cell wall. The released lysins are free to cleave covalent bonds in the peptidoglycan, causing rupture and liberation of progeny bacteriophage. Exogenous addition of lysins to susceptible Gram-positive bacteria can produce complete lysis in the absence of bacteriophage.

The present invention is directed to nine lysin families, within bacteriophage that infect *Bacillus* species. Embodiments directed to archetype lysins that define each family are disclosed. The endolysin polypeptides of the present invention lyse the bacterial cell wall upon direct contact, are not inhibited by traditional antibiotic resistance mechanisms. As such, the disclosed endolysin polypeptide(s) of the present invention are well suited for various applications, e.g., such as in the areas of food safety, human health, and veterinary science.

In particular, the present invention is directed to methods, compositions and devices incorporating or utilizing endolysin polypeptide(s) disclosed herein, including endolysins from bacteriophages Phrodo, Nigalana, and/or TsarBomba, referred to herein as PlyP56, PlyN74, and PlyTB40, respectively. PlyP56, PlyN74 and PlyTB40 have relatively homologous CBDs and demonstrate particularly high activity against various *Bacillus* species, including *B. cereus* species. The present invention is also directed to methods, compositions and devices incorporating or utilizing endolysin polypeptide(s) from bacteriophages Angel (PlyA92), Pegasus (PlyP108), Stitch (PlyS31), Taylor (PlyT31), Vinny (PlyV63), and/or Waukesha (PlyW68). Based on characterization of their biochemical properties and specificity, the disclosed endolysin polypeptides as well as variants thereof are suitable for various biomedical and bioengineering applications.

In accordance with disclosed embodiments, a method of treating a bacterial infection in a subject comprises administering to said subject a therapeutically effective amount of an isolated polypeptide comprising an EAD comprising the amino acid sequence of SEQ ID NO: 3, SEQ ID NO:7 SEQ ID NO:11, SEQ ID NO:15, SEQ ID NO:19, SEQ ID NO:24, SEQ ID NO:28, SEQ ID NO:33 or SEQ ID NO:37, or variants thereof have at least about 90% identity thereto. In some implementations, the isolated polypeptide further comprises an CBD(s) comprising the amino acid sequence of SEQ ID NO:4, SEQ ID NO:8, SEQ ID NO:12, SEQ ID NO:16, SEQ ID NO:20, SEQ ID NO:21, SEQ ID NO:25, SEQ ID NO:29, SEQ ID NO:30, SEQ ID NO:34 or SEQ ID NO:38.

In accordance with disclosed embodiments, a pharmaceutical composition for killing Gram-positive bacteria comprises an isolated polypeptide comprising the amino acid sequence of SEQ ID NO: 3, SEQ ID NO:7 SEQ ID NO:11, SEQ ID NO:15, SEQ ID NO:19, SEQ ID NO:24, SEQ ID NO:28, SEQ ID NO:33 or SEQ ID NO:37, or variants thereof have at least about 90% identity thereto, and effective for killing said bacteria, and a pharmaceutically acceptable carrier. In some implementations, the isolated polypeptide of the composition further comprises the amino acid sequence of SEQ ID NO:4, SEQ ID NO:8, SEQ ID NO:12, SEQ ID NO:16, SEQ ID NO:20, SEQ ID NO:21, SEQ ID NO:25, SEQ ID NO:29, SEQ ID NO:30, SEQ ID NO:34 or SEQ ID NO:38.

In accordance with disclosed embodiments, a surface of a substrate comprises an antibacterial coating, wherein the coating comprises an isolated polypeptide comprising the amino acid sequence of SEQ ID NO: 3, SEQ ID NO:7 SEQ ID NO:11, SEQ ID NO:15, SEQ ID NO:19, SEQ ID NO:24, SEQ ID NO:28, SEQ ID NO:33 or SEQ ID NO:37, or variants thereof have at least about 90% identity thereto, and effective for killing said bacteria, and a pharmaceutically acceptable carrier. In some implementations, the isolated polypeptide of the surface further comprises the amino acid sequence of SEQ ID NO:4, SEQ ID NO:8, SEQ ID NO:12, SEQ ID NO:16, SEQ ID NO:20, SEQ ID NO:21, SEQ ID NO:25, SEQ ID NO:29, SEQ ID NO:30, SEQ ID NO:34 or SEQ ID NO:38. In some implementations, the substrate is a medical device.

Note that any of the disclosed EADs may be paired with any of the disclosed CBDs. Thus, methods, compositions and surfaces and/or devices disclosed herein may comprise one or more EAD(s) from bacteriophage PlyP56, PlyN74, PlyTB40, PlyA92, PlyP108, PlyS31, PlyT31, PlyV63 and/or PlyW68, and additionally comprise one or more CBD(s) from the another bacteriophage PlyP56, PlyN74, PlyTB40, PlyA92, PlyP108, PlyS31, PlyT31, PlyV63 and/or PlyW68.

BRIEF DESCRIPTION OF THE DRAWINGS

FIG. 6 illustrates PlyP56 sequence alignment with structural homolog Ply500. Panel A shows sequence alignment of *L. monocytogenes* phage A500 (Ply500) from PDB entry 2VO9 and PlyP56 EADs (Clustal X alignment symbols: asterisk=identical; colon=strongly similar; period=weakly similar; space=not similar). Overall percent identity (#identical/#total)=70.1%; percent similarity [(#identical+#strongly similar)/#total]=81.6%. Arrows indicate the metal-binding residues (black fill) and the catalytic base/acid (white fill). The conserved SxHxxGxAxD zinc-binding motif is highlighted with a rectangle. Ovals represent sequence insertions or deletions; see FIG. 5 (Panels B-C). Connolly surfaces coded by electrostatic potential (1/blue=most positive; 3/green=intermediate; 5/red=most negative) for the template Ply500 shown in Panel B, and the modeled PlyP56 EAD shown in Panel C; a sphere I represents the $Zn^{2+}$ ion.

FIG. 7 illustrates PlyN74 sequence alignment with structural homolog PlyL. Panel A shows sequence alignment of *B. anthracis* λ prophage Ba02 (PlyL) from PDB entry 1YB0 and PlyN74 EADs (Clustal X alignment symbols: asterisk=identical; colon=strongly similar; period=weakly similar; space=not similar). Overall percent identity (#identical/#total)=51.3%; percent similarity [(#identical+#strongly similar)/#total]=64.1%. Arrows indicate the metal-binding residues (black fill) and the catalytic base/acid (white fill). Ovals represent sequence insertions or deletions; see FIG. 5 (Panels B-C). Connolly surfaces coded by electrostatic potential (1/blue=most positive; 3/green=intermediate; 5/red=most negative) for the template PlyL shown in Panel B, and the modeled PlyN74 EAD shown in Panel C; a sphere I represents the $Zn^{2+}$ ion.

FIG. 12 are bright field images showing binding of ALEXA FLUOR®-labeled CBDs to a cell wall of bacilli. Decoration of *B. cereus* ATCC 4342 (two left columns) and *B. anthracis* Ames 35 (two right columns) by fluorescently tagged CBDs of PlyP56, PlyN74, and PlyTB40. 1000X bright-field images (columns 1 and 3) are shown with their corresponding fluorescent images (columns 2 and 4). The ALEXA FLUOR®-labeled CBDs recognize and bind to an evenly distributed ligand on the surface of *B. cereus* and *B. anthracis*. Scale bar (columns 1 and 3) equals 5 μm.

DETAILED DESCRIPTION OF EMBODIMENTS OF THE INVENTION

The present invention relates to compositions, methods and devices for preventing or treating disease, infection or contamination associated with or caused by Gram-positive bacteria, such compositions, methods and devices incorporating and/or utlizing isolated endolysin polypeptide(s) from *Bacillus* bacteriophage, including bacteriophage Phrodo, Nigalana, and/or TsarBomba, referred to herein as PlyP56, PlyN74, and PlyTB40, respectively.

A "polypeptide" includes a polymer molecule comprised of multiple amino acid residues joined in a linear manner. The polypeptide may include conservative substitutions where the naturally occurring amino acid(s) is replaced by one having similar properties, where such conservative substitutions do not alter the function of the polypeptide. The term "isolated" means at least partially purified from a starting material. The term "purified" means that the biological material has been measurably increased in concentration by any purification process, including by not limited to, column chromatography, HPLC, precipitation, electrophoresis, etc., thereby partially, substantially or completely removing impurities. An "isolated" endolysin polypeptide(s) or nucleic acid encoding such polypeptide(s) is preferably free or substantially free of material with which they are naturally associated such as other polypeptides or nucleic acids. However, those of skill in the art will readily appreciate that the amount of purification necessary will depend upon the use of the material. In addition, polypeptides and nucleic acid may be formulated or mixed with pharmaceutically acceptable carriers, diluents or adjuvants (e.g., such as in pharmaceutical compositions and/or when used in methods of treatment or therapy) and still be isolated.

Each of PlyP56, PlyN74 and PlyTB40 endolysin(s) of the present invention displays dose-dependent antimicrobial activity against various *Bacillus* species, including *B. cereus* and *B. anthracis*. PlyP56, PlyN74, and PlyTB40 each contain a singular N-terminal EAD and a C-terminal CBD. In contrast to the non-homologous EADs, all three of the subject endolysins have a type of src-homology 3 (SH3) domain as their C-terminal CBD. The CBDs of PlyP56 and PlyN74 have SH3 bacterial domains, known as SH3b domains (smart 00287), which share 94% identity. The PlyTB40 CBD has a very similar SH3_5 domain (pfam 08460) that shares ~52% identity with the SH3b domains of PlyP56 and PlyN74. The endolysin polypeptide(s) of the present invention may be isolated from bacteriophages (e.g., Phrodo, Nigalana, and TsarBomba bacteriophages). Alternatively, the endolysin polypeptide(s) may be prepared by recombinant or synthetic methods as well known in the art.

Nucleic acid and amino acid sequences of endolysin polypeptide(s) according to disclosed embodiments are presented below:

```
Phrodo_56 (PlyP56) DNA Sequence (SEQ ID NO: 1):
ATGGCAATGGCACTGCAGACCCTGATTGATAAAGCAAATCGCAAACTGAA

TATTAGCGGCATGCGTAAAGATGTTGCAGATCGTACCCGTGCAGTTATTA

CCCAGATGCATGCACAGGGTATCTATATTTGTGTTGCCCAGGGTTTTCGT

AGCTTTGCAGAACAGGATGCACTGTATGCGCAGGGTCGTACCAAACCGGG

TAATATTGTTACCAATGCACGTGGTGGTCAGAGCAATCATAACTATGGTG

TTGCAGTTGATCTGTGTCTGTATACCCAGGATGGTAGTGATGTTATTTGG
```

ACCGTTGAAGGCAATTTTCGTAAAGTTATTGCAGCCATGAAAGGCCAGGG

CTTTAAATGGGTGGTGATTGGGTTAGCTTTAAAGATTATCCGCACTTCG

AACTGTATGATGTTGTTGGTGGCCAGAAACCGCCTGCAGATAATGGTGGT

GCCGTTGATAATGGCGGTGGTAGCGGTGGTTCAAGTGGTGGTAGTACCGG

TGGTGGCAGCACAGGTGGCGATTATGATAGCAGCTGGTTTACCAAAGAAA

CCGGCACCTTTACCACCAATACCAGCATTAAACTGCGTACCGCACCGTTT

ACCAGTGCCGGTGTTATTGCAACCCTGCCTGCAGGTAGCGTTGTTAACTA

TAATGGTTATGGCATCGAGTATGATGGCTATGTTTGGATTCGTCAGCCTC

GTAGCAATGGCTATGGTTATCTGGCAACCGGTGAAAGCAAAGGTGGTAAA

CGTCAGAATTATTGGGGCACGTTTAAACATCATCACCATCACCATTAA

Figure 1:
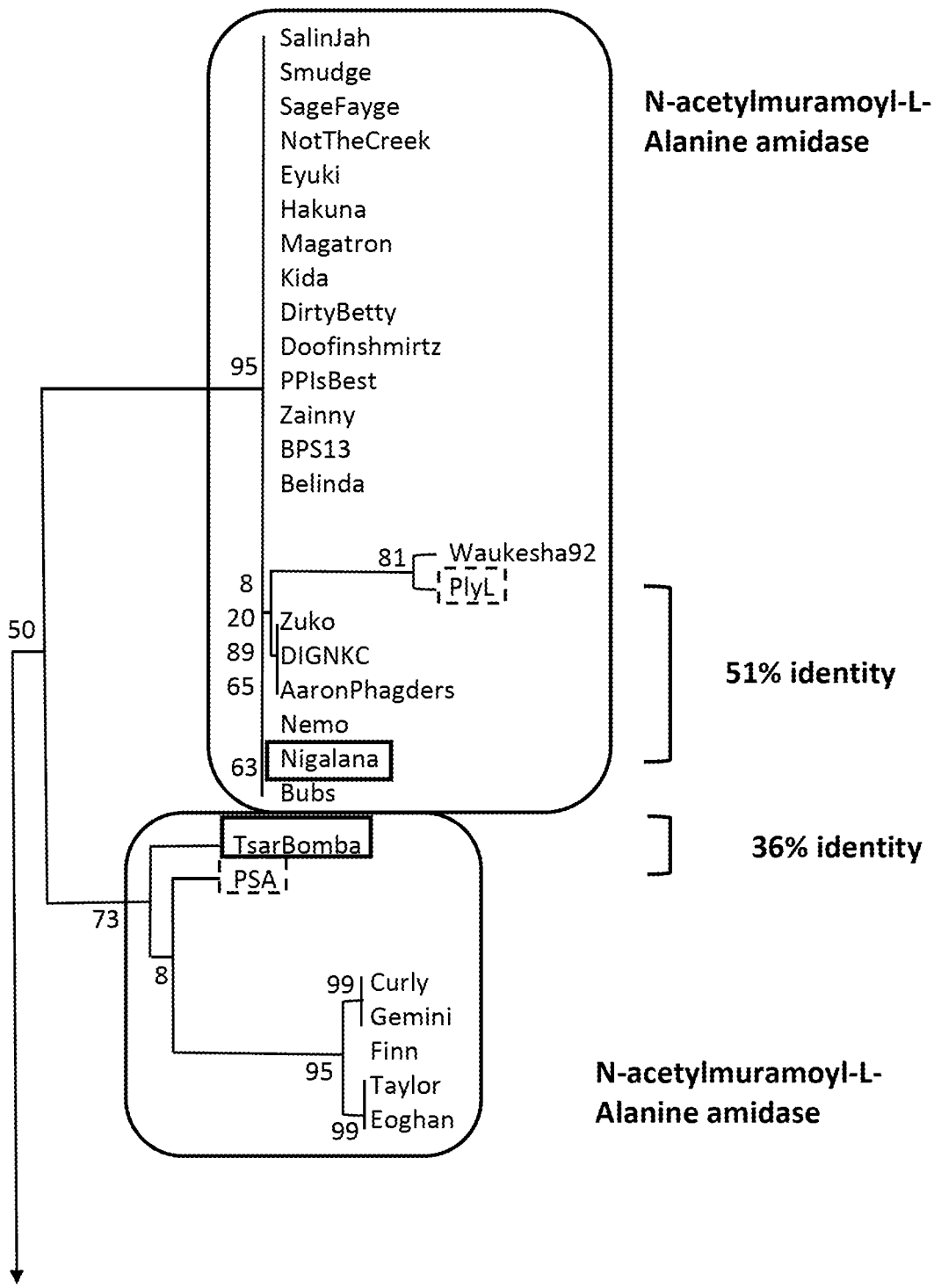
FIG. 1 illustrates schematically a molecular phylogenetic analysis of bacteriophage endolysin EADs. Sequences were obtained from *Bacillus* Phage Database (*Bacillus*.phagesdb.org) that have also been deposited into GenBank and compared to six published phage endolysin sequences. Endolysins are represented by their phage names. The evolutionary history was inferred by using the Maximum Likelihood method. The tree is drawn with branches indicating the number of substitutions per site. Endolysins tested are boxed in solid line and structurally characterized homologs are boxed in dashed line.
Figure 1:
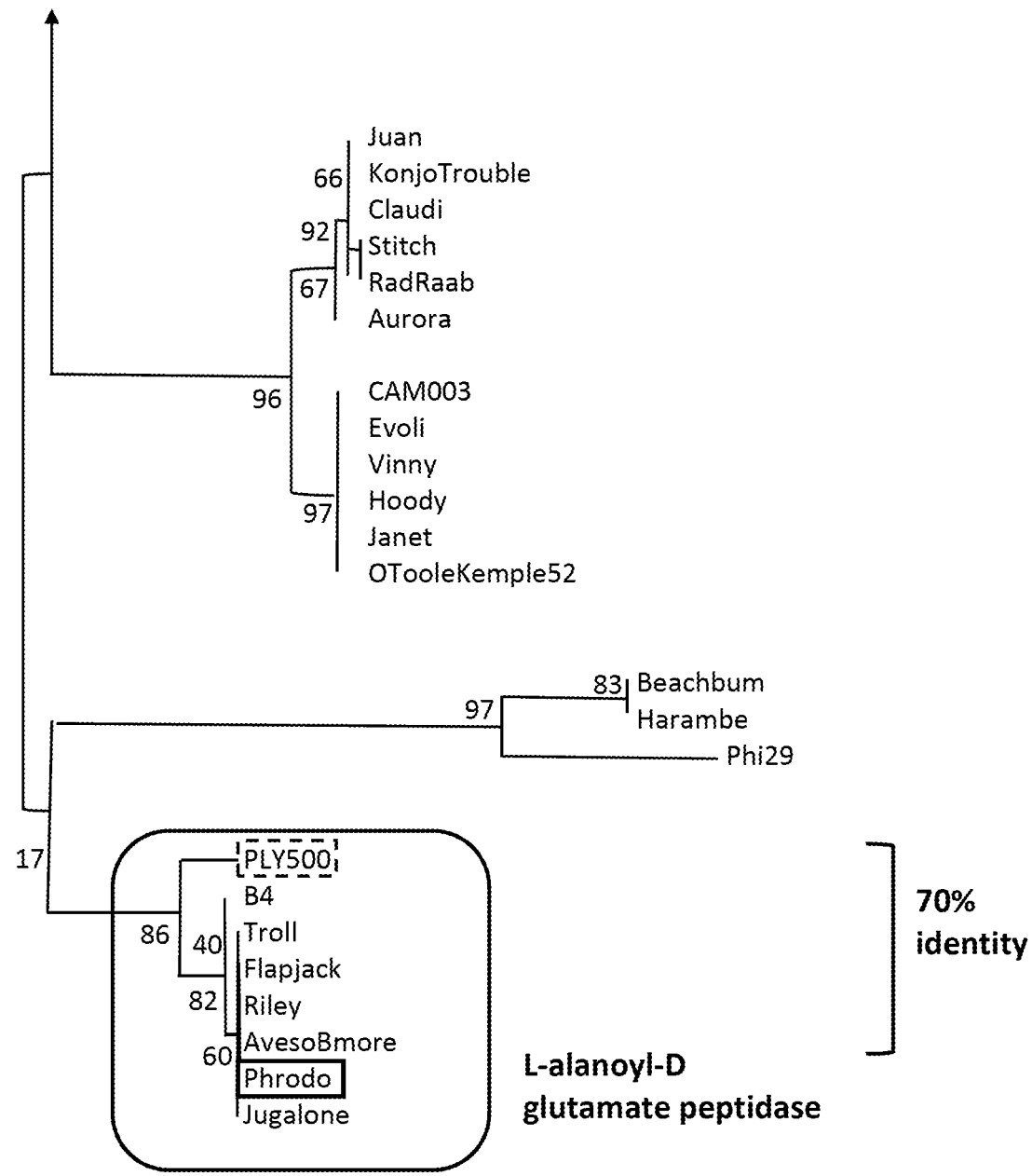

Phrodo_56 (PlyP56) Protein Sequence (amino acids
1-259; EAD and CBD underlined)(SEQ ID NO: 2):
MAMALQTLIDKANRKLNISGMRKDVADRTRAVITQMHAQGIYICVAQGFR SFAEQDALYAQGRTKPGNI<u>VTNARGGQSNHNYGVAVDLCLYTQDGSDVIW</u>

<u>TVEGNFRKVIAAMKGQGFKWGGDWVSFKDYPHFEL</u>YDVVGGQKPPADNGG

AVDNGGGSGGSSGGSTGGGSTGGDYDSSWFTK<u>ETGTFTTNTSIKLRTAPF</u>

<u>TSAGVIATLPAGSVVNYNGYGIEYDGYVWIRQPRSNGYGYLATGESKGGK</u>

<u>RQNYWGTFK</u>

Phrodo_56 (PlyP56) EAD Sequence (amino acid
residues 71-135)(SEQ ID NO: 3):
TNARGGQSNHNYGVAVDLCLYTQDGSDVIWTVEGNFRKVIAAMKGQGFKW

GGDWVSFKDYPHFEL

Phrodo_56 (PlyP56) CBD Sequence (amino acid
residues 183-247)(SEQ ID NO: 4):
ETGTFTTNTSIKLRTAPFTSAGVIATLPAGSVVNYNGYGIEYDGYVWIRQ

PRSNGYGYLATGESK

Nigalana_74 (PlyN74) DNA Sequence (SEQ ID NO: 5):
ATGAACATCAACACCCAGTATCTGGTTACCGATCCGGAACGTCTGAAAGT

TATTGGTCCGAATTGGATGAATCCGACCGAAATTACCTTTCACAACACCT

ATAATGATGCAAGCGCAAGTGCCGAAGTTCGTAATGCCGTAATAATAGC

ACCGGCACCAGCTTTCATACCGCAGTTGATGATTTTGAAGTTCAGCAGGT

TGTTCCGTTTGATCGTAATGCATGGCATGCCGGTGATGGCACCTATGGTG

CAGGTAATCGTAATAGCATTGGTGTGGAAATCTGCTATAGTATGAGCGGT

GGTGAACGTTATCGTAAAGCAGAACTGAATGCCATTGAACATATTAGCGA

TCTGATGGTGCGTTTTGGTATTCCGATTAGCAAAGTGAAAACCCATCAAG

AACGCAACGGTAAATATTGTCCGCATCGTATGCTGGATGAAGGTCGTGTT

GGTTGGTTTAAAGCCGAATGTGAACGTCGTGCAAATGAAAAACGTAATGG

TGGTGGTGGCACCCCGACACCGCCTCCGGAACCGAAACCGGAACCTACCC

CGAAACCTCCGAGCGGTGATTATGATAGCAGCTGGTTTACCAAAGAAACC

GGCACCTTTGTTACCAACACCACAATTAAACTGCGTACCGCACCGTTTAC

CTCAGCCGGTGTTATTGCAACCCTGCCTGCAGGTAGCACCGTTAACTATA

ATGGTTTTGGCATTGAGTATGATGGCTATGTGTGGATTCGTCAGCCTCGT

AGCAATGGTTATGGTTATCTGGCAACCGGTGAAAGCAAAGGTGGTAAACG

TGTGAATTATTGGGGCACCTTTAAACATCATCACCATCACCACTAA

Nigalana_74 (PlyN74) Protein Sequence (amino acids
1-275; EAD and CBD underlined)(SEQ ID NO: 6):
MNINTQYLVTDPERLKVIGPNWM<u>NPTEITFHNTYNDASASAEVRNVRNNS</u>

<u>TGTSFHTAVDDFEVQQVVPFDRNAWHAGDGTYGAGNRNSIGVEICYSMSG</u>

<u>GERYRKAELNAIEHISDLMVRFGIPISKVKTHQERNGKYCP</u>HRMLDEGRV

GWFKAECERRANEKRNGGGGTPTPPPEPKPEPTPKPPSGDYDSSWFTK<u>ET</u>

<u>GTFVTNTTIKLRTAPFTSAGVIATLPAGSTVNYNGFGIEYDGYVWIRQPR</u>

<u>SNGYGYLATGESKGGKRVNYWGTFK</u>

Nigalana_74 (PlyN74) EAD Sequence (amino acids 23-
141)(SEQ ID NO: 7):
MNPTEITFHNTYNDASASAEVRNVRNNSTGTSFHTAVDDFEVQQVVPFDR

NAWHAGDGTYGAGNRNSIGVEICYSMSGGERYRKAELNAIEHISDLMVRF

GIPISKVKTHQERNGKYCP

Nigalana_74 (PlyN74) CBD Sequence (amino acids
199-263)(SEQ ID NO: 8):
ETGTFVTNTTIKLRTAPFTSAGVIATLPAGSTVNYNGFGIEYDGYVWIRQ

PRSNGYGYLATGESK

TsarBomba_40 (PlyTB40) DNA Sequence (SEQ ID NO:
9):
ATGGGCACCTATAATGTTCATGGTGGCCATAATAGCATTGTTCAGGGTGC

AAATTATGGCAACCGTAAAGAACATGTTATGGATCGTCAGGTTAAAGATG

CCCTGATTAGCAAACTGCGTAGCCTGGGTCATACCGTTTATGATTGTACC

GATGAAACCGGTAGCACCCAGAGCGCAAATCTGCGTAATATTGTTGCAAA

ATGTAATGCCCATCGTGTGGATCTGGATATTAGCCTGCATCTGAATGCAT

ATAATGGTAGCGCAAGCGGTGTTGAAGTGTGTTATTATGATCAGCAGGCA

CTGGCAGCAAAAGTTAGCAAACAGCTGAGTGATGATATTGGTTGGAGCAA

TCGTGGTGCAAAACCGCGTACCGATCTGTATGTTCTGAATAGCACCAGCG

CACCGGCAATTCTGATTGAACTGGGTTTTATTGATAACGAGAGCGATATG

GCCAAATGGAACGTTGATAAAATTGCCGATAGCATCTGCTATGCAATTAC

CGGTCAGCGTACCGGCAGCACCGGTGGTAGTACCGGTGGTTCAACCGGTG

GCTCTACAGGTGGTGGTGGTTATGATAGCAGCTGGTTTACACCGCAGAAT

GGTGTTTTTACCGCAAACACCACCATTAAAGTTCGTAGCGAACCGAGCGT

TAATGCAACCCATCTGCGTACCCTGTATAGCGGTGGCACCTTTACCTATA

CCAGCTTTGGTATGGAAAAAGATGGCTATGTGTGGATTAAAGGTGTTGAT

GGCACCTATGTTGCAACCGGTGAAACCAGTGATGGTAAACGTATTAGCTA

TTGGGGCACCTTTCAGCATCATCATCACCATCATTAA

TsarBomba_40 (PlyTB40) Protein Sequence (amino
acids 1-272; EAD and CBD underlined)(SEQ ID NO:
10):
MGTYNVH<u>GGHNSIVQGANYGNRKEHVMDRQVKDALISKLRSLGHTVYDCT</u>

<u>DETGSTQSANLRNIVAKCNAHRVDLDISLHLNAYNGSASGVEVCYYDQQA</u>

<u>LAAKVSKQLSDDIGWSNRGAKPRTDLYVLNSTSAPAILIELGFIDNESDM</u>

<u>AKWNVDKIADSICYAITGQRTGSTGGSTGGSTGGGGYDSSW</u><u>FTPQN</u>

<u>GVFTANTTIKVRSEPSVNATHLRTLYSGGTFTYTSFGMEKDGYVWIKGVD</u>

<u>GTYVATGETSDGKRISYWGTFQ</u>

TsarBomba_40 (PlyTB40) EAD Sequence (amino acids
9-167)(SEQ ID NO: 11):
GHNSIVQGANYGNRKEHVMDRQVKDALISKLRSLGHTVYDCTDETGSTQS

ANLRNIVAKCNAHRVDLDISLHLNAYNGSASGVEVCYYDQQALAAKVSKQ

LSDDIGWSNRGAKPRTDLYVLNSTSAPAILIELGFIDNESDMAKWNVDKI

ADSICYAIT

TsarBomba_40 (PlyTB40) CBD Sequence (amino acids
195-250)(SEQ ID NO: 12):
WFTPQNGVFTANTTIKVRSEPSVNATHLRTLYSGGTFTYTSFGMEKDGYV

WIKGVD

Angel_92 (Ply A92) DNA Sequence (SEQ ID NO: 13):
ATGACCATGTATTACTATGAGCGCAACCTGAAAAACATTAATCAGCTGGC

AGATAATACCAAAGCAGCAGCACTGAAACTGCTGGATTATGCCGAAAAAA

ACAAAATTGGCGTGCTGATCTATGAAACCATTCGTAGCAAAGCACAGCAG

GCACAGAATGTTAAAAATGGTGCAAGCCAGACCATGAACAGCTATCATAT

TGTTGGTCAGGCACTGGATTTTGTTTATACCGGTGGTTATGATAAAAGCA

GCACCCTGTGGAATGGCTATGAAAAACCGGAAGCCAAAAAATTCATTGCC

TATGCAAAACAGCTGGGCTTTAAATGGGGTGGTGATTGGAGCAAATTTGT

GGATAAACCGCATCTGGAATTTCCGTATAAAGGTTATGGCACCGATACCT

TTGGTAAAAAGCCGCACCGGTTAAAACCGGCACCGCAACCAAACCGGCA

AAAACTCCGGCAAAACCGAAACCGAGCACCAGCAAAAGCAAATATAACCT

GCCGAGCGGTATCTATAAAGTTAAAACACCGCTGATGAAAGGCAGCGCAG

TTAAAGCAATTCAAGAAGCACTGGCAAGCATCTATTTCTATCCGGAAAAA

GGTGCCAAAAACAATGGCATCGATGGTTATTATGGTCCGAAAACCGCAGA

TGCAGTTAAACGTTTTCAGAGCGTTAGCGGTCTGCCTGCAGATGGTATTT

ATGGCCCTAAAACCAAAGAAGCCATCGAAAAAAAACTGAAACATCACCAT

CACCACCATTAA

Angel_92 (PlyA92) Protein Sequence (amino acids 1-
247; EAD and CBD underlined)(SEQ ID NO: 14):
MTMYYYERNLKNINQLADNTKAAALKLLDYAEKNKIGVLIYETIRSKAQQ

AQNVKNGASQTMNSYHIVGQALDFVYTGGYDKSSTLWNGYEKPEAKKFIA

YAKQLGFKWGGDWSKFVDKPHLEFPYKGYGTDTFGKKAAPVKTGTATKPA

KTPAKPKPSTSKSKYNLPSGIYKVKTPLMKGSAVKAIQEALASIYFYPEK

GAKNNGIDYYGPKTADAVKRFQSVSGLPADGIYGPKTKEAIEKKLK

Angel_92 (PlyA92) EAD Sequence (amino acids 13-
115)(SEQ ID NO: 15):
INQLADNTKAAALKLLDYAEKNKIGVLIYETIRSKAQQAQNVKNGASQTM

NSYHIVGQALDFVYTGGYDKSSTLWNGYEKPEAKKFIAYAKQLGFKWGGD

WSK

Angel_92 (PlyA92) CBD Sequence (amino acids 180-
242)(SEQ ID NO: 16):
KGSAVKAIQEALASIYFYPEKGAKNNGIDYYGPKTADAVKRFQSVSGLP

ADGIYGPKTKEAI

Pegasus_108 (PlyP108) DNA Sequence (SEQ ID NO:
17):
ATGGGTGCACCGTTTACCCTGCAAGAACTGATTGATAAAAGCAATAAACG

TCTGGGTGTTAGCGGTCTGAATAAAGTTGTTTATGAAAGCGCCATCGAAG

TGATCAAACGTGCATATAAAGAAGGCATCTGGGTTCAGTATAGCGCAGGT

TATCGTAGCTATGCAGAACAGAATGCACTGTATGCACAGGGTCGTACCAA

ACCGGGTAGCATTGTTACCAATGCACGTGGTGGTTATAGCAATCATAATT

TTGGTCTGGCCGTGGACTATTTCCTGTATGATGATAATGGTAAAGCCCAC

TGGAATGTGAATAGCGATTGGAAACGTGTTGCACAGATTGCAAAAGATCT

GGGTTTTGAATGGGGTGGTGATTGGAAATCATTTTATGATGCACCGCATC

TGGAAATGACCGGTGGTCTGAGCACCGCACAGCTGCGTGCAGGTAAACGT

CCGAAACTGGTTAGCAAAGTTAAAAATCCGGTGAGCAAACCGAGCACCAG

CAGCAGCAGTAGCGGTAGCAGCAAAAAAAACTATCTGAGCAAAGGTGATA

ATAGCAGCGCAGTTAAAACCATGCAAGAAAAACTGAATGCAGCCGGTTTT

AGCGTTGGTAAAGCAGATGGTATTTTTGGTGCAAAAACCGAAAGCGCACT

GAAAGCATTTCAGAAAAGCGTGGGTATTAGCGCAGATGGTCTGTATGGTC

CGACCAGCAAAGCAAAACTGGAAAGCTACAAAAAACCGTCCAGCTCCAAA

AAAAGCAAAGGCACCATTGTTCTGCCGAAAGGTGTTGTTAGCAGCGGTAG

CTCACATAGCGATATCAAAAATGTGCAGACCGCAACCAGCGCACTGTATT

TTTACCCGGATAAAGGTGCCAAAAACAATGGCATTGATGGTTATTGGGGT

CCGAAAACCCAGGATGCAATTCGTCGTTATCAGAGCACCAAAAGTGGTCT

GAAAACCGATGGCATCTATGGTCCGGCAACCCGTAAAGCACTGGAAAAAG

ACCTGAAAGAAGCAGGCTATACCGTTAAACATCATCACCATCACCACTAA

Pegasus_108 (PlyP108) Protein Sequence (amino
acids 1-343; EAD and CBDs underlined)(SEQ ID NO:
18):
MGAPFTLQELIDKSNKRLGVSGLNKVVYESAIEVIKRAYKEGIWVQYSAG

YRSYAEQNALYAQGRTKPGSIVTNARGGYSNHNFGLAVDYFLYDDNGKAH

WNVNSDWKRVAQIAKDLGFEWGGDWKSFYDAPHLEMTGGLSTAQLRAGKR

PKLVSKVKNPVSKPSTSSSSSGSSKKNYLSKGDNSSAVKTMQEKLNAAGF

SVGKADGIFGAKTESALKAFQKSVGISADGLYGPTSKAKLESYKKPSSSK

KSKGTIVLPKGVVSSGSSHSDIKNVQTATSALYFYPDKGAKNNGIDYYWG

PKTQDAIRRYQSTKSGLKTDGIYGPATRKALEKDLKEAGYTVK

Pegasus_108 (PlyP108) EAD Sequence (amino acids
21-128)(SEQ ID NO: 19):
SGLNKVVYESAIEVIKRAYKEGIWVQYSAGYRSYAEQNALYAQGRTKPGS

IVTNARGGYSNHNFGLAVDYFLYDDNGKAHWNVNSDWKRVAQIAKDLGFE

WGGDWKSF

Pegasus_108 (PlyP108) CBD #1 Sequence (amino acids
184-240)(SEQ ID NO: 20):
NSSAVKTMQEKLNAAGFSVGKADGIFGAKTESALKAFQKSVGISADGLYG

PTSKAKL

Pegasus_108 (PlyP108) CBD #2 Sequence (amino acids
268-341)(SEQ ID NO: 21):
SHSDIKNVQTATSALYFYPDKGAKNNGIDYYWGPKTQDAIRRYQSTKSGLK

TDGIYGPATRKALEKDLKEAGYT

Stitch_31 (PlyS31) DNA Sequence (SEQ ID NO: 22):
ATGGGCAACATTGTGGATATCAGCAAATGGAATGGTGATATCAATTGGA

TACCGCCAAACCGTATATCGATTTTATCATTGCACGTGTTCAGGATGGTA

GCAATTATCGTGATCCGCGTTATAATGGTTATGTGGCAGATATGAAACGC

AAAGGTATTCCGTTTGGCAATTATGCCTTTTGCCGTTTTGTGAGCATTAA

CGATGCAAAAAAGAAGCCCAGGATTTTTGGGATCGTGGTGATAAAAGCA

GCACCGTTTGGGTTGCAGATGTTGAAGTTAAAACCATGGATGATATGCGT

GCAGGCACCCAGGCATTTATTGATGAACTGCGTCGTCTGGGTGCCAAAAA

AGTTGGTCTGTATGTTGGTCATCACATGTATGAAAGCTTTGGTATGAGCC

AGGTTCAGAGCGATTTTGTTTGGATTCCTCGTTATGGTGGTAGCAAACCG

AAATATCCGTGTGATATTTGGCAGTATACCGAAACCGGTCATACACCGGG

TATTGGTAAATGTGATCTGAACCAGCTGATTGGCAGCAAAAATCTGGCAT

ATTTTACCGGTCAGGATGATCAGACCCCGAAAGGTTATCAGTATGTTCGT

AGCGGTGGTCTGGGTAGCAGCCTGATTAAAGAAGTTAGCATCAAAATGAA

CGAACTGGGCATTAAAGGTCGCATTATTCTGAATCCGAGCGAAGGTCTGG

CATTTATGCAGACCGATGTTCTGCCGAATGGTGAACTGGATAAAATCACC

AGTTGGTTCGATGAAAAGGTTGGTGGTATGAATATATCCAGGGTCATCA

TCATCACCATCATTAA

Stitch_31 (PlyS31) Protein Sequence (amino acids
1-265; EAD and CBD underlined)(SEQ ID NO: 23):
MGNIVDISKWNGDINWDTAKPYIDFIIARVQDGSNYRDPRYNGYVADMKR

KGIPFGNYAFCRFVSINDAKKEAQDFWDRGDKSSTVWVADVEVKTMDDMR

AGTQAFIDELRRLGAKKVGLYVGHHMYESFGMSQVQSDFVWIPRYGGSKP

KYPCDIWQYTETGHTPGIGKCDLNQLIGSKNLAYFTGQDDQTPKGYQYVR

SGGLGSSLIKEVSIKMNELGIKGRIILNPSEGLAFMQTDVLPNGELDKIT

SWFDEKGWWYEYIQG

Stitch_31 (PlyS31) EAD Sequence (amino acids 5-
168)(SEQ ID NO: 24):
VDISKWNGDINWDTAKPYIDFIIARVQDGSNYRDPRYNGYVADMKRKGIP

FGNYAFCRFVSINDAKKEAQDFWDRGDKSSTVWVADVEVKTMDDMRAGTQ

AFIDELRRLGAKKVGLYVGHHMYESFGMSQVQSDFVWIPRYGGSKPKYPC

DIWQYTETGHTPGI

Stitch_31 (PlyS31) CBD Sequence (amino acids 218-
262)(SEQ ID NO: 25):
ELGIKGRIILNPSEGLAFMQTDVLPNGELDKITSWFDEKGWWYEY Taylor_31 (PlyT31) DNA Sequence (SEQ ID NO: 26):
ATGAAAAAAGTTACCCTGGATGCAGGTCATGGTGGTAAAGATCCGGGTGC

AGTTGGTAATGGTCTGAAAGAAAAAGATCTGACCCTGGAAATTGCCAAAC

AGACCAAAAGCTATCTGGAAAGCAATTATAGCGGTGTTAGCGTTCAGCTG

ACCCGTAGCACCGATAAATTTCTGGAACTGCCGGAACGTGCAGCAATTGC

CAATAAAAACAAAAGCGACCTGTTTGTGAGCATCCATATTAACAGTGCCG

GTGGCACCAATGGCACCGGTTTTGAAACCCTGACCTATAACAAACTGAGC

GCAAAAAGCCCGACCAAAAGTGATCAGAAAGTTCTGCATGCAAGCATCCT

GAATGAAATTGCAAGCTTTGGTGTTGCCAACCGTAAAGAAAAGCAGACG

ATCTGAGCGTTCTGCGTAATACCAATATGAGCGCAATTCTGACCGAAAGC

CTGTTTATTAACAATCCGGCAGATGCAAAACTGCTGAAAGATAAATCATT

TGTGAAAGCCGTTAGCGTGGGTCATGCAAAAGGTATTGCAAAAGTTCTGG

GCCTGAAAGCAAAAAAAGCACCGGAAAGTCCGGTTAAAGCACCGAGCAAA

CCGAGCACCCCGAAAGGTGATACCTATAAAGTTCAGAAAGGCGATACCCT

GTATGGTATTGCACGTCAGCATGGTATGAGCGTTGATGATCTGAAAAAAC

TGAATGGCCTGAAAAGCGATATTATTCGTGTTGGTCAGACCCTGAAAGTT

AAACAGAGCAGCGTTACGTATAAAGTGAAAAAAGGTGACACGCTGTACGG

CATTGCCAAAGATCATGGCACCACCGTTGCAAATATCAAAAAACTGAACA

ATCTGAAATCCGACCTGATCAATATTGGTGATACCCTGCGTGTTAAACAT

CATCATCACCATCACTAA

Taylor_31 (PlyT31) Protein Sequence (amino acids
1-299; EAD and CBD underlined)(SEQ ID NO: 27):
MKKVTLDAGHGGKDPGAVGNGLKEKDLTLEIAKQTKSYLESNYSGVSVQL

TRSTDKFLELPERAAIANKNKSDLFVSIHINSAGGTNGTGFETLTYNKLS

AKSPTKSDQKVLHASILNEIASFGVANRKEKADDLSVLRNTNMSAILTES

LFINNPADAKLLKDKSFVKAVSVGHAKGIAKVLGLKAKKAPESPVKAPSK

PSTPKGDTYKVQKGDTLYGIARQHGMSVDDLKKLNGLKSDIIRVGQTLKV

KQSSVTYKVKKGDTLYGIAKDHGTTVANIKKLNNLKSDLINIGDTLRVK

Taylor_31 (PlyT31) EAD Sequence (amino acids 64-
180)(SEQ ID NO: 28):
AAIANKNKSDLFVSIHINSAGGTNGTGFETLTYNKLSAKSPTKSDQKVLH

ASILNEIASFGVANRKEKADDLSVLRNTNMSAILTESLFINNPADAKLLK

DKSFVKAVSVGHAKGIA

Taylor_31 (PlyT31) CBD #1 Sequence (amino acids
208-251)(SEQ ID NO: 29):
TYKVQKGDTLYGIARQHGMSVDDLKKLNGLKSDIIRVGQTLKVK Taylor_31 (PlyT31) CBD #2 Sequence (amino acids
256-299)(SEQ ID NO: 30):
TYKVKKGDTLYGIAKDHGTTVANIKKLNNLKSDLINIGDTLRVK Vinny_63 (PlyV63) DNA Sequence (SEQ ID NO: 31):
ATGGCACTGGAAGCAAACAAATACCCGAAAGAAAAACCATCGTGGATAT

CAGCCATCATAACGCCGATATTGATTTTGATACCGCCAAAACTATGTGA

GCATGTTTATTGCACGTACCGGTGATGGTCATCGTTATAATAGCAATGGT

GAACTGCAGGGTGTTGTGGATCGTAAATACAAAACCTTTGTGGCCAATAT

GAAAGCACGTGGTATTCCGTTTGGCAACTATATGTTTAATCGTTTTAGCG

GTGTTGCCAGCGCAAAACAAGAAGCAGAATTTTTCTGGAACTATGGCGAT

AAAGATGCAACCGTTTGGGTTTGTGATGCAGAAGTTAGCACCGCACCGAA

CATGAAAGAATGTATTCAGGTGTTTATCGATCGCCTGAAAGAACTGGGTG

CAAAAAAGTTGGTCTGTACATCGGTCACCACAAATATCAAGAATTTGGT

GGCAAAGATGTGAACTGCGATTTCACCTGGATTCCGCGTTATGGTAATAA

ACCGGCATTTGCATGTGATCTGTGGCAGTGGACCGAATATGGTAACATTG

CAGGTATTGGCAAATGCGATATTAATGTGCTGTATGGTGACAAACCGATG

AGCTTTTTACCGAAAAGAAGGTGCCAAAGAAACCCTGGTTCCGGCACT

GAATAAAGTTGTTACCTATGAAGTTGGCACCAACCTGATTCCGGAAATTC

AGGATAAACTGGCCTTTCTGGGTTATGAAGCACGTATTAACTTTACCGGT

CTGGGTGATGGCCTGGTTAGCATTGAAACCAGCCATCAGGTGGGTGCAGA

ACTGGACAAACTGACCGCATGGCTGGATGAACGTGGTTGGGCATATTACT

```
ATACCAGCAGCAAAGAAGGCTATAACGGTAAAAGCAAAGTGGTGACCTAT

GATATGGGCACAAACAAAATTCCGGAACTGAGCAATGTTCTGGCATATCA

GGGTATGCAGACCGCAATTGTTTTTACCGGCAAAGGTGATGGACTGATTC

GTCTGGAAAGCACCCCTCTGGATGAAAGCCGTCTGCAGAACTTTAAAAAC

ATTCTGGAAGCACAGAAAATCGCCTACTATATGTATAGCGAACATCATCA

CCATCATCATTAA

Vinny_63 (PlyV63) Protein Sequence (amino acids 1-
364; EAD and CBD underlined)(SEQ ID NO: 32):
MALEANKYPKEKTIVDISHHNADIDFDTAKNYVSMFIARTGDGHRYNSNG

ELQGVVDRKYKTFVANMKARGIPFGNYMFNRFSGVASAKQEAEFFWNYGD

KDATVWVCDAEVSTAPNMKECIQVFIDRLKELGAKKVGLYIGHHKYQEFG

GKDVNCDFTWIPRYGNKPAFACDLWQWTEYGNIAGIGKCDINVLYGDKPM

SFFTEKEGAKETLVPALNKVVTYEVGTNLIPEIQDKLAFLGYEARINFTG

LGDGLVSIETSHQVGAELDKLTAWLDERGWAYYYTSSKEGYNGKSKVVTY

DMGTNKIPELSNVLAYQGMQTAIVFTGKGDGLIRLESTPLDESRLQNFKN

ILEAQKIAYYMYSE

Vinny_63 (PlyV63) EAD Sequence (amino acids 15-
186)(SEQ ID NO: 33):
VDISHHNADIDFDTAKNYVSMFIARTGDGHRYNSNGELQGVVDRKYKTFV

ANMKARGIPFGNYMFNRFSGVASAKQEAEFFWNYGDKDATVWVCDAEVST

APNMKECIQVFIDRLKELGAKKVGLYIGHHKYQEFGGKDVNCDFTWIPRY

GNKPAFACDLWQWTEYGNIAGI

Vinny_63 (PlyV63) CBD Sequence (amino acids 240-
284)(SEQ ID NO: 34):
LGYEARINFTGLGDGLVSIETSHQVGAELDKLTAWLDERGWAYYY Waukesha_68 (PlyW68) DNA Sequence (SEQ ID NO: 35):
ATGGAAATCCGCAAAAATCTGGTTGATGCAAGCAAATATGGCACCAAATG

TCCGTATACCATGAACCCGGAATTTATCACCGTTCACAATACCTATAATG

ATGCCACCGCCAATAATGAAGTGGCCTATATGATTCGCAATGATAACCAG

GTGAGCTTTCATATTGCCGTGGATGATAAAGAAGCAGTTCAGGGTATTCC

GCTGGAACGTAATGCATGGCATTGTGGTGATGGTGGTGGTAATGGTAATC

GTAAAAGCATTGGTGTGGAAATCTGCTATAGCCTGAGCGGTGGTGATCGT

TATTACAAAGCCGAAGATAATGCAGCAATTGTTGTTGCAGGTCTGATGAA

ACAGTATAACATTCCGATTAGCAAAGTGCGTACCCATCAGAGCTGGTCAG

GTAAATATTGTCCGCATCGTATGCTGGCAGAAGGTCGTTGGAATAGCTTT

ATTGAACGTGTTCAGAATGCGTATAATGGTGGCGGTAGTCCGGTTATGCC

GACCCCGATTCCGCCTAGCAATGATGGTACAAAAGTTGCCTATATTAACG

GCGATAATGTGAATCTGCGTAAAGGTACAGGTTATGCGGTTATTCGTAAA

CTGGGTAAAGGTGAATGTTATCAGGTTTGGGGTGAAAGCAATGGTTGGCT

GAATCTGGGTGGCGATCAGTGGGTTTATAATGATAGCAGCTATATTCGCT

ATACCGGTGAAAATGCACCGGCACCGAGCAAACCGTCAAACGATGGTATT

GGTGTTGTGACCATTACCGCAGATGTTCTGCGTGTTCGTACCGGCACCAA

TTATGGTGTTGTTAAAAATGTGTATCAGAGCGAACGTTATCAGTCATGGG

GTTATCGTGATGGTTGGTATAATGTTGGAGGTGATCAATGGGTTAGCGGT

GAATATGTGAAATTTGAAAAACATCATCATCACCATCATTAA

Waukesha_68 (PlyW68) Protein Sequence (amino acids
1-307; EAD and CBD underlined)(SEQ ID NO: 36):
MEIRKNLVDASKYGTKCPYTMNPEFITVHNTYNDATANNEVAYMIRNDNQ

VSFHIAVDDKEAVQGIPLERNAWHCGDGGGNGNRKSIGVEICYSLSGGDR

YYKAEDNAAIVVAGLMKQYNIPISKVRTHQSWSGKYCPHRMLAEGRWNSF

IERVQNAYNGGGSPVMPTPIPPSNDGTKVAYINGDNVNLRKGTGYAVIRK

LGKGECYQVWGESNGWLNLGGDQWVYNDSSYIRYTGENAPAPSKPSNDGI

GVVTITADVLRVRTGTNYGVVKNVYQSERYQSWGYRDGWYNVGGDQWVSG

EYVKFEK

Waukesha_68 (PlyW68) EAD Sequence (amino acids 13-
154)(SEQ ID NO: 37):
YGTKCPYTMNPEFITVHNTYNDATANNEVAYMIRNDNQVSFHIAVDDKEA

VQGIPLERNAWHCGDGGGNGNRKSIGVEICYSLSGGDRYYKAEDNAAIVV

AGLMKQYNIPISKVRTHQSWSGKYCPHRMLAEGRWNSFIERV

Waukesha_68 (PlyW68) CBD Sequence (amino acids
177-233)(SEQ ID NO: 38):
TKVAYINGDNVNLRKGTGYAVIRKLGKGECYQVWGESNGWLNLGGDQWVY

NDSSYIR
```

The endolysin polypeptide(s) of the present invention may be isolated from bacteriophages or prepared by recombinant or synthetic methods known in the art. The disclosed endolysin polypeptide(s) may be engineered through domain shuffling or used in combination with other endolysins, holin proteins and/or antibiotics or other therapeutic agents to prolong therapeutic efficacy (Shen Y et al.(2012) *Phage-based Enzybiotics*. In: Abedon S, Hyman P (eds) Bacteriophages in Health and Disease. CABI Press, pp 217-239). Thus, endolysin polypeptides of the present invention may be truncated, chimeric, shuffled or natural (e.g., corresponding to wild-type). A "chimeric" polypeptide may be produced by combining two or more proteins having two or more active sites. Chimeric polypeptides may act independently on the same or different molecules, and hence may potentially exhibit activity against two or more different bacterial species or antigen targets.

In accordance with some embodiments, polypeptides are prepared or engineered to exhibit amino acid sequence percent identity of at least 50%, 60%, 70%, 80%, 85% identity, and preferably at least 90%, 95%, 98% or 99% identity, with active regions of *Bacillus* bacteriophage endolysin(s) also exhibiting functionality and/or comparable therapeutic efficacy (e.g., bacterial effects) therewith. Amino acid sequence percent identity is defined as the percentage of amino acid residues in a candidate sequence that are identical with the amino acid residues in the wild-type *Bacillus* bacteriophage associated endolysin sequence, after aligning the sequences in the same reading frame and introducing gaps, if necessary, to achieve the maximum percent sequence identity, and not considering any conservative substitutions as part of the sequence identity.

Mutations can be made in the disclosed amino acid sequences, or in the nucleic acid sequences encoding the polypeptides herein, or in active fragments or truncations thereof, such that a particular codon is modified to a codon which codes for a different amino acid, an amino acid is substituted for another amino acid, or one or more amino acids are deleted. Preferably, any such mutations do not significantly alter the activity of the resulting polypeptide.

Thus, one of skill in the art, based on a review of the disclosed sequences of the *Bacillus*-specific endolysin(s) of the present invention, may implement amino acid mutations in the polypeptide sequences to identify additional variants thereof (e.g., via random mutagenesis or by a site-directed method such as polymerase chain-mediated amplification with primers that encode the mutated locus). Further, mutagenizing entire codons rather than single nucleotides results in a semi-randomized repertoire of amino acid mutations. Libraries can be constructed consisting of a pool of variants each of which differs by a single amino acid alteration and/or which contain variants representing each possible amino acid substitution for each residue. Variants may be screened for desired activity using any screening method known in the art.

Variants may include one or more amino acid mutations (e.g., 1, 1-5, 1-10, or 10 or more) in the sequence of the endolysin polypeptide(s), and also exhibit comparable functionality (e.g., comparable activity against bacteria) to the native endolysin polypeptide. Activity of such variant(s) may be tested using assays and methods as described herein and as well known in the art. One of skill in the art may predict suitable amino acid mutations to achieve such variants based on the disclosure herein.

In addition, disclosed embodiments provide for constructs comprising one or more EAD(s) from one *Bacillus* bacteriophage endolysin paired with one or more CDB(s) of another *Bacillus* bacteriophage endolysin. Thus, an EAD from one of the disclosed endolysin polypeptides may be linked with a CBD from any other disclosed endolysin polypeptide.

As discussed in further detail below, contributions of the EADs and CBDs of the disclosed *Bacillus*-specific endolysin(s) were investigated. The results herein indicate that the disclosed endolysins demonstrate efficacy as suitable therapeutic options for treating and/or preventing bacterial infection. In particular, preferred PlyP56, PlyN74 and PlyTB40 endolysin(s) were all found to exhibit strong activity against *Bacillus* species (e.g., such as *B. cereus*). Thus, the endolysin polypeptides of the present invention were demonstrated to be highly effective in killing, reducing or eliminating bacterial growth and/or population, and thus are suitable for treating or preventing bacterial infection or symptoms associated with such bacteria in a subject (e.g., a mammal, and in particular human patient).

Compositions and methods utilizing or including the endolysin polypeptide(s) of the present invention are effective in killing or treating Gram-positive bacteria in subjects, either alone or in composition with one or more additional therapeutic agents, such as an antimicrobial, an antibiotic (e.g., including but not limited to, a penicillin, a cephalosporin, a polymyxin, an ansamycin, a quinolone, a sulfonamide, a lipopeptide, a glycycline, and an oxazolidinone), and/or an anti-inflammatory agent. In some implementations, compositions or methods of treatment provide for the use of the disclosed *Bacillus*-specific endolysin(s) in combination with one or more antibiotic(s) selected from linezolid, daptomycin, tigecycline, vancomycin, fidaxomicin, and/or metronidazole. In some implementations, the endolysin polypeptide(s) of the present invention, or therapeutically active variants thereof, are covalently attached to an agent that provides additional functionality or enhances efficacy thereof. Such agent(s) includes, for example, a tag, label, targeting moiety or ligand, a cell binding motif or therapeutic agent, an antibacterial, an antibody, and an antibiotic.

In some embodiments, compositions or methods of treatment provide for the use of the disclosed *Bacillus*-specific endolysin(s) in combination with a holin protein(s). Holin proteins produce holes or lesions in the cell membrane. As known in the art, holin proteins are coded for and carried by a phage. Holins may fall into one of two general classes based on primary structure analysis. Class I holins are typically about 95 residues or longer and may have three potential transmembrane domains. Class II holins are typically shorter, about 65-95 residues, with the distribution of charged and hydrophobic residues indicating two transmembrane domains. The holin protein(s) used in accordance with disclosed embodiments may be unaltered, chimeric, shuffled, or may be combinations thereof.

Using turbidity reduction of stationary phase *B. cereus* (ATCC 4342) as a measure of lytic activity, optimal conditions e.g. for PlyP56, PlyN74 and PlyTB40 were determined, finding that all were active in the physiological range. For example, PlyP56-induced lysis of the bacterial peptidoglycan caused a 60% decrease in optical density (O.D.) within just 4 minutes of the turbidity assay at a tested dose of 100 µg/ml. PlyN74 and PlyTB40 achieved the same degree of lysis in 15 minutes in comparable assays.

In some embodiments, the disclosed endolysin polypeptide(s) and/or compositions including the endolysin polypeptide(s) of the present invention are coupled to a surface of a substrate. For example, in some implementations, a medical device (e.g., a grasper, a clamp, a retractor, a dilator, a suction, a sealing device, a scope, a probe, etc.) includes an outer surface coupled to or coated with the endolysin polypeptide(s) or composition comprising the endolysin polypeptide(s) of the present invention. In some implementations, the medical device coupled to or coated with the disclosed endolysin polypeptide(s) or composition(s) is an implantable medical device (e.g., a drainage tube, a feeding tube, a shunt, a prosthesis, a guidance tube, a catheter, a valve, a pacemaker, a graft, a tissue scaffold, a stent, etc.).

The present invention provide for methods of treating a bacterial infection in a patient comprising administering to the patient a therapeutically effective amount of an isolated endolysin polypeptide of the present invention, and in particular a polypeptide(s) comprising the amino acid sequence of SEQ ID NO: 3, SEQ ID NO:7 and/or SEQ ID NO:11, or a polypeptide(s) comprising the amino acid sequence of SEQ ID NO:2, SEQ ID NO:6, SEQ ID NO:10, SEQ ID NO:14, SEQ ID NO:16, SEQ ID NO:18, SEQ ID NO:20, SEQ ID NO:22 and/or SEQ ID NO:24, or variants thereof such as a polypeptide(s) having at least about 80% identity thereto, more preferably at least about 90%, 92%, 94%, 95%, 98%, or 99% identity thereto, and exhibiting comparable functionality and efficacy against bacteria associated with or causing said infection. The term "treat" or "treating" a disease, including an infectious disease or infection, refers to killing or reducing the growth of the bacteria causing such disease or infection, and/or reducing, ameliorating or eliminating symptoms associated with such disease or infection.

A "therapeutically effective amount" refers to the amount of polypeptide(s) sufficient to elicit a desired biological response in a subject, and in particular an amount sufficient to kill, reduce or stabilize a bacterial population causing such disease or infection and/or sufficient to reduce symptoms associated with such disease or infection. Preferably, a therapeutically effective amount of the polypeptide(s) of the present invention is effective in reducing growth of the bacterial population by at least about 50%, more preferably by at least about 75%, most preferably by about 90%, or by about 95%, or about 99%, or more.

The present invention is also directed to expression vectors prepared from the disclosed DNA sequences for expression in host systems, and encoding one or more of the endolysin polypeptide chains of the present invention. Such expression vectors may be used for recombinant production of the disclosed endolysin polypeptides. An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40 bacterial plasmids, phage DNA, baculovirus, yeast plasmids, vectors derived from combinations of plasmids and phage DNA, and viral nucleic acid (RNA or DNA) vectors.

In one embodiment, the vector is suitable for expression of an endolysin polypeptide of the present invention in a bacterial cell. Examples of such vectors include expression vectors such as BlueScript (Stratagene), pIN vectors (Van Heeke & Schuster, J. Biol. Chem. 264, 5503-5509 (1989), pET vectors (Novagen, Madison, WI), and the like. An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (F. Ausubel et al., ed. Current Protocols in Molecular Biology, Greene Publishing and Wiley Inter-Science New York (1987); Grant et al., Methods in Enzymol 153, 516-544 (1987); Mattanovich, D. et al. Methods Mol. Biol. 824, 329-358 (2012); Celik, E. et al. Biotechnol. Adv. 30(5), 1108-1118 (2012); and Holliger, P. Methods Mol. Biol. 178, 349-357 (2002)).

In an expression vector of the present invention, nucleic acids encoding the disclosed polypeptides may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE.

Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. Any host cell capable of overexpressing heterologous DNAs can be used for the purpose of isolating the genes encoding the polypeptide or protein of interest, including for example, eukaryotic and prokaryotic hosts (e.g., strains of E. coli, Pseudomonas, Bacillus, Streptomyces, yeasts, etc.). As understood by those skilled in the art, not all vectors express control sequences and hosts will function equally well to express the DNA sequences of the present invention. However, those skilled in the art will be able to readily select the proper vectors, expression control sequences, and hosts to achieve the desired expression.

The present invention provides for nucleic acids capable of encoding the disclosed endolysin polypeptide(s). "Primer" as used herein refers to an oligonucleotide that is capable of acting as a point of initiation of synthesis when placed under suitable conditions in which synthesis of a primer extension product is induced. The primer may be either single-stranded or double-stranded and sufficiently long to prime the synthesis of the desired extension product in the presence of an inducing agent. Exemplary primers are provided in Table 1 below.

The present invention also relates to pharmaceutical compositions containing therapeutically effective amounts of the disclosed endolysin(s), EAD(s) and/or CBD(s) thereof, and/or variants and active fragments thereof. The pharmaceutical compositions may be formulated with pharmaceutically acceptable carriers or diluents as well as any other known adjuvants and excipients in accordance with conventional techniques, e.g., such as those disclosed in Remington: The Science and Practice of Pharmacy, 21th Edition, Gennaro, Ed., Mack Publishing Co., Easton, P A, 2005.

The pharmaceutically acceptable carriers or diluents, as well as any other known adjuvants and excipients, should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may thus include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in the composition. The diluent is selected to not affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredient(s) in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known to those or ordinary skill in the medical arts.

The pharmaceutical compositions of the present invention may be administered by any suitable route and mode, including: parenteral, topical, oral or intranasal means for prophylactic and/or therapeutic treatment. In one embodiment, a pharmaceutical composition of the present invention is administered topically. In another embodiment, the pharmaceutical composition of the present invention is administered orally. In another embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. Additional suitable routes of administering a compound of the present invention in vivo and in vitro are well known in the art and may be selected by those of ordinary skill in the art.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts and may alternatively or additionally be included.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Pharmaceutical compositions of the present invention may also comprise isotonicity agents, such as sugars, polyalcohols, such as mannitol, sorbitol, glycerol or sodium chloride in the compositions.

Pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition.

The pharmaceutical compositions of the present invention may include a secondary therapeutic agent in addition to therapeutically effective amounts of the endolysin polypeptides or active fragments thereof disclosed herein, such as for example an additional antimicrobial, antibiotic, and/or lytic enzyme.

The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. The compositions of the present invention may also include a carrier or vehicle for delivery of the endolysin(s) and/or other agents to an infection. In some embodiments, the carrier has a selected pH, e.g., in a range of about 4.0 and about 9.0, more preferably in a range of about 6.0 and about 8.0, for example about 7.4. Methods for the preparation of such formulations are generally known to those skilled in the art. See, e.g., *Sustained and Controlled Release Drug Delivery Systems*, J. R. Robinson, ed., Marcel Dekker, Inc., New York, 1978.

In one embodiment, the compounds of the present invention may be formulated to ensure proper distribution and efficacy in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound(s), use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In some cases, it will be preferable to include isotonic agents, for example, sugars, polyalcohols such as glycerol, mannitol, sorbitol, or sodium chloride in the composition. Prolonged absorption of the compositions may be brought about by including in the composition an agent that delays absorption, for example, monostearate salts and gelatin. Sterile solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses are adjusted to provide the optimum desired response (e.g., a therapeutic response). For example, a single bolus may be administered, several divided doses may be administered over time, or the dose may be proportionally reduced or increased as indicated by the exigencies of the therapeutic situation. Pharmaceutical compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and dependent on (a) the characteristics of the active compound and the particular therapeutic effect to be achieved, and (b) any limitations in the art of compounding such an active compound for the treatment of sensitivity in individuals.

A physician having ordinary skill in the art may readily determine and prescribe the therapeutically effective amount of the pharmaceutical composition required for a particular patient. Such amount may vary according to factors such as the disease state, age, sex, and weight of the patient. In addition, the therapeutically effective amount is one in which any toxic or detrimental effects of the pharmaceutical composition are outweighed by the therapeutically beneficial effects. The physician may start doses of the endolysin polypeptide(s) in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce the desired therapeutic effect (e.g., killing gram-positive bacteria, and in particular *Bacillus* species, e.g., *B. cereus*, and/or for treating or preventing infection, and/or for ameliorating or alleviating symptoms associated with such bacteria in a subject). Such an effective dose will generally depend upon the factors described above. While it is possible for a compound of the present invention to be administered alone, it is preferable to administer the compound as a pharmaceutical composition as described above.

Pharmaceutical compositions in accordance with the present invention may be administered via spray, inhaler, topical, etc. Pharmaceutical compositions and polypeptides in accordance with disclosed embodiments may be administered via lozenges, chewing gums, tablets, powders, sprays, liquids, ointments, etc. Formulations including endolysin polypeptides of the present invention may include additives, stabilizers, buffers, etc. as described above.

While some embodiments are described with respect to use in humans, the endolysin polypeptides, compositions and methods of the present invention are also suitable for veterinary (non-human) applications, such as for treating and/or preventing infection in grazing animals including livestock, and/or for treating and/or preventing infection or contamination in feed and equipment used for or associated with animals. Thus, the polypeptide(s) of the present invention may be utilized for treating or preventing bacterial infection in livestock or other animals (e.g., by administering the polypeptide(s) of the present invention to such livestock or animal orally, nasally, parenterally, onto the skin or coat, via intramammary infusion, teat dip, etc. as described herein), as well for treating or preventing contamination in facilities and/or equipment associated with livestock or other animals.

The endolysin polypeptides of the present invention, and compositions comprising such polypeptides, are also suitable for use as a sanitizing agent or disinfectant of a target surface or area. Thus, the present invention provides for methods and compositions for treating or preventing bacterial contamination of dental and medical devices, surfaces in hospitals and dental and medical facilities, food processing equipment, surfaces in food processing facilities, equipment and surfaces in schools, and other equipment or surfaces on which sanitization is desired.

In addition, the compositions of the present invention may be used in combination with other disinfecting ingredients, cleaners, and agents (e.g., such as detergents, solvents, antibiotics, antimicrobials, etc.). In some implementations, the endolysin polypeptide(s) and compositions of the present invention are applied to target surfaces or areas as a liquid or spray formulation (e.g., aerosolized or mist formulation). Disclosed compositions may be applied, e.g., with a dry mist fogger or other such application, for disinfecting surfaces within a target area or volume (e.g., a milking parlor, school gymnasium or auditorium, surgical suite, medical equipment, etc.).

Additional characteristics and features of the present invention will be further understood through reference to the following examples and discussion, which are provided by way of further illustration and are not intended to be limiting of the present invention.

MATERIALS AND METHODS

Bacteriophage sequence analysis. Forty-six sequenced *Bacillus*-specific bacteriophage genomes contained in the *Bacillus* Phage Database (*Bacillus*.phagesdb.org) and GenBank were screened for putative endolysins. Each bacteriophage open reading frame (ORF) was searched with the BLASTN, BLASTP, Pfam, and CDD databases. Six published endolysin sequences (LysB4, Ply500, PlyL, PlyPSA, LysBPS13, and phi29) were added for comparison (Korndörfer, I P et al., *The crystal structure of the bacteriophage PSA endolysin reveals a unique fold responsible for specific recognition of Listeria cell walls*. Journal of Molecular Biology 2006, 364, 678-689; Korndörfer, I P et al., *Structural analysis of the L-alanoyl-D-glutamate endopeptidase domain of Listeria bacteriophage endolysin Ply500 reveals a new member of the LAS peptidase family*. Acta Crystallographica Section D: Biological Crystallography 2008, 64, 644-650; Low, L Y et al., *Structure and lytic activity of a Bacillus anthracis prophage endolysin*. Journal of Biological Chemistry 2005, 280, 35433-35439; Park, J et al., *Characterization of an endolysin, LysBPS13, from a Bacillus cereus bacteriophage*. FEMS Microbiol Lett 2012, 332 (1):76-83; Saedi, M S et al., *Cloning and purification of a unique lysozyme produced by Bacillus phage phi 29*. Proc Natl Acad Sci USA 1987, 84(4):955-8; Son, B et al., *Char-* acterization of LysB4, an endolysin from the Bacillus cereus-infecting bacteriophage B4*. BMC microbiology 2012, 12, 33).

As shown in FIG. 1, phylogenetic trees were drawn using MEGA7 (Kumar, S et al., *MEGA7: Molecular Evolutionary Genetics Analysis Version* 7.0 *for bigger datasets. Mol Biol Evol* 2016, 33(7):1870-4) to determine phylogenetic position of ORFs among *Bacillus* species-specific bacteriophages using the Maximum Likelihood method based on the JTT matrix-based model (Jones, D T et al., *The rapid generation of mutation data matrices from protein sequences*. Comput Appl Biosci 1992, 8(3):275-82). The percentage of trees in which the associated taxa clustered together is shown next to the branches. Initial tree(s) for the heuristic search were obtained automatically by applying Neighbor-Join and BioNJ algorithms to a matrix of pairwise distances estimated using a JTT model, and then selecting the topology with superior log likelihood value.

Genes encoding the *B. cereus* group-specific endolysins Phrodo ORF_56 (AMW62097.1) referred to as PlyP56, Nigalana ORF_74 (AMW61226.1) referred to as PlyN74, and TsarBomba ORF_40 (ALA13156.1) referred to as PlyTB40, were selected for expression in *Escherichia coli*.

Bacterial strains and growth conditions. *Bacillus* strains used in this study are described in Table 2. Unless otherwise described, bacterial strains were purchased from the American Type Culture Collection (ATCC). *B. anthracis* strains (both BSL2 and BSL3) were procured from the Biodefense and Emerging Infections Research Resources (BEI Resources). All BSL-3 work was performed according to the established and CDC-approved Standard Operating Procedures/Protocols (SOPs) at the BSL3 containment facility of George Mason University. All standard safety precautions were strictly followed for conduct of the studies, including use of protective personnel equipment and other personal sterile practices specifically designed for safe conduct of BSL3 work. The containment facilities at George Mason University are registered with the CDC to allow possession, use, and transfer of select agents (including *B. anthracis*) and toxins according to specified guidelines. All *Bacillus* strains were propagated overnight in Brain Heart Infusion (BHI) plates or BHI broth at 37° C. and shaken at 200 rpm. An overnight liquid culture of the main indicator strain, *B. cereus* ATCC 4342, was used for all biochemical characterization studies. To test bactericidal activity, a 1:100 dilution of overnight bacterial culture in fresh media was incubated at 37° C. and 200 rpm for 4 hours. DH5α competent and BL21 (DE3) competent *E. coli* strains were used for cloning and protein expression. *E. coli* strains were propagated overnight at 37° C. and shaken at 220 rpm unless otherwise stated. *E. coli* strains were cultured in Luria-Bertani (LB) broth (BD Biosciences), and/or on LB plates supplemented with 100 μg/ml ampicillin. All chemicals and culture media were acquired from Sigma Aldrich Corp. (St. Louis, MO) unless otherwise stated.

Cloning of vector constructs. Endolysin-encoding genes, plyP56, plyN74, and plyTB40 were codon optimized for expression in *E. coli* and chemically synthesized by ThermoFisher Scientific Inc. (Waltham, MA) in a pMA_T vector. The constructs with EcoRI and XbaI restriction sites and a C-terminal hexahistidine tag (6xHis tag) were subcloned into an arabinose-inducible pBAD24 expression vector, sequenced (Macrogen) to confirm identity, and eventually transformed into BL21 (DE3) competent *E. coli*. Ampicillin resistant colonies were expanded and once again re-tested by sequencing. The ApE software (University of Utah, USA) was utilized for DNA sequence manipulations and analysis. Alternatively, the CBDs for each endolysin, including residues 174-259 for PlyP56, 190-275 for PlyN74, and residues 191-272 for PlyTB40, were cloned identical to the procedures described above for the full-length enzymes, with the exception that the 6xHis tag was placed on the N-terminus for the CBD constructs. Primers for these constructs are identified in Table 1 below.

TABLE 1

Primers used in this study

| Purpose | Template | Primer | Sequence (5' > 3')* |
|---|---|---|---|
| Amplification of CBD and addition of N' terminal 6X HIS tag | pBAD24::plyP56 | IR29 F' | CGTGAATTCATGCATCATCATCATCATCATGATTATGATAGCAGCTGG (SEQ ID NO: 39) |
| | | IR30 R' | CGTTCTAGATTATTTAAACGTGCCCCAATA (SEQ ID NO: 40) |
| Amplification of CBD and addition of N' terminal 6X HIS tag | pBAD24::plyN74 | IR33 F' | CGTGAATTCATGCATCATCATCATCATCATGATTATGATAGCAGCTGGTTTACC (SEQ ID NO: 41) |
| | | IR34 R' | CGTTCTAGATTATTTAAAGGTGCCCCAATAATTCAC (SEQ ID NO: 42) |
| Amplification of CBD and addition of N' terminal 6X HIS tag | pBAD24::plyTB40 | IR37 F' | CGTGAATTCATGCATCATCATCATCATCATTATGATAGCAGCTGGTTTACACCG (SEQ ID NO: 43) |
| | | IR38 R' | CGTTCTAGATTACTGAAAGGTGCCCCAATAGCTAAT SEQ ID NO: 44) |

*Restriction sites underlined

Recombinant protein expression. Overnight cultures of *E. coli* strain BL21 (DE3) transformed with pBAD24 vectors containing plyP56, plyN74, or plyTB40 genes, or their corresponding CBDs, were diluted 1:100 (vol:vol) with sterile LB broth supplemented with ampicillin (100 μg/ml) and shaken at 220 rpm and 37° C. for approximately 3 hrs. Once the optical density (OD600) reached 0.8, protein expression was induced with 1-arabinose (0.25%). *E coli* cultures were returned to the shaker which was set at 180 rpm and 18° C. for overnight protein expression (~16 hrs). The following morning, bacterial cells were pelleted by centrifugation at 5,000 rpm for 10 min at 4° C. The supernatant was discarded and cell pellets were subjected to protein purification.

Recombinant protein purification. Cell pellets were resuspended in lysis buffer (phosphate buffered saline supplemented with 10 mM imidazole, pH 7.4). A protease inhibitor, phenylmethylsulfonyl fluoride (PMSF), in a final concentration of 1 mM, was added to cell lysate before sonication. After sonication, cell debris was removed by centrifugation at 12,000 rpm for 45 min at 4° C. The supernatant containing soluble protein was filtered with a 0.45 mm filter (Whatman) and recombinant proteins were applied to MINI PROFINITY™ IMAC Cartridges (Bio-Rad) and eluted in 10 ml fractions of 20, 50, 100, 250, and 500 mM imidazole. Proteins were analyzed by SDS-polyacrylamide gel electrophoresis (SDS-PAGE) for purity. Fractions containing homologous recombinant proteins were pooled and dialyzed overnight against PBS (pH 7.4) supplemented with 300 mM NaCl. Protein concentrations were determined by the Bradford assay following manufacturer's instructions (Bio Rad). Purified proteins were stored at −80° C. in PBS (pH 7.4) supplemented with 15% glycerol.

Turbidity reduction assay. Bacteriolytic activity of endolysins was measured via the turbidity reduction assay as described (Nelson, D C et al., *Endolysins as antimicrobials. Adv Virus Res* 2012, 83, 299-365). The assay was performed in a standard 96-well titration plate (Thermo Fisher Scientific) with an overnight bacterial culture of indicator strain, *B. cereus* ATCC 4342, for all dose range and biochemical characterization studies. For all host range studies, a 4-hr culture of mid-log bacteria was used. A change in OD600 was measured every 15 sec over the duration of the assay (20 min) on a SPECTRAMAX® 190 spectrophotometer (Molecular Devices). Briefly, bacterial cells were pelleted at 5,000 rpm for 10 min at 4° C. and resuspended in sterile PBS. A 100 µl volume of cell suspension was added to each well containing 100 µl of each endolysin at a predetermined concentration range such that the starting OD600 was equal to 1.0. Wells with a mixture of only bacteria in PBS served as a negative control and established a settling baseline that was subtracted from the experimental data. Bacteriolysis was quantified as the percentage of activity relative to the lytic activity of 100 µg/ml PlyP56 on *B. cereus* ATCC 4342, which represented 100% activity for all dose range analysis, and at 50 µg/ml of PlyP56 (100% activity), for all biochemical characterization studies. All experiments were performed in triplicate on three consecutive days.

Plate lysis (spot) assay. In addition to the turbidity reduction assays, *B. cereus* ATCC 4342 and *B. anthracis* strains were assayed via plate lysis assay. Briefly, bacterial cells were harvested and pelleted at their mid-log phase (4-hr cultures). Pellets were then washed twice in PBS, resuspended in 12 ml of 0.7% semisolid agar cooled to 50° C., poured onto square 10-cm petri dishes, and gently tilted to cover the bottom of the dish. Endolysins were serial diluted 10-fold in PBS to make the concentrations 1 mg/ml, 0.1 mg/ml, and 0.01 mg/ml. Spots (10 µl) were made across a row for 10 µg, 1 µg, 0.1 µg endolysin, and PBS with no endolysin served as a buffer control. Plates were dried in a biosafety hood for 15-20 minutes and incubated face up at 37° C. for 2 hours. Clearing zones were assessed at 1 hr and 2 hrs post-spotting.

Characterization of PlyP56, PlyN74, and PlyTB40. The turbidity reduction assays described above were used to determine the optimal lytic conditions. For dose-response studies, endolysins were serially diluted beginning with a starting concentration of 100 µg/ml. To evaluate enzymatic activity over a pH range of 3.0 to 11.0, bacterial cells were diluted in equal volumes of universal pH buffer (40 mM boric acid and 40 mM phosphoric acid (BP) buffer adjusted to the desired pH with NaOH), and were challenged against each endolysin at a final concentration of 50 µg/ml. The influence of NaCl on lytic activity of endolysins at 50 µg/ml was tested in BP buffer at pH 7.4 supplemented with increasing concentrations of NaCl (0-500 mM). Kinetic stability of endolysins was evaluated as described by Son, B et al., *Characterization of LysB4, an endolysin from the Bacillus cereus-infecting bacteriophage B4. BMC microbiology* 2012, 12, 33, with minor modifications. Briefly, endolysins were incubated at indicated temperatures (4° C., 25° C., 37° C., 45° C., 55° C., or 60° C.) for 30 minutes, recovered on ice for 5 minutes, and subjected to the turbidity reduction assay at previously determined optimal conditions (pH, NaCl) for each endolysin. To evaluate the role of divalent cations in catalytic function, endolysins were dialyzed overnight at 4° C. in Tris-EDTA buffer (20 mM Tris, 20 mM NaCl, 5 mM EDTA, pH 7.4) to remove any residual metal ions. Subsequently, one half of the EDTA-treated endolysins was stored overnight at 4° C. and the second half was dialyzed overnight in Tris-buffered saline (TBS) (pH 7.4) supplemented with 6 mM CaCl2) or 6 mM MgCl2. Lysis of *B. cereus* ATCC 4342 was assayed via turbidity assay and untreated endolysins served as a control.

Spectrum of lytic activity. The host-range of the endolysins was accessed via turbidity reduction assay. Overnight cultures of all bacilli were diluted 1:100 and incubated an additional 4 hr in fresh media. Cultures were then exposed to each endolysin at a concentration of 100 µg/ml in the 96 well plate and lytic activities were represented as the percentage of lysis relative to 100% activity of each endolysin against the *B. cereus* ATCC 4342 indicator strain after 20 min incubation. Alternatively, the plate lysis assay described above was used to determine host range against several *B. anthracis* strains where +, ++, and +++ indicates an observed clearing zone for 10 µg, 1 µg, 0.1 µg, respectively, of each endolysin.

Fluorescent labeling of CBDs. Purified CBDs were chemically crosslinked to an amine-reactive ALEXAFLUOR® 555 fluorescent dye (Thermo Fisher Scientific) according to the manufacturer's instructions with minor modifications. Briefly, 0.5 ml of CBD (2.0 mg/ml) was mixed with 50 µl of 1 M sodium bicarbonate and 100 µl of the ALEXAFLUOR® 555 dye (2.0 mg/ml in DMSO). The reaction mixture was incubated at room temperature for 1 hour with constant stirring. Unreacted dye was removed by application to a PD-10 desalting column (GE Healthcare). The fractions with labeled CBDs were collected and stored at 4° C. for future use to visualize binding.

CBD-binding assay. Overnight cultures of bacilli were pelleted at 5,000 rpm for 10 min at 4° C., resuspended in sterile PBS, and washed a second time. Cell suspension aliquots (100 µl) were mixed with 10 µl of each labeled CBDs in separate reactions, and incubated on ice for 10 min. The reaction in absence of fluorescent dye served as a control. After incubation, labeled bacterial cells were pelleted and washed with ice-cold PBS and diluted to 100 µl again. An aliquot (~1 µl) of this mixture was applied to a glass slide, sealed with a glass coverslip, visualized with an Eclipse 80i epifluorescent microscope (Nikon), and NIS-Elements software (Nikon) was used for image analysis.

Structural modeling of *Bacillus* bacteriophage endolysin EADs. The amino acid sequences of PlyP56, PlyN74, and PlyTB40 were submitted to the HHPred server (Söding, J et al., *The HHpred interactive server for protein homology detection and structure prediction. Nucleic Acids Research* 2005, 33, W244-W248) to identify appropriate homology modeling templates of known structures. The phylogenetically closest structurally characterized homolog in the RCSB Protein Data Bank (PDB) (Berman, H M et al., *The protein data bank. Nucleic Acids Research* 2000, 28, 235-242) was identified and selected from the resulting HHPred hit list for each endolysin EAD based on maximal percent identity. For PlyP56, the 1-alanoyl-d-glutamate peptidase from *Listeria monocytogenes* bacteriophage A500, known as Ply500 (Korndörfer, I P et al., *Structural analysis of the L-alanoyl-D-glutamate endopeptidase domain of Listeria bacteriophage endolysin Ply500 reveals a new member of the LAS peptidase family. Acta Crystallographica Section D: Biological Crystallography* 2008, 64, 644-650) was selected (PDB ID: 2VO9; 1.8 Å resolution) with 70% identity (E-value=2e-75). For PlyN74, the N-acetylmuramoyl-1-alanine amidase from *Bacillus anthracis* λ prophage Ba02, known as PlyL, (Low, L Y et al., *Structure and lytic activity of a Bacillus anthracis prophage endolysin.* Journal of Biological Chemistry 2005, 280, 35433-35439) was selected (PDB ID: 1YB0; 1.86 Å resolution) with 53% identity (E-value=7e-49). For PlyTB40, another N-acetylmuramoyl-1-alanine amidase with a different fold was selected (PDB ID: 1XOV; 1.8 Å resolution) from *Listeria monocytogenes* bacteriophage PSA, known as PlyPSA (Korndörfer, I P et al., *The crystal structure of the bacteriophage PSA endolysin reveals a unique fold responsible for specific recognition of Listeria cell walls.* Journal of Molecular Biology 2006, 364, 678-689), with 37% identity (E-value=3e-25). The template and target amino acid sequences for each EAD were subsequently aligned with Clustal X 2.1 (Larkin, M A et al., *Clustal Wand Clustal X version* 2.0. Bioinformatics 2007, 23, 2947-2948) using the default parameters. From each alignment (see FIGS. 6-8), a percent identity (% I=number of identical alignment positions/total number of alignment positions) and percent similarity (% S=[number of identical alignment positions+number of 'strong similarity' alignment positions]/total number of alignment positions) was calculated (PlyN74-1YB0: % I=51.3, % S=64.1; PlyP56-2VO9: % I=70.1, % S=81.6; PlyTB40-1XOV: % I=36.3, % S=53.2). Gaps (i.e. insertions and deletions) were included in the total number of alignment positions. Using the sequence alignments from Clustal X and the template structures from the PDB, the automodel function of MODELLER 9.16 (Fiser, A et al., *Modeling of loops in protein structures.* Protein Science 2000, 9, 1753-1773; Šali, A & Blundell, TL, *Comparative protein modelling by satisfaction of spatial restraints.* Journal of Molecular Biology 1993, 234, 779-815) was used to generate a population of 100 homology models for each EAD. The model with the lowest Discrete Optimized Protein Energy (DOPE) (Shen, MY & Sali, A, *Statistical potential for assessment and prediction of protein structures.* Protein Science 2006, 15, 2507-2524) score from each population was selected for further analysis (PlyN74: DOPE=−16088; PlyP56: DOPE=−15027; PlyTB40: DOPE=−16997). The selected EAD models were post-processed and visualized with SYBYL-X 2.1.1 (Certara USA, Inc.). The models were subjected to a short energy-minimization (Tripos Force Field, Gasteiger-Hückel charges, distance-dependent dielectric constant=4.0 D/A, termination criteria: energy gradient cutoff=0.05 kcal (mol× Å)-1 or 200 iterations) followed by generation of Connolly surfaces, onto which the electrostatic potential was mapped. The stereochemical quality of the final models and their corresponding PDB templates were assessed using PROCHECK (Laskowski, R A et al., *PROCHECK: A program to check the stereochemical quality of protein structures.* Journal of Applied Crystallography 1993, 26, 283-291). In each of the generated endolysin EAD models, >90% of the residues were located in the most favored regions, indicating good quality models.

RESULTS

Phylogenetic analysis. The 46 bacteriophage used in this study were originally isolated, sequenced, and annotated by undergraduate students under the SEA-PHAGES initiative (Jordan, T C et al., *A broadly implementable research course in phage discovery and genomics for first-year undergraduate students.* MBio 2014, 5(1):e01051-13) and deposited in the *Bacillus* Phages Database (*Bacillus*.phagesdb.org). All ORFs were analyzed for genes encoding putative endolysins. Sequences for 6 biochemically or structurally characterized homologs (LysB4, Ply500, PlyL, PlyPSA, LysBPS13, and phi29) were also included in our analysis (Korndörfer, I P et al., *The crystal structure of the bacteriophage PSA endolysin reveals a unique fold responsible for specific recognition of Listeria cell walls.* Journal of Molecular Biology 2006, 364, 678-689; Korndörfer, I P et al., *Structural analysis of the L-alanoyl-D-glutamate endopeptidase domain of Listeria bacteriophage endolysin Ply500 reveals a new member of the LAS peptidase family.* Acta Crystallographica Section D: Biological Crystallography 2008, 64, 644-650; Low, L Y et al., *Structure and lytic activity of a Bacillus anthracis prophage endolysin.* Journal of Biological Chemistry 2005, 280, 35433-35439; Park, J et al., *Characterization of an endolysin, LysBPS13, from a Bacillus cereus bacteriophage.* FEMS Microbiol Lett 2012, 332(1):76-83; Saedi, M S et al., *Cloning and purification of a unique lysozyme produced by Bacillus phage phi 29.* Proc Natl Acad Sci U S A 1987, 84(4):955-8; Son, B et al., *Characterization of LysB4, an endolysin from the Bacillus cereus-infecting bacteriophage B4.* BMC microbiology 2012, 12, 33). The 52 enzymes were grouped into nine separate phylogenetic clades based on identities and architectural arrangement of the EAD and CBD domains (Table 2). Phylogenetic analysis of the EADs alone indicated four different enzymatic clades (FIG. 1). The endolysins from bacteriophages Phrodo, Nigalana, and TsarBomba, called PlyP56, PlyN74, and PlyTB40, respectively, were chosen for expression and further study since they displayed EADs from separate clades but had similar CBDs (see below).

TABLE 2

Phylogenetic analysis of 46 *Bacillus* bacteriophage endolysins.

| Clade | EAD | CBD | Examples |
|---|---|---|---|
| I. | G25 muramidase | Amidase_02C | Vinny ORF63 |
| II. | G25 PlyB-like | Amidase_02C | Stitch ORF31 |
| III. | MurNAc-LAA | 2× LysM | Taylor ORF31 |
| IV. | MurNAc-LAA | SH3 | TsarBomba ORF40 (PlyTB40) |
| V. | VanY | 2× PG_binding_1 | SPO1 ORF107 |
| VI. | Peptidase M15_4/VanY | SH3 | Phrodo ORF56 (PlyP56) |
| VII. | GH24 muramidase | SH3 | Beachbum ORF23 |
| VIII. | PGRP | Amidase_02C | Waukesha ORF68 |

TABLE 2-continued

Phylogenetic analysis of 46 *Bacillus* bacteriophage endolysins.

| Clade | EAD | CBD | Examples |
|---|---|---|---|
| IX. | PGRP | SH3 | Nigalana ORF74 (PlyN74) |

Figure 2:
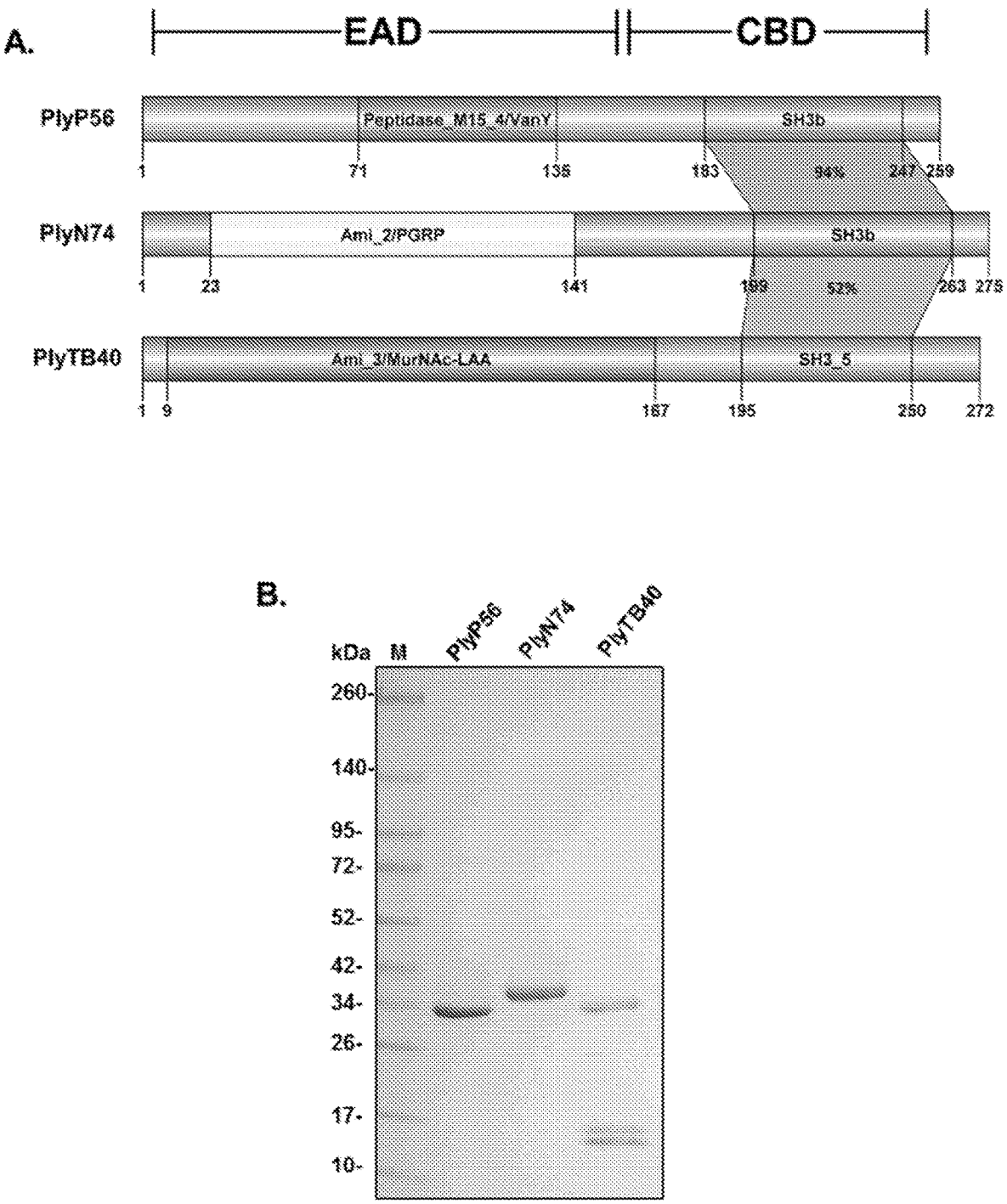
FIG. 2 illustrates *Bacillus* bacteriophage endolysin structural characterization and protein profile for PlyP56, PlyN74 and PlyTB40. As shown in Panel A, PlyP56, PlyN74, and PlyTB40 contain divergent N-terminal enzymatic active domains (EADs) and conserved C-terminal cell wall binding domains (CBDs). PlyP56 has a Peptidase_M15_4 EAD domain found within the VanY superfamily. PlyN74 has an Amidase_2 EAD domain that is part of the MurNAc-LAA superfamily. PlyTB40 has an Amidase_3 EAD that is also part of the MurNAc-LAA superfamily but lacks homology with the Amidase_2 domain of PlyN74. All three endolysins have similar SH3-family binding domains. As shown in Panel B, Purification of *Bacillus* phage endolysins. *E. coli* BL21-(DE3) cells were transformed with a vector encoding recombinant endolysins, grown, and induced with L-arabinose as described under Methods. The recombinant endolysins were purified to homogeneity by nickel affinity chromatography. Protein samples were analyzed for purity by SDS-PAGE with Coomassie blue staining. Lane 1, molecular mass markers as indicated; Lane 2, PlyP56; Lane 3, PlyN74; Lane 4, PlyTB40.
Figure 9:
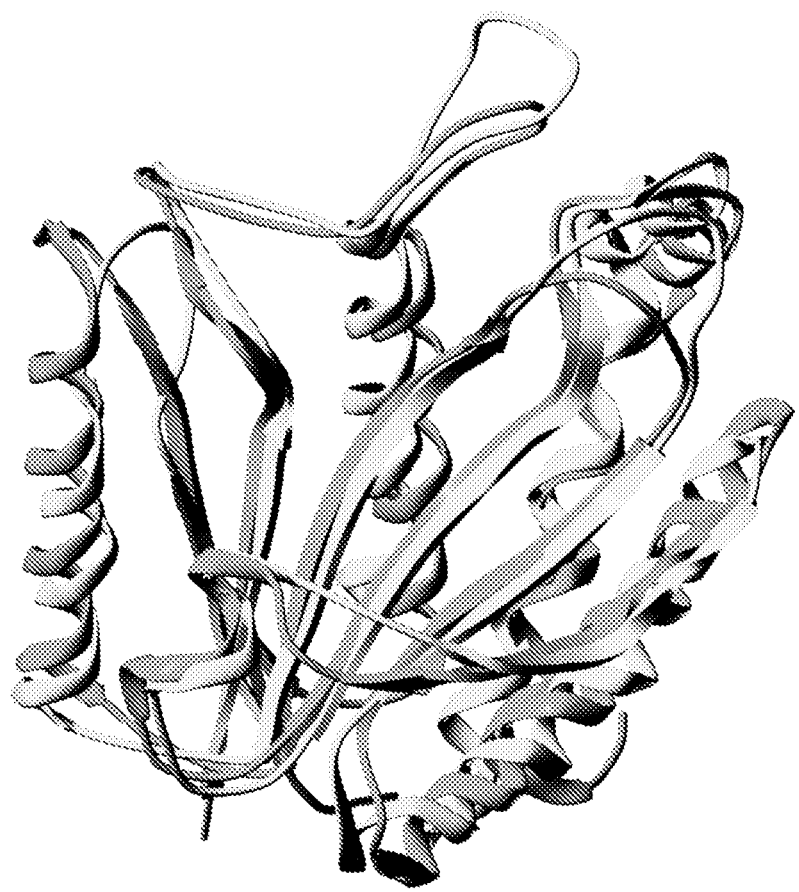
FIG. 9 illustrates carboxypeptidase T-type Amindase_3 fold. Ribbon diagrams of the endolysin EADs of *Listeria monocytogenes* bacteriophage PlyPSA (PDB ID: 1XOV; PlyTB40 homology modeling template; dark grey) and *Bacillus polymyxa* var. colistinus CwlV (PDB ID: 1JWQ; light gray), each exhibiting the carboxypeptidase T-type Amidase_3 fold.

Endolysin domain architecture and homology. A Pfam database analysis confirmed that PlyP56, PlyN74, and PlyTB40 each contained a singular N-terminal EAD and a C-terminal CBD (FIG. 2A). The PlyP56 EAD is predicted to be a member of the Peptidase_M15_4/VanY superfamily (Pfam 13539, Pfam 02557), which is associated with a d-alanyl-d-alanine carboxypeptidase activity. However, such an activity would not readily lead to lysis of the peptidoglycan. Furthermore, the PlyP56 EAD shares significant sequence homology (95% identity) with LysB4 (AFF27501.1), an endolysin from the *B. cereus* bacteriophage B4, which has a confirmed 1-alanoyl-d-glutamate endopeptidase activity based on mass spectrometry analysis (Son, B et al., *Characterization of LysB4, an endolysin from the Bacillus cereus-infecting bacteriophage B4*. BMC microbiology 2012, 12, 33). The PlyN74 EAD is predicted to belong to the Amidase_2/PGRP superfamily (Pfam 01510) and shares 95% identity to LysBPS13 (AEZ50187.1), a confirmed N-acetylmuramoyl-1-alanine amidase from the *B. cereus* bacteriophage BPS13 (Park, J et al., *Characterization of an endolysin, LysBPS13, from a Bacillus cereus bacteriophage*. FEMS Microbiol Lett 2012, 332(1):76-83). These enzymes cleave the amide bond between the glycan component (N-acetylmuramic acid) and the peptide component (1-alanine) of the peptidoglycan. Finally, the PlyTB40 EAD is a putative Amidase_3/MurNAc-LAA (pfam 01520). Similar to the Amidase_2 catalytic domain of the PGRP superfamily, the Amidase_3 catalytic domain also possesses an N-acetylmuramoyl-1-alanine amidase activity, although this EAD adopts a different fold (FIG. 9) (Büttner, F M et al., *X-Ray crystallography and its impact on understanding bacterial cell wall remodeling processes*. International Journal of Medical Microbiology 2015, 305, 209-216). Thus, despite PlyN74 and PlyTB40 containing structurally different catalytic domains (FIG. 5, Panels E and H), both endolysins share a similar enzymatic target: the amide bond between N-acetylmuramic acid and 1-alanine in the peptidoglycan.

In contrast to the divergent and non-homologous EADs, all three endolysins are predicted to have a type of src-homology 3 (SH3) domain as their C-terminal CBD (FIG. 2A). The CBDs of PlyP56 and PlyN74 have SH3 bacterial domains, known as SH3b domains (smart 00287), which share 94% identity. The PlyTB40 CBD has a very similar SH3_5 domain (pfam 08460) that shares ~52% identity with the SH3b domains of PlyP56 and PlyN74. Notably, SH3b and SH3_5 domains are commonly-found CBDs in endolysins derived from bacteriophage that infect Gram-positive bacteria (Nelson, D C et al., *Endolysins as antimicrobials*. Adv Virus Res 2012, 83, 299-365), including the *Bacillus*-specific endolysins Ply21 (Loessner, M J et al., *Three Bacillus cereus bacteriophage endolysins are unrelated but reveal high homology to cell wall hydrolases from different bacilli*. J Bacteriol 1997, 179(9):2845-2851) and LysB4 (Son, B et al., *Characterization of LysB4, an endolysin from the Bacillus cereus-infecting bacteriophage B4*. BMC microbiology 2012, 12, 33).

Purification and biochemical characterization. All three endolysins, and their corresponding CBDs, were expressed as soluble proteins in a pBAD24 expression vector and purified to homogeneity by nickel affinity chromatography via C-terminal 6xHis tags. The size of purified PlyP56, PlyN74, and PlyTB40 bands on SDS-PAGE corresponded to 28.5 kDa, 31.4 kDa, and 30.0 kDa, respectfully (FIG. 2B). Notably, the PlyTB40 purified protein fraction resulted in a full-length ~30 kDa protein and one or two smaller bands in the ~10-15 kDa range on SDS-PAGE. It should be noted that some clostridial and enterococcal endolysins use alternate translation start sites that generate an additional CBD resulting in formation of heterodimer enzymes, which would explain the presence of protein bands that correspond to the full-length endolysin and that of a CBD (Dunne, M et al., *Crystal structure of the CTP1L endolysin reveals how its activity is regulated by a secondary translation product*. J Biol Chem 2016, 291(10):4882-4893; Proenca, D et al., *A two-component, multimeric endolysin encoded by a single gene*. Mol Microbiol 2015, 95(5):739-753). However, we did not detect consensus Shine-Dalgarno sequences or in-frame start codons in the region corresponding to the beginning of the PlyTB40 CBD. Thus, it is believed that the smaller fragment(s) represent a degradation event despite the use of protease inhibitors during purification.

Figure 3:
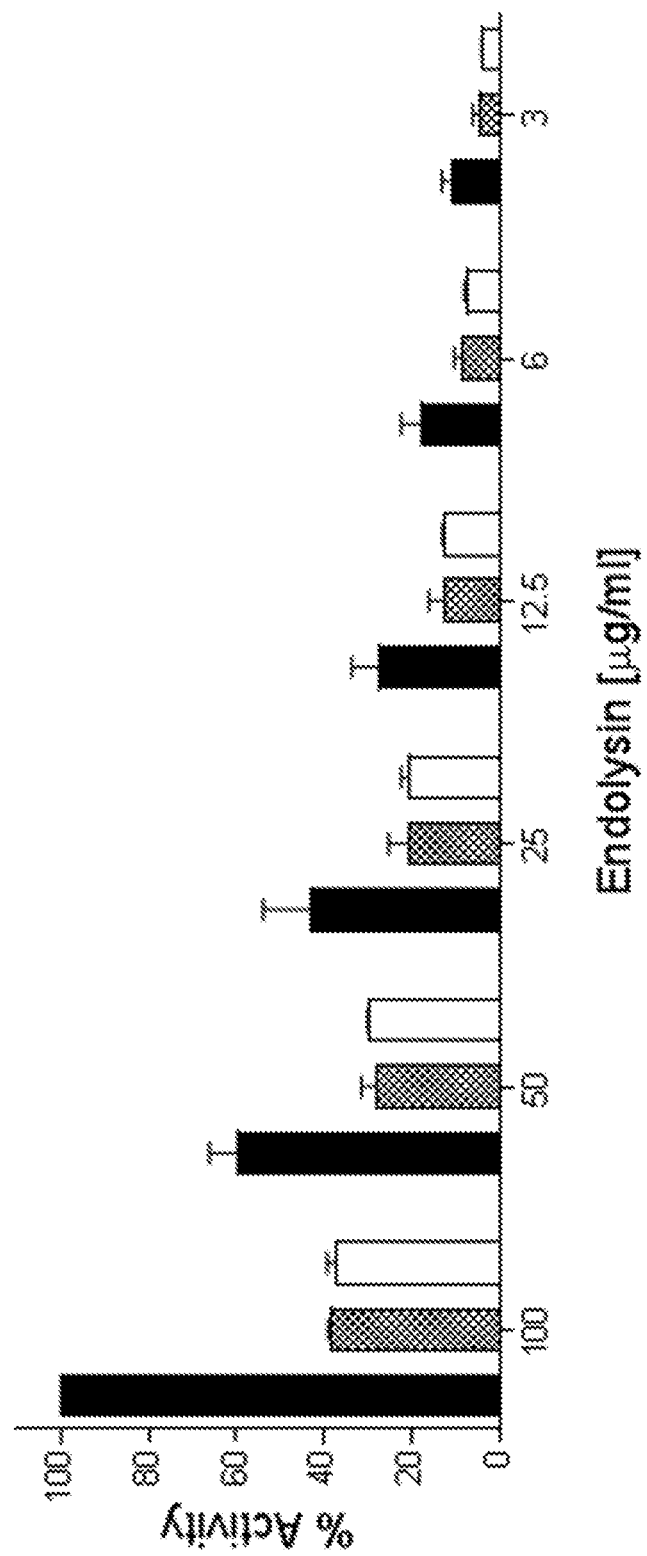
FIG. 3 illustrates graphically lytic activity of PlyP56, PlyN74, and PlyTB40. Stationary phase *B. cereus* ATCC 4342 cells at final OD600 of 1.0 were treated with endolysin doses from 100 µg/ml to 3 µg/ml over 20 min. PlyP56 (black bars), PlyN74 (checker bars), and PlyTB40 (white bars) are indicated. The cell lysis was assayed by turbidity reduction as described below. The percent lytic activities were normalized to 100% activity of PlyP56 (black bars) at 100 µg/ml. Experiments were run in triplicates on three independent days. The error bars represent standard deviation.

Activity and biochemical characterization of endolysins. All three endolysins exhibited a dose-response curve from 100 to 3 µg/ml when tested via the turbidity reduction assay against overnight cultures of *B. cereus* ATCC 4342, with PlyP56 being at least twice as active as PlyN74 and PlyTB40 at all tested concentrations (FIG. 3). PlyP56-induced lysis of the bacterial peptidoglycan caused a decrease in OD from 1.0 to 0.4 (60% decrease) within the first 4 minutes of the turbidity assay at the highest tested dose (100 µg/ml), whereas equimolar concentrations of PlyN74 and PlyTB40 required 10-15 minutes to achieve the same degree of lysis.

Figure 4:
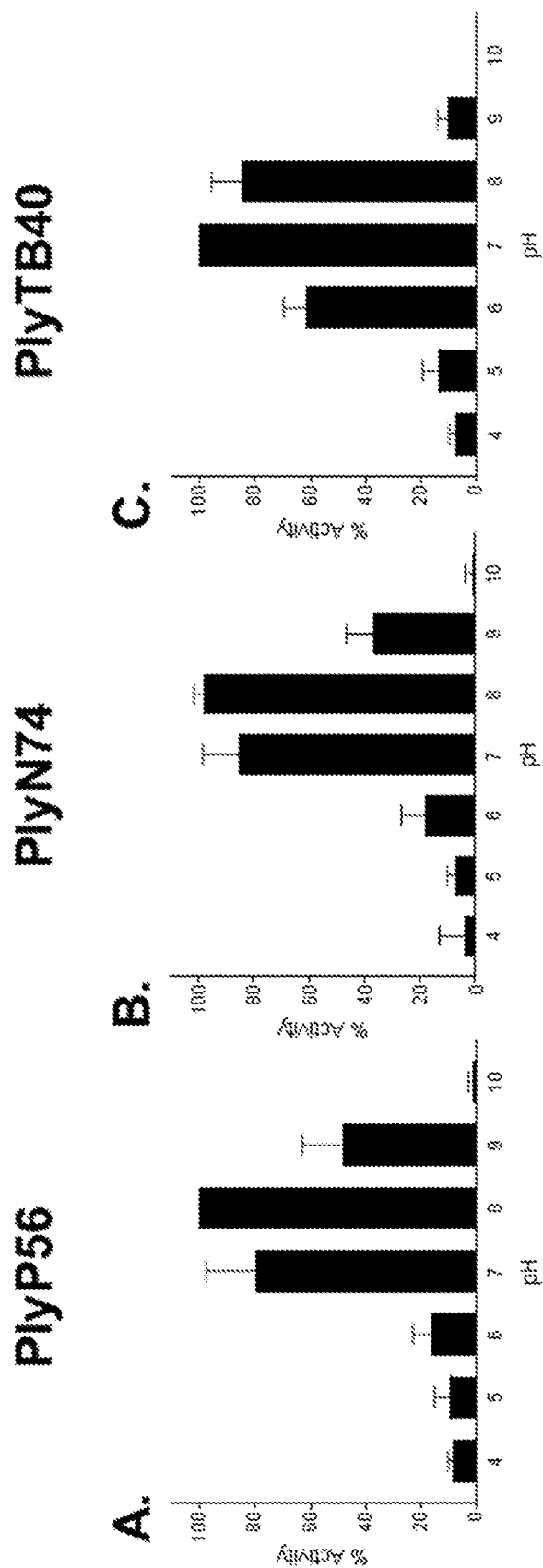
FIG. 4 illustrates graphically biochemical characterization of optimal conditions for *Bacillus* bacteriophage endolysins activity. The effects of pH (Panels A-C), NaCl dependence (Panels D-F), and temperature stability (Panels G-I) were evaluated for each of the three endolysins PlyP56 (A,D,G), PlyN74 (B,E,H), and PlyTB40 (C,F,I). The subject endolysins were assayed for lytic activity, each at 50 µg/ml, and tested separately via turbidity reduction assay against stationary phase *B. cereus* ATCC 4342 cells for 20 min. The temperature effect on lytic activity was tested after endolysins were pre-incubated at indicated temperatures for 30 min and subsequently recovered on ice for 5 min. Values are presented as a percentage of lytic activity in relation to highest activity observed for each tested parameter. The experiments were run in triplicates on three independent days. Error bars indicate standard deviations.
Figure 4:
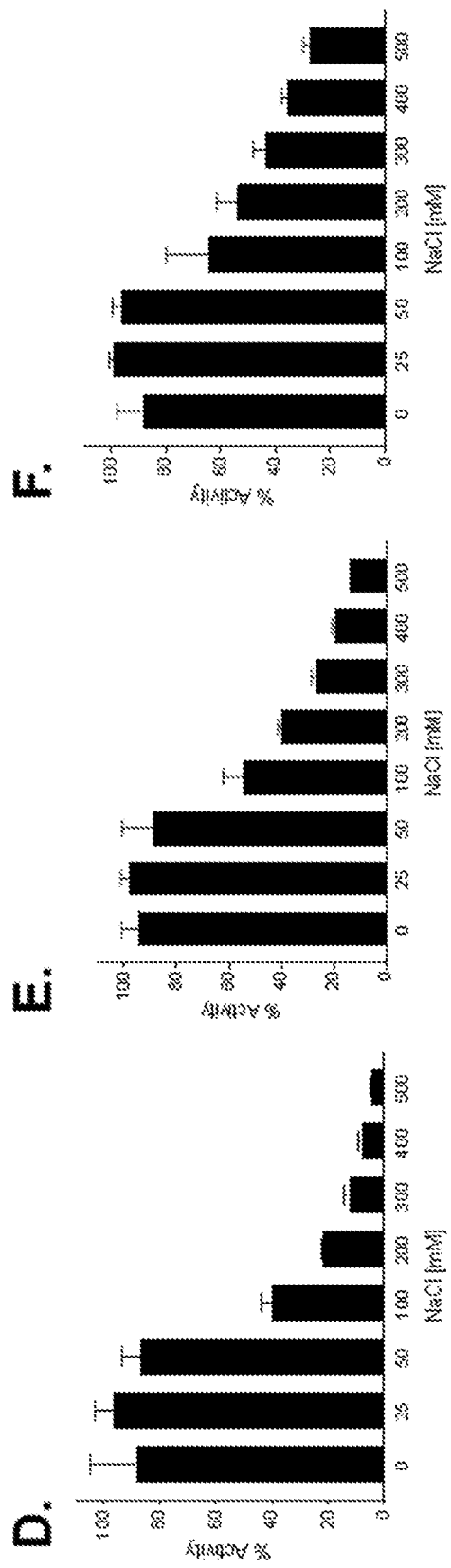
Figure 4:
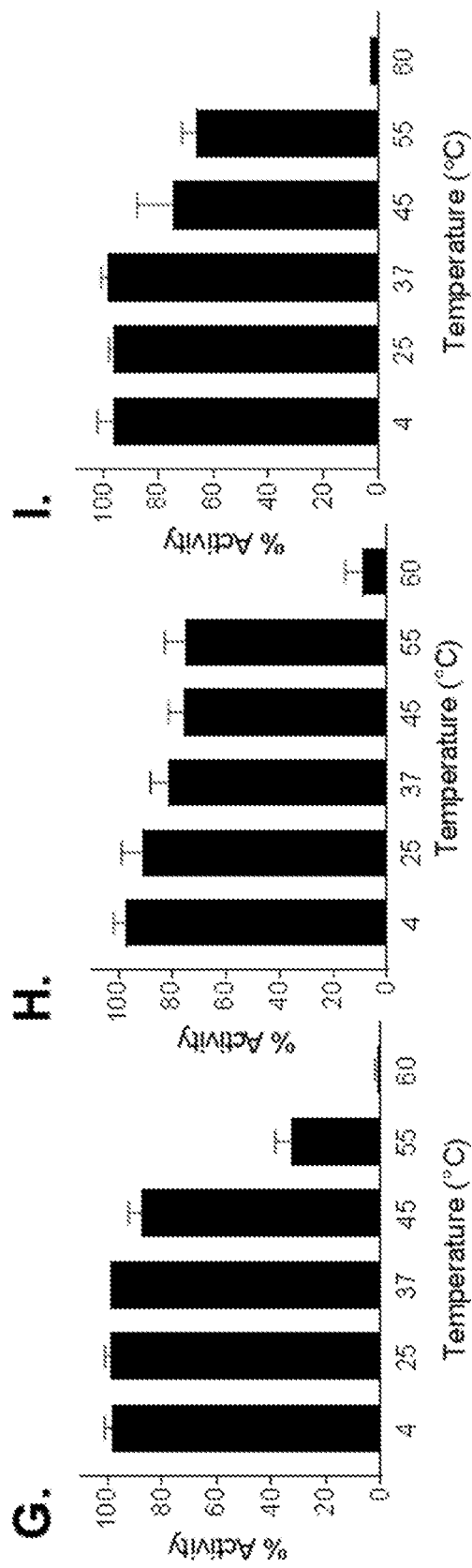

Based on numerous studies, the enzymatic effectiveness of endolysins can often be affected by salt concentration, pH, and temperature (Fischetti, V. A., *Bacteriophage endolysins: a novel anti-infective to control Gram-positive pathogens*. Int J Med Microbiol 2010, 300(6):357-362; Nelson, D C et al., *Endolysins as antimicrobials*. Adv Virus Res 2012, 83, 299-365; Garcia, P et al., *Synergy between the phage endolysin LysH5 and nisin to kill Staphylococcus aureus in pasteurized milk*. Int J Food Microbiol 2010, 141(3):151-155; Yuan, Y et al., *Characteristics of a broad lytic spectrum endolysin from phage BtCS33 of Bacillus thuringiensis*. BMC microbiology 2012, 12, 297). To determine the optimum conditions for PlyP56, PlyN74, and PlyTB40, the lytic activity of these enzymes was surveyed over a broad range of pH (3-11), NaCl concentrations (0-500 mM), and exposure to different temperatures (4° C. to 60° C.). In general, all endolysins displayed similar biochemical/biophysical profiles despite possessing different EADs (FIG. 4). All three endolysins displayed high lytic activity (90-100%) at pH 7 and 8 (FIG. 4, Panels A, B and C), but activity rapidly dropped off outside of this range for PlyP56 and PlyN74 (FIG. 4, Panels A and B). In contrast, PlyTB40 retained >60% activity at pH 6 and ~40% activity at pH 5 (FIG. 4C). These findings suggest a narrower pH range than found in other *Bacillus*-specific endolysins, but nonetheless, they are consistent with a skew toward neutral to basic pH optimums. For instance, PlyPH, a bacteriolytic enzyme identified within the genome of *B. anthracis*, exhibits a relatively broad optimum from pH 5 to 9 (Yoong, P et al., *PlyPH, a bacteriolytic enzyme with a broad pH range of activity and lytic action against Bacillus anthracis*. J Bacteriol 2006, 188(7):2711-2714), whereas LysB4, a PlyP56 homolog, has optimal lytic activity between pH 8.0 and pH 10.5 (Son, B et al., *Characterization of LysB4, an endolysin from the Bacillus cereus-infecting bacteriophage B4*. BMC microbiology 2012, 12, 33). LysBPS13, a *B. cereus*-specific endolysin and a homolog of PlyN74, exhibits similar low tolerance to acidic pH below 6.0 (Park, J et al., *Characterization of an endolysin, LysBPS13, from a Bacillus cereus bacteriophage*. FEMS Microbiol Lett 2012, 332(1):76-83). In the experiments, pH extremes not only reduced enzymatic activity of the surveyed endolysins, but also caused a precipitation of endolysins at the acidic pHs. Taken together, our findings suggest that *Bacillus* species-specific endolysins sustain their enzymatic activity at a broad pH range but prefer physiological and slightly basic conditions.

The influence of NaCl on enzymatic activity was also studied at pH 7.4, where all the enzymes displayed maximum activity. It was reported that salt concentrations can significantly enhance enzymatic activity of many endolysins (Garcia, P et al., *Synergy between the phage endolysin LysH5 and nisin to kill Staphylococcus aureus in pasteurized milk*. Int J Food Microbiol 2010, 141(3):151-155); however, NaCl concentrations up to 100 mM had little effect (<10% deviation) on the lytic activity of PlyP56, PlyN74, and PlyTB40 (FIG. 4, Panels D, E and F). A similar effect was observed for staphylococcal endolysin, PlyGRCS (Linden, S B et al., *Biochemical and biophysical characterization of PlyGRCS, a bacteriophage endolysin active against methicillin-resistant Staphylococcus aureus*. Appl Microbiol Biotechnol 2015, 99(2):741-752), which displayed full activity up to 500 mM NaCl. On the contrary, NaCl concentrations above 100 mM significantly inhibited enzymatic activity of all three enzymes, with PlyP56 being the most sensitive, losing half of its activity at just 100 mM NaCl. PlyTB40 was the least sensitive to NaCl of the three enzymes, but still lost half of its lytic activity at 300 mM.

The thermal stability of each endolysin was determined by incubation at temperatures ranging from 4° C. to 60° C., recovering on ice, and measuring residual activity by the turbidity reduction assay. It was determined that all endolysins were enzymatically active over a temperature range from 4° C. to 45° C., with minor deviations in activity (+15% of maximum) (FIG. 4, Panels G, H and I). At 55° C., PlyN74 and PlyTB40 maintained >80% of maximum activity whereas PlyP56 displayed <40% of maximum activity. By 60° C., all three endolysins had <10% lytic activity remaining. In general, the thermal stability profile of PlyP56, PlyN74, and PlyTB40 was found to be consistent with other *Bacillus* endolysins. For instance, LysBPS13 and BtCS33 were inactivated after a 30 min incubation at 60° C. in the absence of thermoprotective agents (Yuan, Y et al., *Characteristics of a broad lytic spectrum endolysin from phage BtCS33 of Bacillus thuringiensis*. BMC microbiology 2012, 12, 297).

Figure 5:
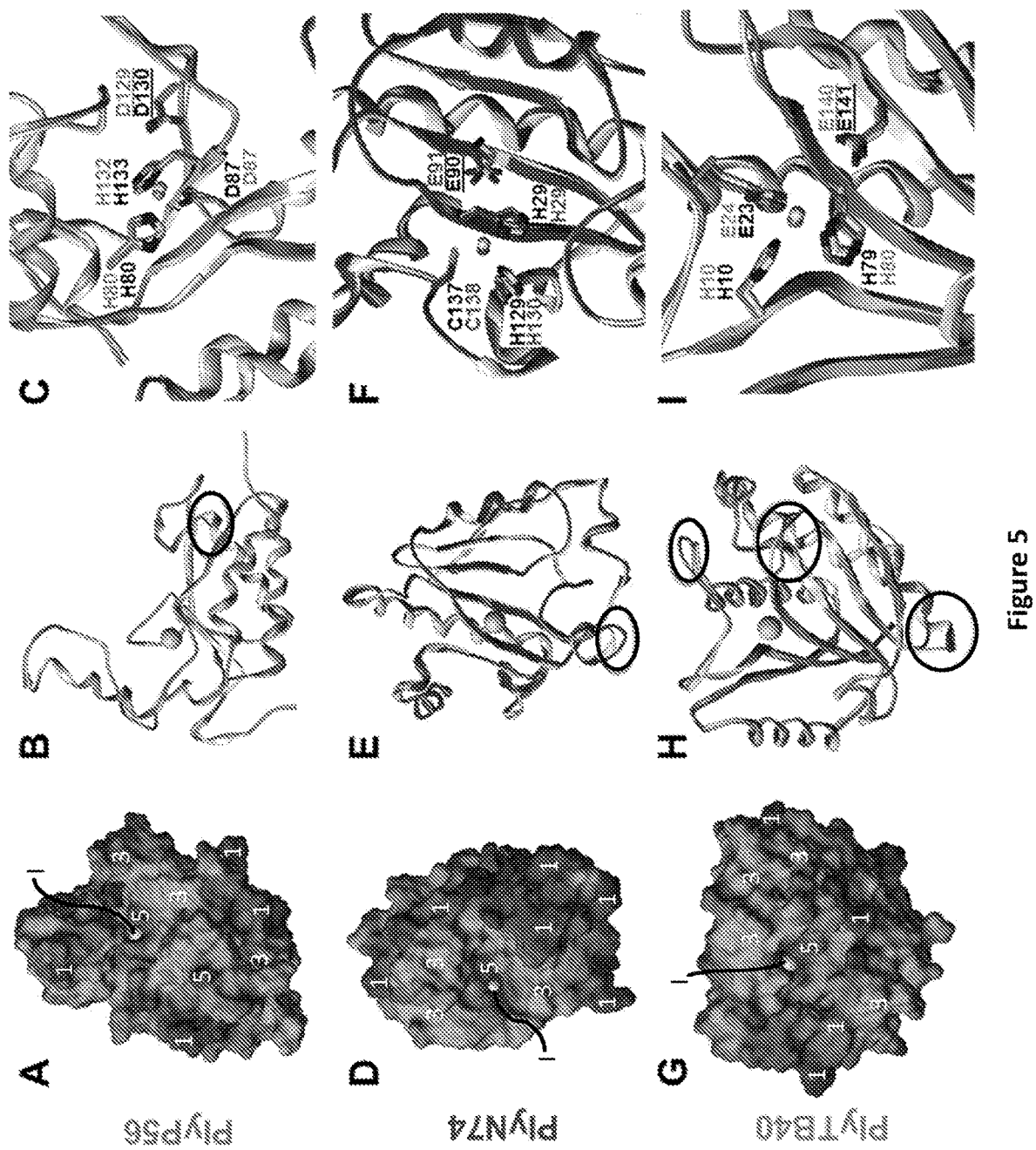
FIG. 5 are homology models of PlyP56 (Panels A-C), PlyN74 (Panels D-F), and PlyTB40 (Panels G-I) EADs. As shown in Panels A,D and G, Connolly surface representations are coded by electrostatic potential (1/blue=most positive; 3/green intermediate; red/5=most negative). A sphere represents the Zn2+ ion (shown by reference 'I'). As shown in Panels B,E and H, ribbon representations of the homology modeling template (PlyP56: PDB ID=2VO9; PlyN74: PDB ID=1YB0; PlyTB40: PDB ID=1XOV; light gray) and target (PlyP56; PlyN74; PlyTB40; dark gray) EADs illustrating the protein fold conservation. Ovals represent sequence insertions or deletions (see FIGS. 6-8). Catalytic active site amino acid residues are shown in Panels C, F and I, wherein residues represent template (black) and target (PlyP56; PlyN74; PlyTB40; light gray) EADs. An underline indicates the catalytic base/acid. Small spheres represent the Zn2+ ion.
Figure 8:
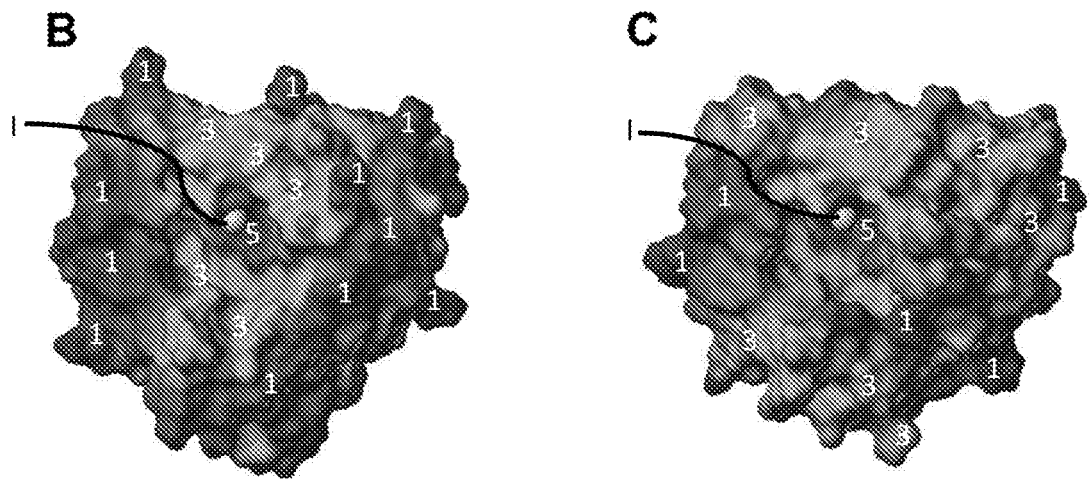
FIG. 8 illustrates PlyTB40 sequence alignment with structural homolog PlyPSA. Panel A shows sequence alignment of *L. monocytogenes* page PSA (PlyPSA) from PDB entry 1XOV and PlyTB40 EADs (Clustal X alignment symbols: asterisk=identical; colon=strongly similar; period=weakly similar; space=not similar). Overall percent identity (#identical/#total)=36.3%; percent similarity [(#identical+#strongly similar)/#total]=53.2%. Arrows indicate the metal-binding residues (black fill) and the catalytic base/acid (white fill). Ovals represent sequence insertions or deletions; see FIG. 5 (Panel B-C). Connolly surfaces coded by electrostatic potential (1/blue=most positive; 3/green=intermediate; 5/red=most negative) for the template PlyPSA shown in Panel B, and the modeled PlyTB50 EAD shown in Panel C; a sphere I represents the $Zn^{2+}$ ion.

Structural modeling of *Bacillus* bacteriophage endolysin EADs. We used homology modeling techniques (see methods) to generate plausible three-dimensional models of the PlyP56, PlyN74, and PlyTB40 EADs (FIG. 5). Each model fit its template well, with complete conservation of catalytic residues, moderate to high conservation of non-catalytic amino acids, and only a few small insertions or deletions in loop regions. The differences in amino acid composition on the surfaces of closely-related EAD family members are responsible for differences in their shape and electrostatic nature (FIGS. 6-8). These factors in turn contribute to differences in the functional protein-protein interactions and catalytic specificity exhibited by members within and between the various endolysin fold families (Büttner, F M et al., *X-Ray crystallography and its impact on understanding bacterial cell wall remodeling processes*. International Journal of Medical Microbiology 2015, 305, 209-216; Firczuk, M & Bochtler, M, *Folds and activities of peptidoglycan amidases*. FEMS Microbiology Letters 2007, 31, 676-691; Schmelcher, M et al., *Bacteriophage endolysins as novel antimicrobials*. Future Microbiology 2012, 7, 1147-1171). Taken together, the 3-D structural modeling results support the functional prediction of N-acetylmuramoyl-l-alanine amidase activity for the PlyN74 and PlyTB40 endolysins, while clarifying Ply56 as an 1-alanoyl-d-glutamate peptidase.

Figure 10:
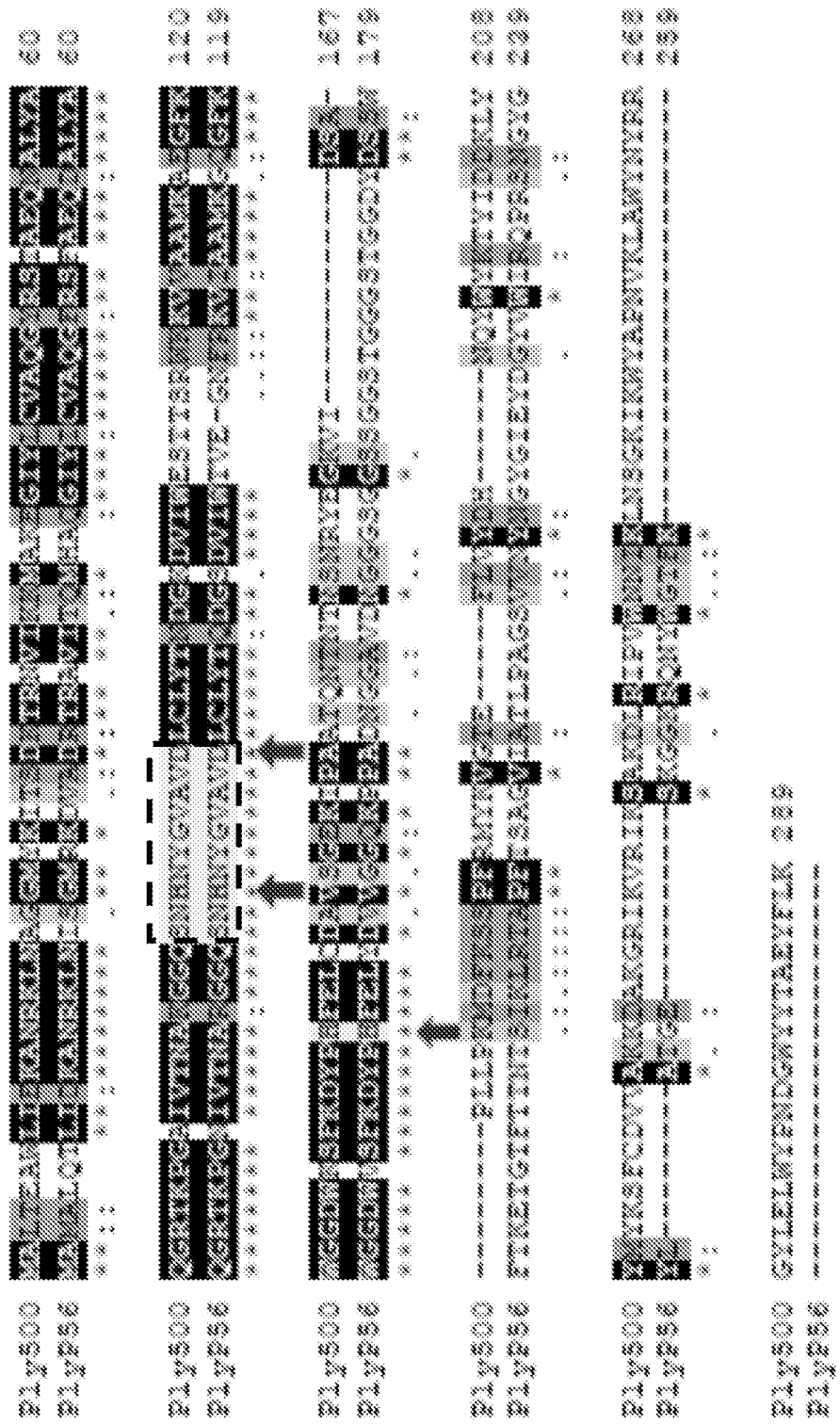
FIG. 10 shows sequence alignments for Ply500 and PlyP56, wherein both Ply500 and PlyP56 contain a conserved metal binding sequence (SxHxxGxAxD; dashed line rectangle).

Effect of divalent metal ions. Based on 3-D modeling, all three endolysin EADs are predicted to have a characteristic monometallic metallopeptidase-like catalytic active site in which a $Zn^{2+}$ ion is tetrahedrally coordinated by three conserved amino acid residues and a water molecule, and that also contains an adjacent catalytic base/acid, usually Asp or Glu (Cerda-Costa, N & Gomis-Ruth, FX, *Architecture and function of metallopeptidase catalytic domains*. Protein Sci 2014, 23(2):123-44). For PlyP56, the $Zn^{2+}$-coordinating residues are His80, Asp87, and His132, and the catalytic base/acid is Asp129 (FIG. 5, Panel C). For PlyN74, the $Zn^{2+}$-coordinating residues are His29, His130, and Cys138, and the catalytic base/acid is Glu91 (FIG. 5, Panel F). For PlyTB40, the $Zn^{2+}$-coordinating residues are His10, Glu24, and His80, and the catalytic base/acid is Glu140 (FIG. 5, Panel I). Significantly, Ply500 contains a conserved metal binding sequence (SxHxxGxAxD) and its crystal structure revealed an ion in the active site (Komdörfer, I P et al., *Structural analysis of the L-alanoyl-D-glutamate endopeptidase domain of Listeria bacteriophage endolysin Ply500 reveals a new member of the LAS peptidase family*. Acta Crystallographica Section D: Biological Crystallography 2008, 64, 644-650). Sequence alignments detected this motif in PlyP56 (FIG. 10). Although not necessarily associated with a specific sequence motif, the metal binding site in Amidase_2 and Amidase_3 N-acetylmuramoyl-1-alanine amidases has been structurally characterized using crystal structures, and strictly conserved metal-coordinating residues have been identified (Büttner, F M et al., *X-Ray crystallography and its impact on understanding bacterial cell wall remodeling processes*. International Journal of Medical Microbiology 2015, 305, 209-216). The sequence similarity of PlyN74 and PlyTB40 to Amidase_2 and Amidas_3 N-acetylmuramoyl-1-alanine amidases and the high quality of the resulting MODELLER-generated models provide strong evidence that these metal binding sites are indeed present in these endolysin EADs as well.

Figure 11:
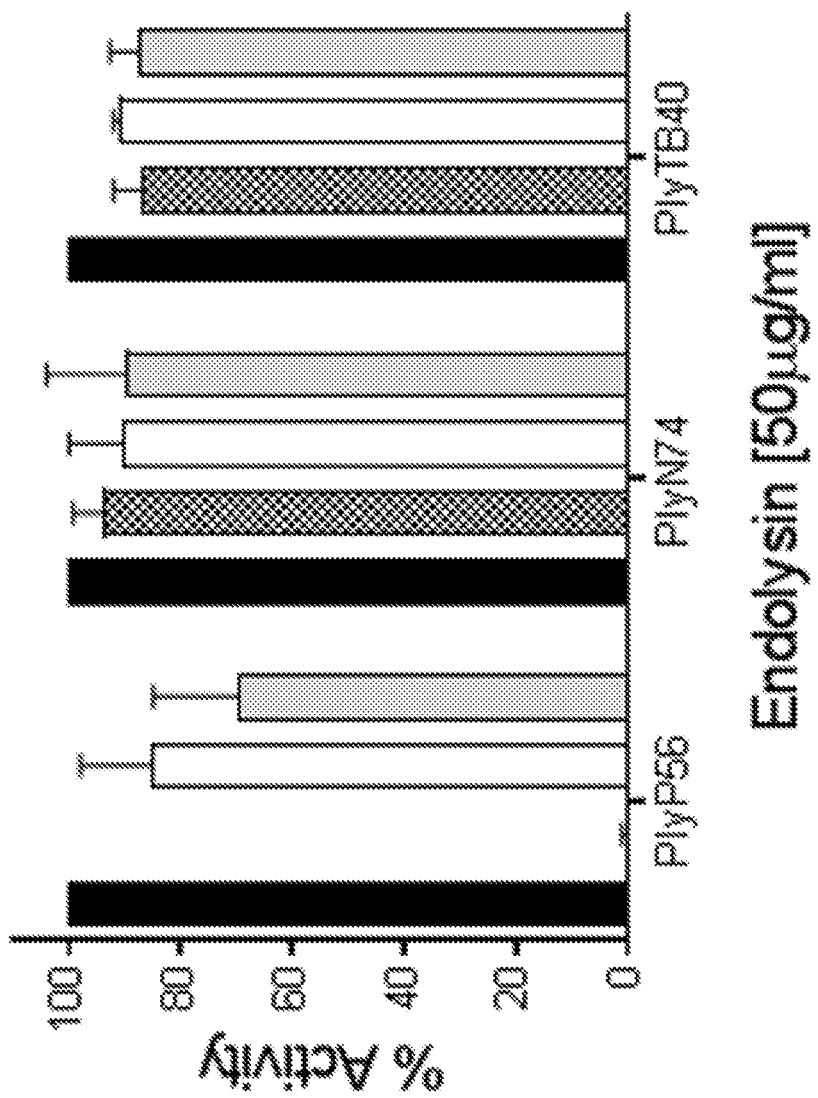
FIG. 11 illustrates graphically metal binding properties of PlyP56, PlyN74 and PlyTB40. The influence of divalent cations on PlyP56, PlyN74, and PlyTB40 lytic activity against stationary phase *B. cereus* ATCC 4342 was assayed via turbidity reduction assay. Mean values from three independent experiments run in triplicate are represented as the percentage residual lytic activity relative to untreated endolysins (black bars). Endolysins treated with EDTA (checker bars), and subsequently recovered via dialysis with additions of divalent ions, Mg2+(white bars), Ca2+(grey bars) are shown.

To further elucidate these findings, PlyP56, PlyN74, and PlyTB40 were dialyzed overnight in buffer supplemented with 5 mM EDTA to remove residual metal ions. Interestingly, EDTA treatment completely ablated enzymatic activity of PlyP56 but had no effect on the activities of PlyN74 or PlyTB40 (FIG. 11). Further, EDTA-treated proteins were dialyzed overnight in TBS supplemented with an excess of metal relative to the EDTA (i.e. 6 mM $Mg^{2+}$ or 6 mM $Ca^{2+}$) to restore cations in these enzymes. Lytic activity of PlyP56 was restored to 80% of the pre-EDTA levels by $Mg^{2+}$ ions and to 70% by $Ca^{2+}$ ions (FIG. 11). EDTA results are consistent with those found for LysB4, an EAD sequence homolog of PlyP56, which had activity restored to EDTA-treated samples by the addition of $Mg^{2+}$ or $Ca^{2+}$ ions (Son, B et al., *Characterization of LysB4, an endolysin from the Bacillus cereus-infecting bacteriophage B4*. BMC microbiology 2012, 12, 33). This confirms that PlyP56 requires divalent metal ions for its enzymatic activity.

In contrast to the PlyP56 results, EDTA treatment had no effect on the enzymatic activity of PlyN74 despite an ion being present in the active site of the crystal structure for PlyL, a homolog of the PlyN74 EAD (Low, L Y et al., *Structure and lytic activity of a Bacillus anthracis prophage endolysin*. Journal of Biological Chemistry 2005, 280, 35433-35439). However, EDTA-treated LysBPS13, another PlyN74 homolog, was similarly not dependent on the presence of metal ions for activity (Park, J et al., *Characterization of an endolysin, LysBPS13, from a Bacillus cereus bacteriophage*. FEMS Microbiol Lett 2012, 332(1):76-83). Finally, we found that PlyTB40 was also not affected by EDTA, even though a Zn2+ ion was identified in crystal structure of homologous PlyPSA (Korndörfer, I P et al., *The crystal structure of the bacteriophage PSA endolysin reveals a unique fold responsible for specific recognition of Listeria cell walls*. Journal of Molecular Biology 2006, 364, 678-689).

Host specificity. To determine the host range of PlyP56, PlyN74, and PlyTB40, lytic activity was tested via turbidity assay on a variety of *B. cereus* strains and other Bacillaceae (Table 3). Similar to the dose response curves for *B. cereus* ATCC 4342, PlyP56 was more effective in lysing *B. cereus sensu lato* group species than PlyN74 or PlyTB40, but all three enzymes displayed strong activity, defined as >20% lysis in the 20 min assay period, against all *sensu lato* members tested (four *B. cereus* strains and one *B. thuringiensis* strain). In addition, all three enzymes showed strong activity against *Bacillus pumilus* strain BJ0050, PlyP56 and PlyN74 both showed strong activity against *Bacillus megaterium* and *Bacillus amyloliquefaciens*, PlyN74 showed strong activity against *Bacillus licheniformis*, and PlyP56 showed strong activity against *Bacillus circulans* and *LysinBacillus sphaericus*. Weaker but measurable activity was also noted for all three enzymes against *Bacillus coagulans*, *Bacillus subtilis*, and *PaeniBacillus polymyxa*.

TABLE 3

Relative lytic activity of Bacillus bacteriophage endolysins.

| Species | Strain[1] | Bacteriophage endolysins[2] | | |
|---|---|---|---|---|
| | | PlyP56 | PlyN74 | PlyTB40 |
| B. cereus | ATCC 4342 | 84.9 ± 6.0 | 69.2 ± 9.8 | 71.9 ± 12.9 |
| B. cereus | ATCC 14579 | 73.4 ± 1.3 | 59.7 ± 7.2 | 40.9 ± 20.5 |
| B. cereus | ATCC 11778 | 79.6 ± 4.4 | 60.6 ± 4.4 | 58.2 ± 13.2 |
| B. cereus | ATCC 13061 | 45.8 ± 2.4 | 37.9 ± 3.8 | 24.0 ± 8.1 |
| B. thuringiensis | ATCC 10792 | 38.7 ± 5.2 | 35.8 ± 9.1 | 25.6 ± 6.6 |
| B. amyloliquefaciens | ATCC 23842 | 36.5 ± 20.5 | 23.9 ± 13.8 | 6.2 ± 2.4 |
| B. circulans | ATCC 4513 | 53.2 ± 3.2 | 17.2 ± 5.1 | 5.5 ± 5.1 |
| B. coagulans | ATCC 7050 | 8.0 ± 1.7 | 5.7 ± 7.9 | 4.6 ± 4.5 |
| B. licheniformis | ATCC 14580 | 4.6 ± 6.4 | 30.2 ± 3.6 | 9.6 ± 3.7 |
| B. megaterium | ATCC 14581 | 83.9 ± 12.3 | 30.2 ± 15.5 | 9.6 ± 1.6 |
| B. pumilus | BJ0050 | 58.8 ± 15.2 | 46.1 ± 11.1 | 32.6 ± 14.4 |
| B. pumilus | ATCC 700814 | 16.7 ± 18.4 | 10.9 ± 12.5 | 2.6 ± 4.3 |
| B. subtilis | ATCC 6051 | 3.5 ± 1.9 | 1.4 ± 0.5 | 0.1 ± 0.2 |
| B. subtilis | ATCC 33608 | 2.9 ± 2.3 | 1.6 ± 2.7 | 0.6 ± 0.8 |
| Lysinb. Sphaericus | ATCC 4525 | 36.9 ± 19.8 | 18.9 ± 9.4 | 10.8 ± 3.4 |
| Paenib. Polymyxa | ATCC 7070 | 6.0 ± 4.7 | 3.7 ± 4.3 | 3.1 ± 1.5 |

[1]See Methods for source of species and strains. Strains in bold belong to the *B. cereus sensu lato* group.
[2]Activity of endolysins was evaluated via turbidity reduction assay. Values reported are the percent decrease in absorbance ($OD_{600}$) of cells treated with endolysins normalized to values of untreated cells after 20 min incubation with 100 µg/ml of each endolysin. The starting absorbance of mid-log cells was adjusted to an $OD_{600}$ of 1.0. Values represent mean values from three independent experiments, run in triplicate.

*B. cereus* ATCC 4342 is a transition state strain that is phylogenetically located between *B. cereus* and *B. anthracis* (Helgason, F et al., *Bacillus anthracis, Bacillus cereus, and Bacillus thuringiensis—one species on the basis of genetic evidence*. Appl Environ Microbiol 2000, 66(6):2627-2630), and as such, the disclosed enzymes are believed to be equally effective in cell lysis of *B. anthracis*. However, using the same set of parameters employed for assays in Table 3, we did not observe lytic activity in a turbidity reduction assay against biosafety level 2 *B. anthracis* strains (34F2 Sterne, Ames35, and UM23) or the biosafety level 3 *B. anthracis* Ames strain. However, lytic activity measured via a plate lysis assay revealed significant lysis of *B. anthracis* Ames35 bacilli by PlyP56 and PlyN74 with lesser activity against the *B. anthracis* UM23 strain (Table 4). PlyTB40, on the other hand, had lower activity against these strains. Collectively, the findings demonstrate that PlyP56, PlyN74, and PlyTB40 have targeted lytic activity against the *B. cereus sensu lato* group and closely related species.

TABLE 4

Plate lysis.

| Species | Strain[1] | Bacteriophage endolysins[2] | | |
|---|---|---|---|---|
| | | PlyP56 | PlyN74 | PlyTB40 |
| B. cereus | ATCC 4342 | +++ | +++ | ++ |
| B. anthracis | Ames 35 | ++ | +++ | + |
| B. anthracis | UM23 | + | +/− | +/− |

[1]See Methods for source of species and strains.
[2]Activity of endolysins was evaluated via plate lysis assay. 10 µl of each endolysin containing 10 µg, 1 µg or 0.1 µg were spotted onto a surface of semisolid agar containing a mid-log bacterial cell suspension. The strength of lysis was defined by the presence of a clearing zone: +/−, for a partial clearing zone at 10 µg; +, for a clearing zone at 10 µg; ++, for a clearing zone at 1 µg; and +++, for a clearing zone at 0.1 µg. PBS was spotted in equal volumes and served as a negative control.

Figure 12:
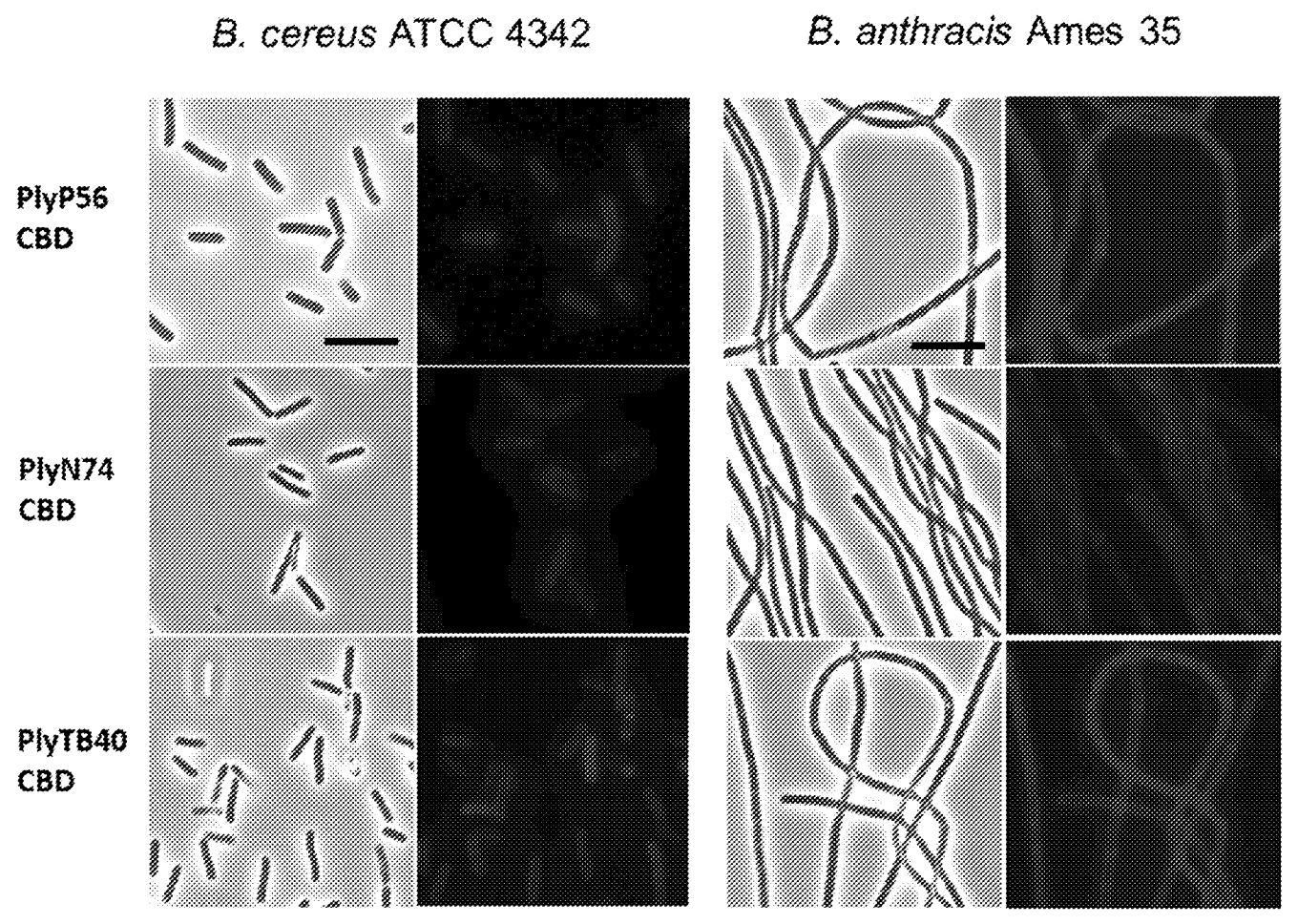

Cell wall binding. As with many endolysins, the SH3b and SH3_5 domains present in PlyP56, PlyN74, and PlyTB40 are believed to function as their CBDs. To test this hypothesis, we chemically crosslinked the CBDs of these enzymes with ALEXA FLUOR® 555, purified the crosslinked CBDs, and assessed their binding properties by fluorescent microscopy. All three CBDs bound tightly to the peptidoglycan of *B. cereus* ATCC 4342 and even labeled the septal plane (FIG. 12, two left columns). Additionally, all three CBDs bound tightly to the peptidoglycan of the *B. anthracis* Ames strain (FIG. 12, two right columns) as well as the *B. anthracis* UM23 strain.

DISCUSSION

Bacteriophage-encoded endolysins are of great interest for their potential as antimicrobial agents useful for controlling bacterial infections and preventing biofilm formation (Schuch, R et al., *Use of a bacteriophage lysin to identify a novel target for antimicrobial development*. PLoS One 2013, 8(4):e60754; Pires, D P et al., *Bacteriophage-encoded depolymerases: their diversity and biotechnological applications*. Appl Microbiol Biotechnol 2016, 100(5):2141-2151; Schuch, R et al., *A genetic screen to identify bacteriophage lysins*. Methods Mol Biol 2009, 502, 307-319). They can also be used for unwanted food contamination by opportunistic or pathogenic bacteria (Schmelcher, M & Loessner, MJ, *Application of bacteriophages for detection of foodborne pathogens*. Bacteriophage 2014, 4(1):e28137). Three *B. cereus* specific endolysins, PlyP56, PlyN74, and PlyTB40 are isolated and characterized herein, which all share basic structural properties of an N-terminal conserved EAD and a C-terminal CBD.

PlyP56 is predicted to have an 1-alanoyl-d-glutamate peptidase activity derived from the Peptidase_M15_4/VanY superfamily EAD domain. Sequence analysis identified a conserved (SxHxxGxAxD) motif within the PlyP56 EAD that plays an active role in harboring a metal ion, as first described for VanX of *Enterococcus faecium* (McCafferty, D G et al., *Mutational analysis of potential zinc-binding residues in the active site of the enterococcal D-Ala-D-Ala dipeptidase VanX*. Biochemistry 1997, 36(34):10498-10505) and supported by modeling studies with the Ply500 structural homolog (FIG. 5). As predicted, the PlyP56 lytic activity was abolished by EDTA treatment, which was subsequently restored by addition of excess Mg2+ or Ca2+ ions. The PlyN74 Amidase_2/PGRP superfamily EAD and the PlyTB40 Amidase_3/MurNAc-LAA superfamily EAD are not homologous and arise from different phylogenetic clades (Table 2), but they nonetheless are predicted to possess identical N-acetylmuramoyl-1-alanine amidase activities, suggesting convergent evolution of these superfamily domains. Our modeling to structural homologs for both of these EADs suggested a metal binding pocket with active site residues similar to those of the PlyP56 EAD. However, we were unable to inhibit lytic activity of these two endolysins by EDTA treatment. This discovery suggests that enzymatic activity of both endolysins is independent from metal ions (see Park, J et al., *Characterization of an endolysin, LysBPS13, from a Bacillus cereus bacteriophage*. FEMS Microbiol Lett 2012, 332(1):76-83) for the PGRP superfamily. Alternatively, it is possible that the affinity of the metal ion to the coordinating residues was too strong to be susceptible to chelation by EDTA.

PlyP56, PlyN74, and PlyTB40 had very similar biochemical, biophysical, and binding/host range characteristics. The similar binding patterns of these endolysins were anticipated since they all had similar SH3-family CBDs and were originally selected due to high lytic activity on the same *B. cereus* ATCC 4342 indicator strain. However, all three endolysins have distinct EADs; however, their pH, NaCl sensitivity, and temperature stability profiles surprisingly overlap to a large degree. Given that PlyP56 displays twice the activity of PlyN74 and PlyTB40, it is inviting to speculate that the Peptidase_M15_4 EAD of PlyP56 is more efficient than the Amidase_2 or Amidase_3 EADs of PlyN74 and PlyTB40, respectively. This is further supported by the near identical CBDs shared by PlyP56 and PlyN74, suggesting these enzymes are only differentiated by their EADs. However, the differences in charge of the EADs cannot be discounted as contributing to the observed differences in activity. A number of studies have reported correlation between the charge of an EAD and its enzymatic activity (Oliveira, H et al., *Molecular aspects and comparative genomics of bacteriophage endolysins*. J Virol 2013, 87(8): 4558-4570). Truncated, positively charged EADs of PlyL and CD27L were reported to have higher bactericidal activity and broader host spectrum than their wild-type precursors (Low, L Y et al., *Role of net charge on catalytic domain and influence of cell wall binding domain on bactericidal activity, specificity, and host range of phage lysins*. J Biol Chem 2011, 286(39):34391-34403; Mayer, M J et al., *Structure-based modification of a Clostridium difficile-targeting endolysin affects activity and host range*. J Bacteriol 2011, 193(19):5477-5486). Remarkably, at neutral pH, the PlyP56 EAD and linker sequence (residues 1-173) would have a predicted net positive charge (pI=8.55), the PlyN74 EAD/linker (residues 1-189) would have a neutral charge (pI=7.02), and the PlyTB40 EAD/linker (residues 1-190) would have a slight negative charge (pI=6.28). It is believed that differences in charge of the EADs, specifically positively charged EADs, enhance binding properties of the CBDs to negatively charged wall teichoic acids on the bacterial surface and contribute to observed lytic activity.

It is noteworthy that PlyP56, PlyN74, and PlyTB40 had higher activity against *B. cereus* ATCC 4342 than they did against any other bacilli. Significantly, *B. cereus* ATCC 4342 is a known transition state strain between *B. cereus* and *B. anthracis*, and it is the only *B. cereus* strain lysed by the PlyG endolysin, which lyses all *B. anthracis* strains. Therefore, it is believed that the disclosed endolysins disclosed herein would also be active against *B. anthracis* strains. Although we observed strong binding to *B. anthracis* via all three endolysin CBDs (FIG. 12, right two columns) as well as activity against *B. anthracis* in a spot lysis assay for the full-length proteins (Table 4), the overall lytic activity of PlyP56, PlyN74, and PlyTB40 against *B. anthracis* species is weaker since activity was not observed in a liquid turbidity reduction assay. However, this diminished activity may be related to assay conditions, the strains selected for study, differences in the peptidoglycan between members of the *sensu lato* group, or the SH3-based CBDs present in our enzymes. Additionally, there is no homology between PlyG and any of the endolysins of the present invention, and PlyL, another well-characterized endolysin with high activity against *B. anthracis* (Low, L Y et al., *Structure and lytic activity of a Bacillus anthracis prophage endolysin*. Journal of Biological Chemistry 2005, 280, 35433-35439), shares only 53% homology to the EAD of PlyTB40. Moreover, the absence of homology between the CBDs of our enzymes and that of characterized *B. anthracis* endolysins suggests they do not share common epitopes.

*Bacillus* bacteriophage-derived endolysins, PlyP56, PlyN74, and PlyTB40, were cloned, purified, and characterized for antimicrobial properties. Sequence alignment revealed that the subject endolysins have an N-terminal enzymatically active domain (EAD) linked to a C-terminal cell wall binding domain (CBD). PlyP56 has a Peptidase_M15_4/VanY superfamily EAD with a conserved metal binding motif and displays biological dependence on divalent ions for activity. PlyN74 and PlyTB40 have T7 lysozyme-type Amidase_2 and carboxypeptidase T-type Amidase_3 EADs, respectively, which are members of the MurNAc-LAA superfamily, but are not homologs and thus do not have a shared protein fold. All three endolysins contain similar SH3-family CBDs.

Although minor host range differences were noted, all three endolysins demonstrated broad antimicrobial activity against members of the *Bacillus cereus sensu lato* group with particularly high lytic activity against *B. cereus* ATCC 4342. Characterization studies determined the optimal lytic activity for these enzymes was at physiological pH (pH 7.0-8.0), over a broad temperature range (4° C.-55° C.), and at low concentrations of NaCl (<50 mM). Direct comparison of lytic activity shows the PlyP56 enzyme to be the most effective of the three at lysing the cell wall peptidoglycan, although all three exhibited significant lytic activity. This study thus demonstrates the efficacy of *Bacillus*-specific endolysins, including PlyP56, PlyN74 and PlyTB40, which contribute to the toolbox of EADs and CBDs for treating and/or preventing bacterial infection. In addition, the disclosed endolysins may be further modified or shuffled through chimeragenesis to create additional enzyme embodiments.

All identified publications and references mentioned in this specification are herein incorporated by reference to the same extent as if each individual publication was specifically and individually indicated to be incorporated by reference in its entirety. While the invention has been described

What is claimed is:

1. A method of treating a bacterial infection in a subject comprising administering to said subject a therapeutically effective amount of an isolated polypeptide comprising an amino acid sequence of SEQ ID NO:3, or variants thereof have at least about 90% identity thereto.

2. The method of claim 1, wherein said isolated polypeptide further comprises an amino acid sequence of SEQ ID NO:4.

3. The method of claim 1, comprising the further step of administering to said subject a secondary therapeutic agent after or concurrent with said administration of said isolated polypeptide.

4. The method of claim 3, wherein said secondary therapeutic agent is a holin protein or one or more antibiotic.

5. The method of claim 1, wherein said bacterial infection is caused by a *Bacillus* strain.

* * * * *

SEQUENCE LISTING

```
<160> NUMBER OF SEQ ID NOS: 44

<210> SEQ ID NO 1
<211> LENGTH: 798
<212> TYPE: DNA
<213> ORGANISM: Artificial Sequence
<220> FEATURE:
<223> OTHER INFORMATION: DNA sequence

<400> SEQUENCE: 1
atggcaatgg cactgcagac cctgattgat aaagcaaatc gcaaactgaa tattagcggc      60
atgcgtaaag atgttgcaga tcgtacccgt gcagttatta cccagatgca tgcacagggt     120
atctatattt gtgttgccca gggttttcgt agctttgcag aacaggatgc actgtatgcg     180
cagggtcgta ccaaaccggg taatattgtt accaatgcac gtggtggtca gagcaatcat     240
aactatggtg ttgcagttga tctgtgtctg tatacccagg atggtagtga tgttatttgg     300
accgttgaag gcaattttcg taaagttatt gcagccatga aaggccaggg ctttaaatgg     360
ggtggtgatt gggttagctt taaagattat ccgcacttcg aactgtatga tgttgttggt     420
ggccagaaac cgcctgcaga taatggtggt gccgttgata atggcggtgg tagcggtggt     480
tcaagtggtg gtagtaccgg tggtggcagc acaggtggcg attatgatag cagctggttt     540
accaaagaaa ccggcaccct taccaccaat accagcatta aactgcgtac cgcaccgttt     600
accagtgccg gtgttattgc aaccctgcct gcaggtagcg ttgttaacta taatggttat     660
ggcatcgagt atgatggcta tgtttggatt cgtcagcctc gtagcaatgg ctatggttat     720
ctggcaaccg gtgaaagcaa aggtggtaaa cgtcagaatt attgggcac gtttaaacat     780 catcaccatc accattaa                                                   798

<210> SEQ ID NO 2
<211> LENGTH: 259
<212> TYPE: PRT
<213> ORGANISM: Artificial Sequence
<220> FEATURE:
<223> OTHER INFORMATION: PlyP56 (amino acids 1-259)

<400> SEQUENCE: 2

Met Ala Met Ala Leu Gln Thr Leu Ile Asp Lys Ala Asn Arg Lys Leu
1               5                   10                  15

Asn Ile Ser Gly Met Arg Lys Asp Val Ala Asp Arg Thr Arg Ala Val
            20                  25                  30

Ile Thr Gln Met His Ala Gln Gly Ile Tyr Ile Cys Val Ala Gln Gly
        35                  40                  45

Phe Arg Ser Phe Ala Glu Gln Asp Ala Leu Tyr Ala Gln Gly Arg Thr
    50                  55                  60

Lys Pro Gly Asn Ile Val Thr Asn Ala Arg Gly Gly Gln Ser Asn His
65                  70                  75                  80

Asn Tyr Gly Val Ala Val Asp Leu Cys Leu Tyr Thr Gln Asp Gly Ser
                85                  90                  95

Asp Val Ile Trp Thr Val Glu Gly Asn Phe Arg Lys Val Ile Ala Ala
            100                 105                 110

Met Lys Gly Gln Gly Phe Lys Trp Gly Gly Asp Trp Val Ser Phe Lys
        115                 120                 125
```

Asp Tyr Pro His Phe Glu Leu Tyr Asp Val Val Gly Gln Lys Pro
130                 135                 140

Pro Ala Asp Asn Gly Gly Ala Val Asp Asn Gly Gly Ser Gly Gly
145                 150                 155                 160

Ser Ser Gly Gly Ser Thr Gly Gly Ser Thr Gly Gly Asp Tyr Asp
        165                 170                 175

Ser Ser Trp Phe Thr Lys Glu Thr Gly Thr Phe Thr Thr Asn Thr Ser
            180                 185                 190

Ile Lys Leu Arg Thr Ala Pro Phe Thr Ser Ala Gly Val Ile Ala Thr
        195                 200                 205

Leu Pro Ala Gly Ser Val Val Asn Tyr Asn Gly Tyr Gly Ile Glu Tyr
        210                 215                 220

Asp Gly Tyr Val Trp Ile Arg Gln Pro Arg Ser Asn Gly Tyr Gly Tyr
225                 230                 235                 240

Leu Ala Thr Gly Glu Ser Lys Gly Gly Lys Arg Gln Asn Tyr Trp Gly
            245                 250                 255

Thr Phe Lys

<210> SEQ ID NO 3
<211> LENGTH: 65
<212> TYPE: PRT
<213> ORGANISM: Artificial Sequence
<220> FEATURE:
<223> OTHER INFORMATION: PlyP56 EAD

<400> SEQUENCE: 3

Thr Asn Ala Arg Gly Gly Gln Ser Asn His Asn Tyr Gly Val Ala Val
1               5                   10                  15

Asp Leu Cys Leu Tyr Thr Gln Asp Gly Ser Asp Val Ile Trp Thr Val
            20                  25                  30

Glu Gly Asn Phe Arg Lys Val Ile Ala Ala Met Lys Gly Gln Gly Phe
        35                  40                  45

Lys Trp Gly Gly Asp Trp Val Ser Phe Lys Asp Tyr Pro His Phe Glu
50                  55                  60

Leu
65

<210> SEQ ID NO 4
<211> LENGTH: 65
<212> TYPE: PRT
<213> ORGANISM: Artificial Sequence
<220> FEATURE:
<223> OTHER INFORMATION: PlyP56 CBD

<400> SEQUENCE: 4

Glu Thr Gly Thr Phe Thr Thr Asn Thr Ser Ile Lys Leu Arg Thr Ala
1               5                   10                  15

Pro Phe Thr Ser Ala Gly Val Ile Ala Thr Leu Pro Ala Gly Ser Val
            20                  25                  30

Val Asn Tyr Asn Gly Tyr Gly Ile Glu Tyr Asp Gly Tyr Val Trp Ile
        35                  40                  45

Arg Gln Pro Arg Ser Asn Gly Tyr Gly Tyr Leu Ala Thr Gly Glu Ser
50                  55                  60

Lys
65

<210> SEQ ID NO 5

<211> LENGTH: 846
<212> TYPE: DNA
<213> ORGANISM: Artificial Sequence
<220> FEATURE:
<223> OTHER INFORMATION: PlyN74 DNA

<400> SEQUENCE: 5

```
atgaacatca acacccagta tctggttacc gatccggaac gtctgaaagt tattggtccg      60
aattggatga atccgaccga aattaccttt cacaacacct ataatgatgc aagcgcaagt     120
gccgaagttc gtaatgtgcg taataatagc accggcacca gctttcatac cgcagttgat     180
gattttgaag ttcagcaggt tgttccgttt gatcgtaatg catggcatgc cggtgatggc     240
acctatggtg caggtaatcg taatagcatt ggtgtggaaa tctgctatag tatgagcggt     300
ggtgaacgtt atcgtaaagc agaactgaat gccattgaac atattagcga tctgatggtg     360
cgttttggta ttccgattag caaagtgaaa acccatcaag aacgcaacgg taaatattgt     420
ccgcatcgta tgctggatga aggtcgtgtt ggttggttta agccgaatg tgaacgtcgt      480
gcaaatgaaa aacgtaatgg tggtggtggc accccgacac cgcctccgga accgaaaccg     540
gaacctaccc cgaaacctcc gagcggtgat tatgatagca gctggtttac caaagaaacc     600
ggcacctttg ttaccaacac cacaattaaa ctgcgtaccg caccgtttac ctcagccggt     660
gttattgcaa ccctgcctgc aggtagcacc gttaactata atggttttgg cattgagtat     720
gatggctatg tgtggattcg tcagcctcgt agcaatggtt atggttatct ggcaaccggt     780
gaaagcaaag tggtaaacg tgtgaattat tggggcacct ttaaacatca tcaccatcac     840
cactaa                                                                846
```

<210> SEQ ID NO 6
<211> LENGTH: 275
<212> TYPE: PRT
<213> ORGANISM: Artificial Sequence
<220> FEATURE:
<223> OTHER INFORMATION: PlyN74 Protein

<400> SEQUENCE: 6

```
Met Asn Ile Asn Thr Gln Tyr Leu Val Thr Asp Pro Glu Arg Leu Lys
1               5                   10                  15

Val Ile Gly Pro Asn Trp Met Asn Pro Thr Glu Ile Thr Phe His Asn
            20                  25                  30

Thr Tyr Asn Asp Ala Ser Ala Ser Ala Glu Val Arg Asn Val Arg Asn
        35                  40                  45

Asn Ser Thr Gly Thr Ser Phe His Thr Ala Val Asp Asp Phe Glu Val
    50                  55                  60

Gln Gln Val Val Pro Phe Asp Arg Asn Ala Trp His Ala Gly Asp Gly
65                  70                  75                  80

Thr Tyr Gly Ala Gly Asn Arg Asn Ser Ile Gly Val Glu Ile Cys Tyr
                85                  90                  95

Ser Met Ser Gly Gly Glu Arg Tyr Arg Lys Ala Glu Leu Asn Ala Ile
            100                 105                 110

Glu His Ile Ser Asp Leu Met Val Arg Phe Gly Ile Pro Ile Ser Lys
        115                 120                 125

Val Lys Thr His Gln Glu Arg Asn Gly Lys Tyr Cys Pro His Arg Met
    130                 135                 140

Leu Asp Glu Gly Arg Val Gly Trp Phe Lys Ala Glu Cys Glu Arg Arg
145                 150                 155                 160

Ala Asn Glu Lys Arg Asn Gly Gly Gly Gly Thr Pro Thr Pro Pro Pro
```

```
                165                 170                 175
Glu Pro Lys Pro Glu Pro Thr Pro Lys Pro Ser Gly Asp Tyr Asp
            180                 185                 190

Ser Ser Trp Phe Thr Lys Glu Thr Gly Thr Phe Val Thr Asn Thr Thr
        195                 200                 205

Ile Lys Leu Arg Thr Ala Pro Phe Thr Ser Ala Gly Val Ile Ala Thr
210                 215                 220

Leu Pro Ala Gly Ser Thr Val Asn Tyr Asn Gly Phe Gly Ile Glu Tyr
225                 230                 235                 240

Asp Gly Tyr Val Trp Ile Arg Gln Pro Arg Ser Asn Gly Tyr Gly Tyr
                245                 250                 255

Leu Ala Thr Gly Glu Ser Lys Gly Gly Lys Arg Val Asn Tyr Trp Gly
            260                 265                 270

Thr Phe Lys
        275

<210> SEQ ID NO 7
<211> LENGTH: 119
<212> TYPE: PRT
<213> ORGANISM: Artificial Sequence
<220> FEATURE:
<223> OTHER INFORMATION: PlyN74 EAD

<400> SEQUENCE: 7

Met Asn Pro Thr Glu Ile Thr Phe His Asn Thr Tyr Asn Asp Ala Ser
1               5                   10                  15

Ala Ser Ala Glu Val Arg Asn Val Arg Asn Asn Ser Thr Gly Thr Ser
            20                  25                  30

Phe His Thr Ala Val Asp Asp Phe Glu Val Gln Gln Val Val Pro Phe
        35                  40                  45

Asp Arg Asn Ala Trp His Ala Gly Asp Gly Thr Tyr Gly Ala Gly Asn
    50                  55                  60

Arg Asn Ser Ile Gly Val Glu Ile Cys Tyr Ser Met Ser Gly Gly Glu
65                  70                  75                  80

Arg Tyr Arg Lys Ala Glu Leu Asn Ala Ile Glu His Ile Ser Asp Leu
                85                  90                  95

Met Val Arg Phe Gly Ile Pro Ile Ser Lys Val Lys Thr His Gln Glu
            100                 105                 110

Arg Asn Gly Lys Tyr Cys Pro
        115

<210> SEQ ID NO 8
<211> LENGTH: 65
<212> TYPE: PRT
<213> ORGANISM: Artificial Sequence
<220> FEATURE:
<223> OTHER INFORMATION: PlyN74 CBD

<400> SEQUENCE: 8

Glu Thr Gly Thr Phe Val Thr Asn Thr Thr Ile Lys Leu Arg Thr Ala
1               5                   10                  15

Pro Phe Thr Ser Ala Gly Val Ile Ala Thr Leu Pro Ala Gly Ser Thr
            20                  25                  30

Val Asn Tyr Asn Gly Phe Gly Ile Glu Tyr Asp Gly Tyr Val Trp Ile
        35                  40                  45

Arg Gln Pro Arg Ser Asn Gly Tyr Gly Tyr Leu Ala Thr Gly Glu Ser
    50                  55                  60
```

Lys
65

<210> SEQ ID NO 9
<211> LENGTH: 837
<212> TYPE: DNA
<213> ORGANISM: Artificial Sequence
<220> FEATURE:
<223> OTHER INFORMATION: PlyTB40 DNA

<400> SEQUENCE: 9

```
atgggcacct ataatgttca tggtggccat aatagcattg ttcagggtgc aaattatggc    60
aaccgtaaag aacatgttat ggatcgtcag gttaaagatg ccctgattag caaactgcgt   120
agcctgggtc ataccgttta tgattgtacc gatgaaaccg gtagcaccca gagcgcaaat   180
ctgcgtaata ttgttgcaaa atgtaatgcc catcgtgtgg atctggatat tagcctgcat   240
ctgaatgcat ataatggtag cgcaagcggt gttgaagtgt gttattatga tcagcaggca   300
ctggcagcaa aagttagcaa acagctgagt gatgatattg gttggagcaa tcgtggtgca   360
aaaccgcgta ccgatctgta tgttctgaat agcaccagcg caccggcaat tctgattgaa   420
ctgggttttta ttgataacga gagcgatatg gccaaatgga acgttgataa aattgccgat   480
agcatctgct atgcaattac cggtcagcgt accggcagca ccggtggtag taccggtggt   540
tcaaccggtg gctctacagg tggtggtggt tatgatagca gctggtttac accgcagaat   600
ggtgttttta ccgcaaacac caccattaaa gttcgtagcg aaccgagcgt taatgcaacc   660
catctgcgta ccctgtatag cggtggcacc tttacctata ccagctttgg tatggaaaaa   720
gatggctatg tgtggattaa aggtgttgat ggcacctatg ttgcaaccgg tgaaaccagt   780
gatggtaaac gtattagcta ttggggcacc tttcagcatc atcatcacca tcattaa      837
```

<210> SEQ ID NO 10
<211> LENGTH: 272
<212> TYPE: PRT
<213> ORGANISM: Artificial Sequence
<220> FEATURE:
<223> OTHER INFORMATION: PlyTB40 Protein

<400> SEQUENCE: 10

Met Gly Thr Tyr Asn Val His Gly Gly His Asn Ser Ile Val Gln Gly
1               5                   10                  15

Ala Asn Tyr Gly Asn Arg Lys Glu His Val Met Asp Arg Gln Val Lys
            20                  25                  30

Asp Ala Leu Ile Ser Lys Leu Arg Ser Leu Gly His Thr Val Tyr Asp
        35                  40                  45

Cys Thr Asp Glu Thr Gly Ser Thr Gln Ser Ala Asn Leu Arg Asn Ile
    50                  55                  60

Val Ala Lys Cys Asn Ala His Arg Val Asp Leu Asp Ile Ser Leu His
65                  70                  75                  80

Leu Asn Ala Tyr Asn Gly Ser Ala Ser Gly Val Glu Val Cys Tyr Tyr
                85                  90                  95

Asp Gln Gln Ala Leu Ala Ala Lys Val Ser Lys Gln Leu Ser Asp Asp
            100                 105                 110

Ile Gly Trp Ser Asn Arg Gly Ala Lys Pro Arg Thr Asp Leu Tyr Val
        115                 120                 125

Leu Asn Ser Thr Ser Ala Pro Ala Ile Leu Ile Glu Leu Gly Phe Ile
    130                 135                 140

Asp Asn Glu Ser Asp Met Ala Lys Trp Asn Val Asp Lys Ile Ala Asp

```
            145                 150                 155                 160
Ser Ile Cys Tyr Ala Ile Thr Gly Gln Arg Thr Gly Ser Thr Gly Gly
                165                 170                 175

Ser Thr Gly Gly Ser Thr Gly Gly Ser Thr Gly Gly Gly Tyr Asp
            180                 185                 190

Ser Ser Trp Phe Thr Pro Gln Asn Gly Val Phe Thr Ala Asn Thr Thr
                195                 200                 205

Ile Lys Val Arg Ser Glu Pro Ser Val Asn Ala Thr His Leu Arg Thr
            210                 215                 220

Leu Tyr Ser Gly Gly Thr Phe Thr Tyr Thr Ser Phe Gly Met Glu Lys
225                 230                 235                 240

Asp Gly Tyr Val Trp Ile Lys Gly Val Asp Gly Thr Tyr Val Ala Thr
                245                 250                 255

Gly Glu Thr Ser Asp Gly Lys Arg Ile Ser Tyr Trp Gly Thr Phe Gln
            260                 265                 270

<210> SEQ ID NO 11
<211> LENGTH: 159
<212> TYPE: PRT
<213> ORGANISM: Artificial Sequence
<220> FEATURE:
<223> OTHER INFORMATION: PlyTB40 EAD

<400> SEQUENCE: 11

Gly His Asn Ser Ile Val Gln Gly Ala Asn Tyr Gly Asn Arg Lys Glu
1               5                   10                  15

His Val Met Asp Arg Gln Val Lys Asp Ala Leu Ile Ser Lys Leu Arg
            20                  25                  30

Ser Leu Gly His Thr Val Tyr Asp Cys Thr Asp Glu Thr Gly Ser Thr
        35                  40                  45

Gln Ser Ala Asn Leu Arg Asn Ile Val Ala Lys Cys Asn Ala His Arg
    50                  55                  60

Val Asp Leu Asp Ile Ser Leu His Leu Asn Ala Tyr Asn Gly Ser Ala
65                  70                  75                  80

Ser Gly Val Glu Val Cys Tyr Tyr Asp Gln Gln Ala Leu Ala Ala Lys
                85                  90                  95

Val Ser Lys Gln Leu Ser Asp Asp Ile Gly Trp Ser Asn Arg Gly Ala
            100                 105                 110

Lys Pro Arg Thr Asp Leu Tyr Val Leu Asn Ser Thr Ser Ala Pro Ala
        115                 120                 125

Ile Leu Ile Glu Leu Gly Phe Ile Asp Asn Glu Ser Asp Met Ala Lys
    130                 135                 140

Trp Asn Val Asp Lys Ile Ala Asp Ser Ile Cys Tyr Ala Ile Thr
145                 150                 155

<210> SEQ ID NO 12
<211> LENGTH: 56
<212> TYPE: PRT
<213> ORGANISM: Artificial Sequence
<220> FEATURE:
<223> OTHER INFORMATION: PlyTB40 CBD

<400> SEQUENCE: 12

Trp Phe Thr Pro Gln Asn Gly Val Phe Thr Ala Asn Thr Thr Ile Lys
1               5                   10                  15

Val Arg Ser Glu Pro Ser Val Asn Ala Thr His Leu Thr Leu Tyr
            20                  25                  30
```

```
Ser Gly Gly Thr Phe Thr Tyr Thr Ser Phe Gly Met Glu Lys Asp Gly
        35                  40                  45

Tyr Val Trp Ile Lys Gly Val Asp
    50                  55

<210> SEQ ID NO 13
<211> LENGTH: 762
<212> TYPE: DNA
<213> ORGANISM: Artificial Sequence
<220> FEATURE:
<223> OTHER INFORMATION: PlyA92 DNA

<400> SEQUENCE: 13
atgaccatgt attactatga gcgcaacctg aaaaacatta atcagctggc agataatacc      60
aaagcagcag cactgaaact gctggattat gccgaaaaaa acaaaattgg cgtgctgatc     120
tatgaaacca ttcgtagcaa agcacagcag gcacagaatg ttaaaaatgg tgcaagccag     180
accatgaaca gctatcatat tgttggtcag gcactggatt ttgtttatac cggtggttat     240
gataaaagca gcaccctgtg gaatggctat gaaaaaccgg aagccaaaaa attcattgcc     300
tatgcaaaac agctgggctt taaatggggt ggtgattgga gcaaatttgt ggataaaccg     360
catctggaat ttccgtataa aggttatggc accgataccc ttggtaaaaa agccgcaccg     420
gttaaaaccg gcaccgcaac caaaccggca aaaactccgg caaaaccgaa accgagcacc     480
agcaaaagca atataaacct gccgagcggt atctataaag ttaaacaccc gctgatgaaa     540
ggcagcgcag ttaaagcaat tcaagaagca ctggcaagca tctatttcta tccggaaaaa     600
ggtgccaaaa acaatggcat cgatggttat tatggtccga aaaccgcaga tgcagttaaa     660
cgttttcaga gcgttagcgg tctgcctgca gatggtattt atggccctaa aaccaaagaa     720
gccatcgaaa aaaaactgaa acatcaccat caccaccatt aa                        762

<210> SEQ ID NO 14
<211> LENGTH: 247
<212> TYPE: PRT
<213> ORGANISM: Artificial Sequence
<220> FEATURE:
<223> OTHER INFORMATION: PlyA92 Protein

<400> SEQUENCE: 14

Met Thr Met Tyr Tyr Tyr Glu Arg Asn Leu Lys Asn Ile Asn Gln Leu
1               5                   10                  15

Ala Asp Asn Thr Lys Ala Ala Ala Leu Lys Leu Leu Asp Tyr Ala Glu
            20                  25                  30

Lys Asn Lys Ile Gly Val Leu Ile Tyr Glu Thr Ile Arg Ser Lys Ala
        35                  40                  45

Gln Gln Ala Gln Asn Val Lys Asn Gly Ala Ser Gln Thr Met Asn Ser
    50                  55                  60

Tyr His Ile Val Gly Gln Ala Leu Asp Phe Val Tyr Thr Gly Gly Tyr
65                  70                  75                  80

Asp Lys Ser Ser Thr Leu Trp Asn Gly Tyr Glu Lys Pro Glu Ala Lys
                85                  90                  95

Lys Phe Ile Ala Tyr Ala Lys Gln Leu Gly Phe Lys Trp Gly Gly Asp
            100                 105                 110

Trp Ser Lys Phe Val Asp Lys Pro His Leu Glu Phe Pro Tyr Lys Gly
        115                 120                 125

Tyr Gly Thr Asp Thr Phe Gly Lys Lys Ala Ala Pro Val Lys Thr Gly
    130                 135                 140
```

```
Thr Ala Thr Lys Pro Ala Lys Thr Pro Ala Lys Pro Lys Pro Ser Thr
145                 150                 155                 160

Ser Lys Ser Lys Tyr Asn Leu Pro Ser Gly Ile Tyr Val Lys Thr
                165                 170                 175

Pro Leu Met Lys Gly Ser Ala Val Lys Ala Ile Gln Glu Ala Leu Ala
            180                 185                 190

Ser Ile Tyr Phe Tyr Pro Glu Lys Gly Ala Lys Asn Asn Gly Ile Asp
        195                 200                 205

Gly Tyr Tyr Gly Pro Lys Thr Ala Asp Ala Val Lys Arg Phe Gln Ser
    210                 215                 220

Val Ser Gly Leu Pro Ala Asp Gly Ile Tyr Gly Pro Lys Thr Lys Glu
225                 230                 235                 240

Ala Ile Glu Lys Lys Leu Lys
                245

<210> SEQ ID NO 15
<211> LENGTH: 103
<212> TYPE: PRT
<213> ORGANISM: Artificial Sequence
<220> FEATURE:
<223> OTHER INFORMATION: PlyA92 EAD

<400> SEQUENCE: 15

Ile Asn Gln Leu Ala Asp Asn Thr Lys Ala Ala Leu Lys Leu Leu
1               5                   10                  15

Asp Tyr Ala Glu Lys Asn Lys Ile Gly Val Leu Ile Tyr Glu Thr Ile
            20                  25                  30

Arg Ser Lys Ala Gln Gln Ala Gln Asn Val Lys Asn Gly Ala Ser Gln
        35                  40                  45

Thr Met Asn Ser Tyr His Ile Val Gly Gln Ala Leu Asp Phe Val Tyr
    50                  55                  60

Thr Gly Gly Tyr Asp Lys Ser Ser Thr Leu Trp Asn Gly Tyr Glu Lys
65                  70                  75                  80

Pro Glu Ala Lys Lys Phe Ile Ala Tyr Ala Lys Gln Leu Gly Phe Lys
                85                  90                  95

Trp Gly Gly Asp Trp Ser Lys
            100

<210> SEQ ID NO 16
<211> LENGTH: 63
<212> TYPE: PRT
<213> ORGANISM: Artificial Sequence
<220> FEATURE:
<223> OTHER INFORMATION: PlyA92 CBD

<400> SEQUENCE: 16

Lys Gly Ser Ala Val Lys Ala Ile Gln Glu Ala Leu Ala Ser Ile Tyr
1               5                   10                  15

Phe Tyr Pro Glu Lys Gly Ala Lys Asn Asn Gly Ile Asp Gly Tyr Tyr
            20                  25                  30

Gly Pro Lys Thr Ala Asp Ala Val Lys Arg Phe Gln Ser Val Ser Gly
        35                  40                  45

Leu Pro Ala Asp Gly Ile Tyr Gly Pro Lys Thr Lys Glu Ala Ile
    50                  55                  60

<210> SEQ ID NO 17
<211> LENGTH: 1050
<212> TYPE: DNA
<213> ORGANISM: Artificial Sequence
```

<220> FEATURE:
<223> OTHER INFORMATION: PlyP108 DNA

<400> SEQUENCE: 17

```
atgggtgcac cgtttaccct gcaagaactg attgataaaa gcaataaacg tctgggtgtt      60
agcggtctga ataaagttgt ttatgaaagc gccatcgaag tgatcaaacg tgcatataaa     120
gaaggcatct gggttcagta tagcgcaggt tatcgtagct atgcagaaca gaatgcactg     180
tatgcacagg gtcgtaccaa accgggtagc attgttacca atgcacgtgg tggttatagc     240
aatcataatt ttggtctggc cgtggactat ttcctgtatg atgataatgg taaagcccac     300
tggaatgtga atagcgattg gaaacgtgtt gcacagattg caaagatct  gggttttgaa     360
tggggtggtg attggaaatc attttatgat gcaccgcatc tggaaatgac cggtggtctg     420
agcaccgcac agctgcgtgc aggtaaacgt ccgaaactgg ttagcaaagt taaaaatccg     480
gtgagcaaac cgagcaccag cagcagcagt agcggtagca gcaaaaaaaa ctatctgagc     540
aaaggtgata atagcagcgc agttaaaacc atgcaagaaa aactgaatgc agccggtttt     600
agcgttggta agcagatgg tattttttggt gcaaaaaccg aaagcgcact gaaagcattt     660
cagaaaagcg tgggtattag cgcagatggt ctgtatggtc cgaccagcaa agcaaaactg     720
gaaagctaca aaaaaccgtc cagctccaaa aaaagcaaag gcaccattgt tctgccgaaa     780
ggtgttgtta gcagcggtag ctcacatagc gatatcaaaa atgtgcagac cgcaaccagc     840
gcactgtatt tttacccgga taaggtgcc  aaaaacaatg gcattgatgg ttattggggt     900
ccgaaaaccc aggatgcaat tcgtcgttat cagagcacca aaagtggtct gaaaaccgat     960
ggcatctatg gtccggcaac ccgtaaagca ctggaaaaag acctgaaaga agcaggctat    1020
accgttaaac atcatcacca tcaccactaa                                    1050
```

<210> SEQ ID NO 18
<211> LENGTH: 343
<212> TYPE: PRT
<213> ORGANISM: Artificial Sequence
<220> FEATURE:
<223> OTHER INFORMATION: PlyP108 Protein

<400> SEQUENCE: 18

```
Met Gly Ala Pro Phe Thr Leu Gln Glu Leu Ile Asp Lys Ser Asn Lys
1               5                   10                  15

Arg Leu Gly Val Ser Gly Leu Asn Lys Val Val Tyr Glu Ser Ala Ile
            20                  25                  30

Glu Val Ile Lys Arg Ala Tyr Lys Glu Gly Ile Trp Val Gln Tyr Ser
        35                  40                  45

Ala Gly Tyr Arg Ser Tyr Ala Glu Gln Asn Ala Leu Tyr Ala Gln Gly
    50                  55                  60

Arg Thr Lys Pro Gly Ser Ile Val Thr Asn Ala Arg Gly Gly Tyr Ser
65                  70                  75                  80

Asn His Asn Phe Gly Leu Ala Val Asp Tyr Phe Leu Tyr Asp Asp Asn
                85                  90                  95

Gly Lys Ala His Trp Asn Val Asn Ser Asp Trp Lys Arg Val Ala Gln
            100                 105                 110

Ile Ala Lys Asp Leu Gly Phe Glu Trp Gly Gly Asp Trp Lys Ser Phe
        115                 120                 125

Tyr Asp Ala Pro His Leu Glu Met Thr Gly Gly Leu Ser Thr Ala Gln
    130                 135                 140

Leu Arg Ala Gly Lys Arg Pro Lys Leu Val Ser Lys Val Lys Asn Pro
```

```
                145                 150                 155                 160
Val Ser Lys Pro Ser Thr Ser Ser Ser Ser Gly Ser Ser Lys Lys
                165                 170                 175

Asn Tyr Leu Ser Lys Gly Asp Asn Ser Ser Ala Val Lys Thr Met Gln
                180                 185                 190

Glu Lys Leu Asn Ala Ala Gly Phe Ser Val Gly Lys Ala Asp Gly Ile
            195                 200                 205

Phe Gly Ala Lys Thr Glu Ser Ala Leu Lys Ala Phe Gln Lys Ser Val
        210                 215                 220

Gly Ile Ser Ala Asp Gly Leu Tyr Gly Pro Thr Ser Lys Ala Lys Leu
225                 230                 235                 240

Glu Ser Tyr Lys Lys Pro Ser Ser Lys Ser Lys Gly Thr Ile
                245                 250                 255

Val Leu Pro Lys Gly Val Val Ser Gly Ser Ser His Ser Asp Ile
                260                 265                 270

Lys Asn Val Gln Thr Ala Thr Ser Ala Leu Tyr Phe Tyr Pro Asp Lys
                275                 280                 285

Gly Ala Lys Asn Asn Gly Ile Asp Gly Tyr Trp Gly Pro Lys Thr Gln
            290                 295                 300

Asp Ala Ile Arg Arg Tyr Gln Ser Thr Lys Ser Gly Leu Lys Thr Asp
305                 310                 315                 320

Gly Ile Tyr Gly Pro Ala Thr Arg Lys Ala Leu Glu Lys Asp Leu Lys
                325                 330                 335

Glu Ala Gly Tyr Thr Val Lys
                340
```

<210> SEQ ID NO 19
<211> LENGTH: 108
<212> TYPE: PRT
<213> ORGANISM: Artificial Sequence
<220> FEATURE:
<223> OTHER INFORMATION: PlyP108 EAD

<400> SEQUENCE: 19

```
Ser Gly Leu Asn Lys Val Val Tyr Glu Ser Ala Ile Glu Val Ile Lys
1               5                   10                  15

Arg Ala Tyr Lys Glu Gly Ile Trp Val Gln Tyr Ser Ala Gly Tyr Arg
                20                  25                  30

Ser Tyr Ala Glu Gln Asn Ala Leu Tyr Ala Gln Gly Arg Thr Lys Pro
            35                  40                  45

Gly Ser Ile Val Thr Asn Ala Arg Gly Gly Tyr Ser Asn His Asn Phe
        50                  55                  60

Gly Leu Ala Val Asp Tyr Phe Leu Tyr Asp Asp Asn Gly Lys Ala His
65                  70                  75                  80

Trp Asn Val Asn Ser Asp Trp Lys Arg Val Ala Gln Ile Ala Lys Asp
                85                  90                  95

Leu Gly Phe Glu Trp Gly Gly Asp Trp Lys Ser Phe
                100                 105
```

<210> SEQ ID NO 20
<211> LENGTH: 57
<212> TYPE: PRT
<213> ORGANISM: Artificial Sequence
<220> FEATURE:
<223> OTHER INFORMATION: PlyP108 CBD1

<400> SEQUENCE: 20

-continued

Asn Ser Ser Ala Val Lys Thr Met Gln Glu Lys Leu Asn Ala Ala Gly
1               5                   10                  15

Phe Ser Val Gly Lys Ala Asp Gly Ile Phe Gly Ala Lys Thr Glu Ser
                20                  25                  30

Ala Leu Lys Ala Phe Gln Lys Ser Val Gly Ile Ser Ala Asp Gly Leu
            35                  40                  45

Tyr Gly Pro Thr Ser Lys Ala Lys Leu
        50                  55

<210> SEQ ID NO 21
<211> LENGTH: 74
<212> TYPE: PRT
<213> ORGANISM: Artificial Sequence
<220> FEATURE:
<223> OTHER INFORMATION: PlyP108 CBD2

<400> SEQUENCE: 21

Ser His Ser Asp Ile Lys Asn Val Gln Thr Ala Thr Ser Ala Leu Tyr
1               5                   10                  15

Phe Tyr Pro Asp Lys Gly Ala Lys Asn Asn Gly Ile Asp Gly Tyr Trp
                20                  25                  30

Gly Pro Lys Thr Gln Asp Ala Ile Arg Arg Tyr Gln Ser Thr Lys Ser
            35                  40                  45

Gly Leu Lys Thr Asp Gly Ile Tyr Gly Pro Ala Thr Arg Lys Ala Leu
        50                  55                  60

Glu Lys Asp Leu Lys Glu Ala Gly Tyr Thr
65                  70

<210> SEQ ID NO 22
<211> LENGTH: 816
<212> TYPE: DNA
<213> ORGANISM: Artificial Sequence
<220> FEATURE:
<223> OTHER INFORMATION: PlyS31 DNA

<400> SEQUENCE: 22
atgggcaaca ttgtggatat cagcaaatgg aatggtgata tcaattggga taccgccaaa      60
ccgtatatcg attttatcat tgcacgtgtt caggatggta gcaattatcg tgatccgcgt    120
tataatggtt atgtggcaga tatgaaacgc aaaggtattc cgtttggcaa ttatgccttt    180
tgccgttttg tgagcattaa cgatgcaaaa aagaagccc aggattttg ggatcgtggt      240
gataaaagca gcaccgtttg ggttgcagat gttgaagtta aaccatgga tgatatgcgt     300
gcaggcaccc aggcatttat tgatgaactg cgtcgtctgg gtgccaaaaa agttggtctg    360
tatgttggtc atcacatgta tgaaagcttt ggtatgagcc aggttcagag cgattttgtt    420
tggattcctc gttatggtgg tagcaaaccg aaatatccgt gtgatatttg cagtatacc    480
gaaaccggtc ataccggg tattggtaaa tgtgatctga accagctgat tggcagcaaa     540
aatctggcat attttaccgg tcaggatgat cagaccccga aggttatca gtatgttcgt    600
agcggtggtc tgggtagcag cctgattaaa gaagttagca tcaaaatgaa cgaactgggc    660
attaaaggtc gcattattct gaatccgagc gaaggtctgg catttatgca gaccgatgtt    720
ctgccgaatg tgaactgga taaaatcacc agttggttcg atgaaaaagg ttggtggtat    780
gaatatatcc agggtcatca tcatcaccat cattaa                              816

<210> SEQ ID NO 23
<211> LENGTH: 265
<212> TYPE: PRT

<213> ORGANISM: Artificial Sequence
<220> FEATURE:
<223> OTHER INFORMATION: PlyS31 Protein

<400> SEQUENCE: 23

```
Met Gly Asn Ile Val Asp Ile Ser Lys Trp Asn Gly Asp Ile Asn Trp
1               5                   10                  15

Asp Thr Ala Lys Pro Tyr Ile Asp Phe Ile Ile Ala Arg Val Gln Asp
            20                  25                  30

Gly Ser Asn Tyr Arg Asp Pro Arg Tyr Asn Gly Tyr Val Ala Asp Met
        35                  40                  45

Lys Arg Lys Gly Ile Pro Phe Gly Asn Tyr Ala Phe Cys Arg Phe Val
50                  55                  60

Ser Ile Asn Asp Ala Lys Lys Glu Ala Gln Asp Phe Trp Asp Arg Gly
65                  70                  75                  80

Asp Lys Ser Ser Thr Val Trp Val Ala Asp Val Glu Val Lys Thr Met
                85                  90                  95

Asp Asp Met Arg Ala Gly Thr Gln Ala Phe Ile Asp Glu Leu Arg Arg
            100                 105                 110

Leu Gly Ala Lys Lys Val Gly Leu Tyr Val Gly His His Met Tyr Glu
        115                 120                 125

Ser Phe Gly Met Ser Gln Val Gln Ser Asp Phe Val Trp Ile Pro Arg
130                 135                 140

Tyr Gly Gly Ser Lys Pro Lys Tyr Pro Cys Asp Ile Trp Gln Tyr Thr
145                 150                 155                 160

Glu Thr Gly His Thr Pro Gly Ile Gly Lys Cys Asp Leu Asn Gln Leu
                165                 170                 175

Ile Gly Ser Lys Asn Leu Ala Tyr Phe Thr Gly Gln Asp Asp Gln Thr
            180                 185                 190

Pro Lys Gly Tyr Gln Tyr Val Arg Ser Gly Leu Gly Ser Ser Leu
        195                 200                 205

Ile Lys Glu Val Ser Ile Lys Met Asn Glu Leu Gly Ile Lys Gly Arg
210                 215                 220

Ile Ile Leu Asn Pro Ser Glu Gly Leu Ala Phe Met Gln Thr Asp Val
225                 230                 235                 240

Leu Pro Asn Gly Glu Leu Asp Lys Ile Thr Ser Trp Phe Asp Glu Lys
                245                 250                 255

Gly Trp Trp Tyr Glu Tyr Ile Gln Gly
                260                 265
```

<210> SEQ ID NO 24
<211> LENGTH: 164
<212> TYPE: PRT
<213> ORGANISM: Artificial Sequence
<220> FEATURE:
<223> OTHER INFORMATION: PlyS31 EAD

<400> SEQUENCE: 24

```
Val Asp Ile Ser Lys Trp Asn Gly Asp Ile Asn Trp Asp Thr Ala Lys
1               5                   10                  15

Pro Tyr Ile Asp Phe Ile Ile Ala Arg Val Gln Asp Gly Ser Asn Tyr
            20                  25                  30

Arg Asp Pro Arg Tyr Asn Gly Tyr Val Ala Asp Met Lys Arg Lys Gly
        35                  40                  45

Ile Pro Phe Gly Asn Tyr Ala Phe Cys Arg Phe Val Ser Ile Asn Asp
50                  55                  60
```

```
Ala Lys Lys Glu Ala Gln Asp Phe Trp Asp Arg Gly Asp Lys Ser Ser
 65                  70                  75                  80

Thr Val Trp Val Ala Asp Val Glu Val Lys Thr Met Asp Met Arg
                 85                  90                  95

Ala Gly Thr Gln Ala Phe Ile Asp Glu Leu Arg Arg Leu Gly Ala Lys
            100                 105                 110

Lys Val Gly Leu Tyr Val Gly His His Met Tyr Glu Ser Phe Gly Met
        115                 120                 125

Ser Gln Val Gln Ser Asp Phe Val Trp Ile Pro Arg Tyr Gly Gly Ser
    130                 135                 140

Lys Pro Lys Tyr Pro Cys Asp Ile Trp Gln Tyr Thr Glu Thr Gly His
145                 150                 155                 160

Thr Pro Gly Ile
```

<210> SEQ ID NO 25
<211> LENGTH: 45
<212> TYPE: PRT
<213> ORGANISM: Artificial Sequence
<220> FEATURE:
<223> OTHER INFORMATION: PlyS31 CBD

<400> SEQUENCE: 25

```
Glu Leu Gly Ile Lys Gly Arg Ile Ile Leu Asn Pro Ser Glu Gly Leu
1                5                  10                  15

Ala Phe Met Gln Thr Asp Val Leu Pro Asn Gly Glu Leu Asp Lys Ile
                20                  25                  30

Thr Ser Trp Phe Asp Glu Lys Gly Trp Trp Tyr Glu Tyr
            35                  40                  45
```

<210> SEQ ID NO 26
<211> LENGTH: 918
<212> TYPE: DNA
<213> ORGANISM: Artificial Sequence
<220> FEATURE:
<223> OTHER INFORMATION: PlyT31 DNA

<400> SEQUENCE: 26

| | | |
|---|---|---|
| atgaaaaaag ttaccctgga tgcaggtcat ggtggtaaag atccgggtgc agttggtaat | 60 |
| ggtctgaaag aaaaagatct gaccctggaa attgccaaac agaccaaaag ctatctggaa | 120 |
| agcaattata gcggtgttag cgttcagctg acccgtagca ccgataaatt tctggaactg | 180 |
| ccggaacgtg cagcaattgc caataaaaac aaaagcgacc tgtttgtgag catccatatt | 240 |
| aacagtgccg gtggcaccaa tggcaccggt tttgaaaccc tgacctataa caaactgagc | 300 |
| gcaaaaagcc cgaccaaaag tgatcagaaa gttctgcatg caagcatcct gaatgaaatt | 360 |
| gcaagctttg gtgttgccaa ccgtaaagag aaagcagacg atctgagcgt tctgcgtaat | 420 |
| accaatatga gcgcaattct gaccgaaagc ctgtttatta caatccggc agatgcaaaa | 480 |
| ctgctgaaag ataaatcatt tgtgaaagcc gttagcgtgg tcatgcaaa aggtattgca | 540 |
| aaagttctgg gcctgaaagc aaaaaaagca ccggaaagtc cggttaaagc accgagcaaa | 600 |
| ccgagcaccc cgaaaggtga tacctataaa gttcagaaag cgataccct gtatggtatt | 660 |
| gcacgtcagc atggtatgag cgttgatgat ctgaaaaaac tgaatggcct gaaaagcgat | 720 |
| attattcgtg ttggtcagac cctgaaagtt aaacagagca gcgttacgta taagtgaaa | 780 |
| aaaggtgaca cgctgtacgg cattgccaaa gatcatggca ccaccgttgc aaatatcaaa | 840 |
| aaactgaaca atctgaaatc cgacctgatc aatattggtg ataccctgcg tgttaaacat | 900 |

-continued

```
catcatcacc atcactaa                                                   918
```

<210> SEQ ID NO 27
<211> LENGTH: 299
<212> TYPE: PRT
<213> ORGANISM: Artificial Sequence
<220> FEATURE:
<223> OTHER INFORMATION: PlyT31 Protein

<400> SEQUENCE: 27

Met Lys Lys Val Thr Leu Asp Ala Gly His Gly Gly Lys Asp Pro Gly
1               5                   10                  15

Ala Val Gly Asn Gly Leu Lys Glu Lys Asp Leu Thr Leu Glu Ile Ala
            20                  25                  30

Lys Gln Thr Lys Ser Tyr Leu Glu Ser Asn Tyr Ser Gly Val Ser Val
        35                  40                  45

Gln Leu Thr Arg Ser Thr Asp Lys Phe Leu Glu Leu Pro Glu Arg Ala
    50                  55                  60

Ala Ile Ala Asn Lys Asn Lys Ser Asp Leu Phe Val Ser Ile His Ile
65                  70                  75                  80

Asn Ser Ala Gly Gly Thr Asn Gly Thr Gly Phe Glu Thr Leu Thr Tyr
                85                  90                  95

Asn Lys Leu Ser Ala Lys Ser Pro Thr Lys Ser Asp Gln Lys Val Leu
            100                 105                 110

His Ala Ser Ile Leu Asn Glu Ile Ala Ser Phe Gly Val Ala Asn Arg
        115                 120                 125

Lys Glu Lys Ala Asp Asp Leu Ser Val Leu Arg Asn Thr Asn Met Ser
    130                 135                 140

Ala Ile Leu Thr Glu Ser Leu Phe Ile Asn Asn Pro Ala Asp Ala Lys
145                 150                 155                 160

Leu Leu Lys Asp Lys Ser Phe Val Lys Ala Val Ser Val Gly His Ala
                165                 170                 175

Lys Gly Ile Ala Lys Val Leu Gly Leu Lys Ala Lys Lys Ala Pro Glu
            180                 185                 190

Ser Pro Val Lys Ala Pro Ser Lys Pro Ser Thr Pro Lys Gly Asp Thr
        195                 200                 205

Tyr Lys Val Gln Lys Gly Asp Thr Leu Tyr Gly Ile Ala Arg Gln His
    210                 215                 220

Gly Met Ser Val Asp Asp Leu Lys Lys Leu Asn Gly Leu Lys Ser Asp
225                 230                 235                 240

Ile Ile Arg Val Gly Gln Thr Leu Lys Val Lys Gln Ser Ser Val Thr
                245                 250                 255

Tyr Lys Val Lys Lys Gly Asp Thr Leu Tyr Gly Ile Ala Lys Asp His
            260                 265                 270

Gly Thr Thr Val Ala Asn Ile Lys Lys Leu Asn Asn Leu Lys Ser Asp
        275                 280                 285

Leu Ile Asn Ile Gly Asp Thr Leu Arg Val Lys
    290                 295

<210> SEQ ID NO 28
<211> LENGTH: 117
<212> TYPE: PRT
<213> ORGANISM: Artificial Sequence
<220> FEATURE:
<223> OTHER INFORMATION: PlyT31 EAD

<400> SEQUENCE: 28

Ala Ala Ile Ala Asn Lys Asn Lys Ser Asp Leu Phe Val Ser Ile His
1               5                   10                  15

Ile Asn Ser Ala Gly Gly Thr Asn Gly Thr Gly Phe Glu Thr Leu Thr
            20                  25                  30

Tyr Asn Lys Leu Ser Ala Lys Ser Pro Thr Lys Ser Asp Gln Lys Val
        35                  40                  45

Leu His Ala Ser Ile Leu Asn Glu Ile Ala Ser Phe Gly Val Ala Asn
    50                  55                  60

Arg Lys Glu Lys Ala Asp Asp Leu Ser Val Leu Arg Asn Thr Asn Met
65                  70                  75                  80

Ser Ala Ile Leu Thr Glu Ser Leu Phe Ile Asn Asn Pro Ala Asp Ala
                85                  90                  95

Lys Leu Leu Lys Asp Lys Ser Phe Val Lys Ala Val Ser Val Gly His
                100                 105                 110

Ala Lys Gly Ile Ala
        115

<210> SEQ ID NO 29
<211> LENGTH: 44
<212> TYPE: PRT
<213> ORGANISM: Artificial Sequence
<220> FEATURE:
<223> OTHER INFORMATION: PlyT31 CBD1

<400> SEQUENCE: 29

Thr Tyr Lys Val Gln Lys Gly Asp Thr Leu Tyr Gly Ile Ala Arg Gln
1               5                   10                  15

His Gly Met Ser Val Asp Asp Leu Lys Lys Leu Asn Gly Leu Lys Ser
            20                  25                  30

Asp Ile Ile Arg Val Gly Gln Thr Leu Lys Val Lys
        35                  40

<210> SEQ ID NO 30
<211> LENGTH: 44
<212> TYPE: PRT
<213> ORGANISM: Artificial Sequence
<220> FEATURE:
<223> OTHER INFORMATION: PlyT31 CBD2

<400> SEQUENCE: 30

Thr Tyr Lys Val Lys Lys Gly Asp Thr Leu Tyr Gly Ile Ala Lys Asp
1               5                   10                  15

His Gly Thr Thr Val Ala Asn Ile Lys Lys Leu Asn Asn Leu Lys Ser
            20                  25                  30

Asp Leu Ile Asn Ile Gly Asp Thr Leu Arg Val Lys
        35                  40

<210> SEQ ID NO 31
<211> LENGTH: 1113
<212> TYPE: DNA
<213> ORGANISM: Artificial Sequence
<220> FEATURE:
<223> OTHER INFORMATION: PlyV63 DNA

<400> SEQUENCE: 31
atggcactgg aagcaaacaa atacccgaaa gaaaaaacca tcgtggatat cagccatcat      60
aacgccgata ttgattttga taccgccaaa aactatgtga gcatgtttat tgcacgtacc     120
ggtgatggtc atcgttataa tagcaatggt gaactgcagg gtgttgtgga tcgtaaatac     180
aaaacctttg tggccaatat gaaagcacgt ggtattccgt ttggcaacta tatgtttaat     240

```
cgttttagcg gtgttgccag cgcaaaacaa gaagcagaat ttttctggaa ctatggcgat      300
aaagatgcaa ccgtttgggt tgtgatgca  gaagttagca ccgcaccgaa catgaaagaa      360
tgtattcagg tgtttatcga tcgcctgaaa gaactgggtg caaaaaaagt tggtctgtac      420
atcggtcacc acaaatatca agaatttggt ggcaaagatg tgaactgcga tttcacctgg      480
attccgcgtt atggtaataa accggcattt gcatgtgatc tgtggcagtg gaccgaatat      540
ggtaacattg caggtattgg caaatgcgat attaatgtgc tgtatggtga caaaccgatg      600 agcttttttta ccgaaaaaga aggtgccaaa gaaaccctgg ttccggcact gaataaagtt      660
gttacctatg aagttggcac caacctgatt ccggaaattc aggataaact ggcctttctg      720
ggttatgaag cacgtattaa ctttaccggt ctgggtgatg gcctggttag cattgaaacc      780
agccatcagg tgggtgcaga actggacaaa ctgaccgcat ggctggatga acgtggttgg      840
gcatattact ataccagcag caaagaaggc tataacggta aaagcaaagt ggtgacctat      900
gatatgggca aaacaaaat  tccggaactg agcaatgttc tggcatatca gggtatgcag      960
accgcaattg ttttttaccgg caaaggtgat ggactgattc gtctggaaag caccccctctg     1020 gatgaaagcc gtctgcagaa ctttaaaaac attctggaag cacagaaaat cgcctactat     1080
atgtatagcg aacatcatca ccatcatcat taa                                  1113
```

<210> SEQ ID NO 32
<211> LENGTH: 364
<212> TYPE: PRT
<213> ORGANISM: Artificial Sequence
<220> FEATURE:
<223> OTHER INFORMATION: PlyV63 Protein

<400> SEQUENCE: 32

```
Met Ala Leu Glu Ala Asn Lys Tyr Pro Lys Glu Lys Thr Ile Val Asp
1               5                   10                  15

Ile Ser His His Asn Ala Asp Ile Asp Phe Asp Thr Ala Lys Asn Tyr
            20                  25                  30

Val Ser Met Phe Ile Ala Arg Thr Gly Asp Gly His Arg Tyr Asn Ser
        35                  40                  45

Asn Gly Glu Leu Gln Gly Val Val Asp Arg Lys Tyr Lys Thr Phe Val
    50                  55                  60

Ala Asn Met Lys Ala Arg Gly Ile Pro Phe Gly Asn Tyr Met Phe Asn
65                  70                  75                  80

Arg Phe Ser Gly Val Ala Ser Ala Lys Gln Glu Ala Glu Phe Phe Trp
                85                  90                  95

Asn Tyr Gly Asp Lys Asp Ala Thr Val Trp Val Cys Asp Ala Glu Val
            100                 105                 110

Ser Thr Ala Pro Asn Met Lys Glu Cys Ile Gln Val Phe Ile Asp Arg
        115                 120                 125

Leu Lys Glu Leu Gly Ala Lys Lys Val Gly Leu Tyr Ile Gly His His
    130                 135                 140

Lys Tyr Gln Glu Phe Gly Gly Lys Asp Val Asn Cys Asp Phe Thr Trp
145                 150                 155                 160

Ile Pro Arg Tyr Gly Asn Lys Pro Ala Phe Ala Cys Asp Leu Trp Gln
                165                 170                 175

Trp Thr Glu Tyr Gly Asn Ile Ala Gly Ile Gly Lys Cys Asp Ile Asn
            180                 185                 190

Val Leu Tyr Gly Asp Lys Pro Met Ser Phe Phe Thr Glu Lys Glu Gly
        195                 200                 205
```

```
Ala Lys Glu Thr Leu Val Pro Ala Leu Asn Lys Val Thr Tyr Glu
    210             215                 220

Val Gly Thr Asn Leu Ile Pro Glu Ile Gln Asp Lys Leu Ala Phe Leu
225             230                 235                 240

Gly Tyr Glu Ala Arg Ile Asn Phe Thr Gly Leu Gly Asp Gly Leu Val
                245                 250                 255

Ser Ile Glu Thr Ser His Gln Val Gly Ala Glu Leu Asp Lys Leu Thr
            260                 265                 270

Ala Trp Leu Asp Glu Arg Gly Trp Ala Tyr Tyr Thr Ser Ser Lys
        275                 280                 285

Glu Gly Tyr Asn Gly Lys Ser Lys Val Val Thr Tyr Asp Met Gly Thr
            290                 295                 300

Asn Lys Ile Pro Glu Leu Ser Asn Val Leu Ala Tyr Gln Gly Met Gln
305                 310                 315                 320

Thr Ala Ile Val Phe Thr Gly Lys Gly Asp Gly Leu Ile Arg Leu Glu
                325                 330                 335

Ser Thr Pro Leu Asp Glu Ser Arg Leu Gln Asn Phe Lys Asn Ile Leu
            340                 345                 350

Glu Ala Gln Lys Ile Ala Tyr Tyr Met Tyr Ser Glu
        355                 360

<210> SEQ ID NO 33
<211> LENGTH: 172
<212> TYPE: PRT
<213> ORGANISM: Artificial Sequence
<220> FEATURE:
<223> OTHER INFORMATION: PlyV63 EAD

<400> SEQUENCE: 33

Val Asp Ile Ser His His Asn Ala Asp Ile Asp Phe Asp Thr Ala Lys
1               5                   10                  15

Asn Tyr Val Ser Met Phe Ile Ala Arg Thr Gly Asp Gly His Arg Tyr
            20                  25                  30

Asn Ser Asn Gly Glu Leu Gln Gly Val Val Asp Arg Lys Tyr Lys Thr
        35                  40                  45

Phe Val Ala Asn Met Lys Ala Arg Gly Ile Pro Phe Gly Asn Tyr Met
50                  55                  60

Phe Asn Arg Phe Ser Gly Val Ala Ser Lys Gln Glu Ala Glu Phe
65                  70                  75                  80

Phe Trp Asn Tyr Gly Asp Lys Asp Ala Thr Val Trp Val Cys Asp Ala
                85                  90                  95

Glu Val Ser Thr Ala Pro Asn Met Lys Glu Cys Ile Gln Val Phe Ile
            100                 105                 110

Asp Arg Leu Lys Glu Leu Gly Ala Lys Lys Val Gly Leu Tyr Ile Gly
        115                 120                 125

His His Lys Tyr Gln Glu Phe Gly Gly Lys Asp Val Asn Cys Asp Phe
    130                 135                 140

Thr Trp Ile Pro Arg Tyr Gly Asn Lys Pro Ala Phe Ala Cys Asp Leu
145                 150                 155                 160

Trp Gln Trp Thr Glu Tyr Gly Asn Ile Ala Gly Ile
                165                 170

<210> SEQ ID NO 34
<211> LENGTH: 45
<212> TYPE: PRT
<213> ORGANISM: Artificial Sequence
```

<220> FEATURE:
<223> OTHER INFORMATION: PlyV63 CBD

<400> SEQUENCE: 34

Leu Gly Tyr Glu Ala Arg Ile Asn Phe Thr Gly Leu Gly Asp Gly Leu
1               5                   10                  15

Val Ser Ile Glu Thr Ser His Gln Val Gly Ala Glu Leu Asp Lys Leu
            20                  25                  30

Thr Ala Trp Leu Asp Glu Arg Gly Trp Ala Tyr Tyr Tyr
        35                  40                  45

<210> SEQ ID NO 35
<211> LENGTH: 942
<212> TYPE: DNA
<213> ORGANISM: Artificial Sequence
<220> FEATURE:
<223> OTHER INFORMATION: PlyW68 DNA

<400> SEQUENCE: 35
atggaaatcc gcaaaaatct ggttgatgca agcaaatatg gcaccaaatg tccgtatacc      60
atgaacccgg aatttatcac cgttcacaat acctataatg atgccaccgc caataatgaa     120
gtggcctata tgattcgcaa tgataaccag gtgagctttc atattgccgt ggatgataaa     180
gaagcagttc agggtattcc gctggaacgt aatgcatggc attgtggtga tggtggtggt     240
aatggtaatc gtaaaagcat tggtgtggaa atctgctata gcctgagcgg tggtgatcgt     300
tattacaaag ccgaagataa tgcagcaatt gttgttgcag gtctgatgaa acagtataac     360
attccgatta gcaaagtgcg tacccatcag agctggtcag gtaaatattg tccgcatcgt     420
atgctggcag aaggtcgttg gaatagcttt attgaacgtg ttcagaatgc gtataatggt     480
ggcggtagtc cggttatgcc gaccccgatt ccgcctagca atgatggtac aaaagttgcc     540
tatattaacg gcgataatgt gaatctgcgt aaaggtacag gttatgcggt tattcgtaaa     600
ctgggtaaag gtaatgtgtta tcaggtttgg ggtgaaagca atggttggct gaatctgggt     660
ggcgatcagt gggtttataa tgatagcagc tatattcgct ataccggtga aaatgcaccg     720
gcaccgagca aaccgtcaaa cgatggtatt ggtgttgtga ccattaccgc agatgttctg     780
cgtgttcgta ccggcaccaa ttatggtgtt gttaaaaatg tgtatcagag cgaacgttat     840
cagtcatggg gttatcgtga tggttggtat aatgttggag gtgatcaatg ggttagcggt     900
gaatatgtga atttgaaaaa acatcatcat caccatcatt aa                        942

<210> SEQ ID NO 36
<211> LENGTH: 307
<212> TYPE: PRT
<213> ORGANISM: Artificial Sequence
<220> FEATURE:
<223> OTHER INFORMATION: PlyW68 Protein

<400> SEQUENCE: 36

Met Glu Ile Arg Lys Asn Leu Val Asp Ala Ser Lys Tyr Gly Thr Lys
1               5                   10                  15

Cys Pro Tyr Thr Met Asn Pro Glu Phe Ile Thr Val His Asn Thr Tyr
            20                  25                  30

Asn Asp Ala Thr Ala Asn Asn Glu Val Ala Tyr Met Ile Arg Asn Asp
        35                  40                  45

Asn Gln Val Ser Phe His Ile Ala Val Asp Asp Lys Glu Ala Val Gln
    50                  55                  60

Gly Ile Pro Leu Glu Arg Asn Ala Trp His Cys Gly Asp Gly Gly Gly

```
              65                  70                  75                  80
        Asn Gly Asn Arg Lys Ser Ile Gly Val Glu Ile Cys Tyr Ser Leu Ser
                        85                  90                  95

Gly Gly Asp Arg Tyr Tyr Lys Ala Glu Asp Asn Ala Ala Ile Val Val
                        100                 105                 110

Ala Gly Leu Met Lys Gln Tyr Asn Ile Pro Ile Ser Lys Val Arg Thr
                        115                 120                 125

His Gln Ser Trp Ser Gly Lys Tyr Cys Pro His Arg Met Leu Ala Glu
                        130                 135                 140

Gly Arg Trp Asn Ser Phe Ile Glu Arg Val Gln Asn Ala Tyr Asn Gly
        145                 150                 155                 160

Gly Gly Ser Pro Val Met Pro Thr Pro Ile Pro Ser Asn Asp Gly
                        165                 170                 175

Thr Lys Val Ala Tyr Ile Asn Gly Asp Asn Val Asn Leu Arg Lys Gly
                        180                 185                 190

Thr Gly Tyr Ala Val Ile Arg Lys Leu Gly Lys Gly Glu Cys Tyr Gln
                        195                 200                 205

Val Trp Gly Glu Ser Asn Gly Trp Leu Asn Leu Gly Gly Asp Gln Trp
                        210                 215                 220

Val Tyr Asn Asp Ser Ser Tyr Ile Arg Tyr Thr Gly Glu Asn Ala Pro
        225                 230                 235                 240

Ala Pro Ser Lys Pro Ser Asn Asp Gly Ile Gly Val Val Thr Ile Thr
                        245                 250                 255

Ala Asp Val Leu Arg Val Arg Thr Gly Thr Asn Tyr Gly Val Val Lys
                        260                 265                 270

Asn Val Tyr Gln Ser Glu Arg Tyr Gln Ser Trp Gly Tyr Arg Asp Gly
                        275                 280                 285

Trp Tyr Asn Val Gly Gly Asp Gln Trp Val Ser Gly Tyr Val Lys
                        290                 295                 300

Phe Glu Lys
        305

<210> SEQ ID NO 37
<211> LENGTH: 142
<212> TYPE: PRT
<213> ORGANISM: Artificial Sequence
<220> FEATURE:
<223> OTHER INFORMATION: PlyW68 EAD

<400> SEQUENCE: 37

Tyr Gly Thr Lys Cys Pro Tyr Thr Met Asn Pro Glu Phe Ile Thr Val
        1               5                   10                  15

His Asn Thr Tyr Asn Asp Ala Thr Ala Asn Asn Glu Val Ala Tyr Met
                        20                  25                  30

Ile Arg Asn Asp Asn Gln Val Ser Phe His Ile Ala Val Asp Asp Lys
                        35                  40                  45

Glu Ala Val Gln Gly Ile Pro Leu Glu Arg Asn Ala Trp His Cys Gly
                        50                  55                  60

Asp Gly Gly Asn Gly Asn Arg Lys Ser Ile Gly Val Glu Ile Cys
        65                  70                  75                  80

Tyr Ser Leu Ser Gly Gly Asp Arg Tyr Tyr Lys Ala Glu Asp Asn Ala
                        85                  90                  95

Ala Ile Val Val Ala Gly Leu Met Lys Gln Tyr Asn Ile Pro Ile Ser
                        100                 105                 110

Lys Val Arg Thr His Gln Ser Trp Ser Gly Lys Tyr Cys Pro His Arg
```

```
              115                 120                 125
Met Leu Ala Glu Gly Arg Trp Asn Ser Phe Ile Glu Arg Val
    130                 135                 140

<210> SEQ ID NO 38
<211> LENGTH: 57
<212> TYPE: PRT
<213> ORGANISM: Artificial Sequence
<220> FEATURE:
<223> OTHER INFORMATION: PlyW68 CBD

<400> SEQUENCE: 38

Thr Lys Val Ala Tyr Ile Asn Gly Asp Asn Val Asn Leu Arg Lys Gly
1               5                   10                  15

Thr Gly Tyr Ala Val Ile Arg Lys Leu Gly Lys Gly Glu Cys Tyr Gln
            20                  25                  30

Val Trp Gly Glu Ser Asn Gly Trp Leu Asn Leu Gly Gly Asp Gln Trp
        35                  40                  45

Val Tyr Asn Asp Ser Ser Tyr Ile Arg
    50                  55

<210> SEQ ID NO 39
<211> LENGTH: 48
<212> TYPE: DNA
<213> ORGANISM: Artificial Sequence
<220> FEATURE:
<223> OTHER INFORMATION: IR29 F

<400> SEQUENCE: 39
cgtgaattca tgcatcatca tcatcatcat gattatgata gcagctgg              48

<210> SEQ ID NO 40
<211> LENGTH: 30
<212> TYPE: DNA
<213> ORGANISM: Artificial Sequence
<220> FEATURE:
<223> OTHER INFORMATION: IR30 R

<400> SEQUENCE: 40
cgttctagat tatttaaacg tgccccaata                                  30

<210> SEQ ID NO 41
<211> LENGTH: 54
<212> TYPE: DNA
<213> ORGANISM: Artificial Sequence
<220> FEATURE:
<223> OTHER INFORMATION: IR33 F

<400> SEQUENCE: 41
cgtgaattca tgcatcatca tcatcatcat gattatgata gcagctggtt tacc       54

<210> SEQ ID NO 42
<211> LENGTH: 36
<212> TYPE: DNA
<213> ORGANISM: Artificial Sequence
<220> FEATURE:
<223> OTHER INFORMATION: IR34 R

<400> SEQUENCE: 42
cgttctagat tatttaaagg tgccccaata attcac                           36

<210> SEQ ID NO 43
<211> LENGTH: 54
<212> TYPE: DNA
```

```
<213> ORGANISM: Artificial Sequence
<220> FEATURE:
<223> OTHER INFORMATION: IR37 F

<400> SEQUENCE: 43
cgtgaattca tgcatcatca tcatcatcat tatgatagca gctggtttac accg          54

<210> SEQ ID NO 44
<211> LENGTH: 36
<212> TYPE: DNA
<213> ORGANISM: Artificial Sequence
<220> FEATURE:
<223> OTHER INFORMATION: IR38 R

<400> SEQUENCE: 44
cgttctagat tactgaaagg tgccccaata gctaat                              36
```